(12) United States Patent
Kizer et al.

(10) Patent No.: US 11,889,849 B2
(45) Date of Patent: Feb. 6, 2024

(54) PRODUCT ANALOGS OR COMPONENTS OF SUCH ANALOGS AND PROCESSES FOR MAKING SAME

(71) Applicant: Ripple Foods, PBC, Emeryville, CA (US)

(72) Inventors: Lance Kizer, Oakland, CA (US); Neil Renninger, Peidmont, CA (US); Amanda Stiles, Richmond, CA (US)

(73) Assignee: Ripple Foods, PBC, Berkeley, CA (US)

( * ) Notice: Subject to any disclaimer, the term of this patent is extended or adjusted under 35 U.S.C. 154(b) by 363 days.

(21) Appl. No.: 16/068,567

(22) PCT Filed: Jan. 9, 2017

(86) PCT No.: PCT/US2017/012747
§ 371 (c)(1),
(2) Date: Jul. 6, 2018

(87) PCT Pub. No.: WO2017/120597
PCT Pub. Date: Jul. 13, 2017

(65) Prior Publication Data
US 2019/0000112 A1    Jan. 3, 2019

Related U.S. Application Data

(60) Provisional application No. 62/326,403, filed on Apr. 22, 2016, provisional application No. 62/276,030, filed on Jan. 7, 2016.

(51) Int. Cl.
A23J 1/14    (2006.01)
A23J 3/14    (2006.01)
(Continued)

(52) U.S. Cl.
CPC ............... *A23J 1/14* (2013.01); *A23C 11/103* (2013.01); *A23C 11/106* (2013.01); *A23J 1/006* (2013.01);
(Continued)

(58) Field of Classification Search
CPC ........ A23V 2002/00; A23V 2250/5488; A23V 2200/00; A23V 2200/046;
(Continued)

(56) References Cited

U.S. PATENT DOCUMENTS 3,943,266 A    3/1976 Halik et al.
4,174,313 A    11/1979 Petit et al.
(Continued)

FOREIGN PATENT DOCUMENTS

JP    63240748    10/1988

OTHER PUBLICATIONS

Deak et al., "Effects of NaCl Concentration on Salting-in and Dilution During Salting-out on Soy Protein Fractionation", Journal of Food Science, vol. 71, Nr. 4, 2006, pp. 247-254. (Year: 2006).*
(Continued)

*Primary Examiner* — Elizabeth Gwartney
(74) *Attorney, Agent, or Firm* — FisherBroyles, LLP; Adam K. Whiting; Adelaide K. Leitzel

(57) ABSTRACT

Provided are food products that are derived from non-animal sources that have one or more of the following: color, taste, nutritional content, and other qualities similar to those of dairy products and/or other types of food products. Also provided are processes for production of such dairy-like food products and/or other types of food product analogs.

11 Claims, 30 Drawing Sheets

(51) Int. Cl.

| | | |
|---|---|---|
| C07K 14/415 | (2006.01) | |
| A23J 1/00 | (2006.01) | |
| C07K 16/00 | (2006.01) | |
| A23C 11/10 | (2021.01) | |
| A23L 33/185 | (2016.01) | |
| A23L 9/20 | (2016.01) | |
| A23L 11/60 | (2021.01) | |
| C07K 1/14 | (2006.01) | |
| C07K 1/30 | (2006.01) | |

(52) U.S. Cl.
CPC . *A23J 3/14* (2013.01); *A23L 9/24* (2016.08); *A23L 11/60* (2021.01); *A23L 33/185* (2016.08); *C07K 1/145* (2013.01); *C07K 1/30* (2013.01); *C07K 14/415* (2013.01); *C07K 16/00* (2013.01); *A23V 2002/00* (2013.01); *A23V 2200/00* (2013.01)

(58) Field of Classification Search
CPC .......... A23V 2200/122; A23V 2200/13; A23V 2200/20; A23V 2250/00; A23V 2250/1578; A23V 2250/54; A23V 2250/546; A23V 2250/548; A23V 2300/00; A23V 2300/14; A23V 2300/40; A23J 1/14; A23J 1/006; A23J 3/14; A23J 3/16; A23J 3/227; A23C 11/10; A23C 11/103; A23C 11/106; A23C 20/02; A23C 20/025
See application file for complete search history.

(56) References Cited

U.S. PATENT DOCUMENTS

| | | | |
|---|---|---|---|
| 4,460,613 A | 7/1984 | Yang et al. | |
| 6,780,446 B2 | 8/2004 | Gao | |
| 7,022,355 B2 | 4/2006 | Cho | |
| 2006/0057275 A1* | 3/2006 | Wu | A23J 1/14 426/656 |
| 2006/0073250 A1 | 4/2006 | Mozaffar | |
| 2008/0095914 A1 | 4/2008 | Deak et al. | |
| 2009/0011083 A1* | 1/2009 | Wong | A23J 3/14 426/52 |
| 2010/0063254 A1* | 3/2010 | Lotz | A23J 1/14 530/370 |
| 2011/0038993 A1 | 2/2011 | Schweizer | |
| 2011/0059212 A1 | 3/2011 | Hasegawa | |
| 2012/0135117 A1 | 5/2012 | Segall et al. | |
| 2012/0295008 A1 | 11/2012 | Schweizer | |
| 2014/0065289 A1* | 3/2014 | Green | A23J 1/14 426/656 |
| 2014/0356510 A1 | 12/2014 | Schweizer et al. | |
| 2015/0230497 A1 | 8/2015 | Segall | |
| 2017/0172185 A1 | 6/2017 | Segall et al. | |

OTHER PUBLICATIONS

Singh et al., "Functional and Edible Uses of Soy Protein Products", Comprehensive Reviews in Food Science and Food Safety, vol. 7, 2008, pp. 14-28. (Year: 2008).*
Swanson, B., "Pea and Lentil Protein Extraction and Functionality", JAOCS, vol. 67, No. 5, May 1990, pp. 276-280. (Year: 1990).*
Yuan et al., "Effect of pH and Ca2+-Induced Associations of Soybean Proteins", J. Agric. Food Chem., 50, 2002, pp. 4953-4958. (Year: 2002).*
Clark, K.M., "Mechanistic studies of protein fractionation by precipitation with carboxymethylcellulose", Retrospective Theses and Dissertations. 97/67, 1988, https://lib.dr.iastate.edu/cgi/viewcontent.cgi?article=10766&context=rtd, downloaded Jan. 29, 2020. (Year: 1988).*
Soetrisno et al., "Protein Yields and Characteristics from Acid and Salt Coagulations of Yellow Pea (*Pisum sativum* L. Miranda) Flour Extractions", J. Agric. Food Chem., 40, (1992), pp. 970-974. (Year: 1992).*
International Search Report dated Apr. 3, 2017 for PCT/US2017/012747.
Soetrisno, et al. "Protein Yields and Characteristics from Acid and Salt Coagulations of Yellow Pea (*Pisum sativum* L. Miranda) Flour Extractions." Journal of Agricultural & Food Chemistry, Jun. 1992.
Sosulski, Frank, et al., "Amino Acid Compositon and Nitrogen-to-Protein Conversion Factors for Animal and Plant Foods", J. Agric Food Chem. 1990, 38, pp. 1351-1356.
Renkema et al., "Gel formation by B-conglycinin and glycinin and their mixtures", Food Hydrocolloids 15 (2001) 407-414.
Ratnayake et al., "Pea Starch: Composition, Siruoiure and Properties—A Review", Starch/Starke 54, 217-234, 2002
Kornet, Remco, et al. "How pea fractions with different protein composition and purity can substitute WPI in heat-set gels." Food Hydrocolloids 120 (2021): 106891.
Sakai, Kiyota, Masamichi Okada, and Shotaro Yamaguchi. "Decolorization and detoxication of plant-based proteins using hydrogen peroxide and catalase." Scientific Reports 12.1 (2022): 22432.
Sim, Shaun Yong Jie, et al. "Plant proteins for future foods: A roadmap." Foods 10.8 (2021): 1967.

* cited by examiner

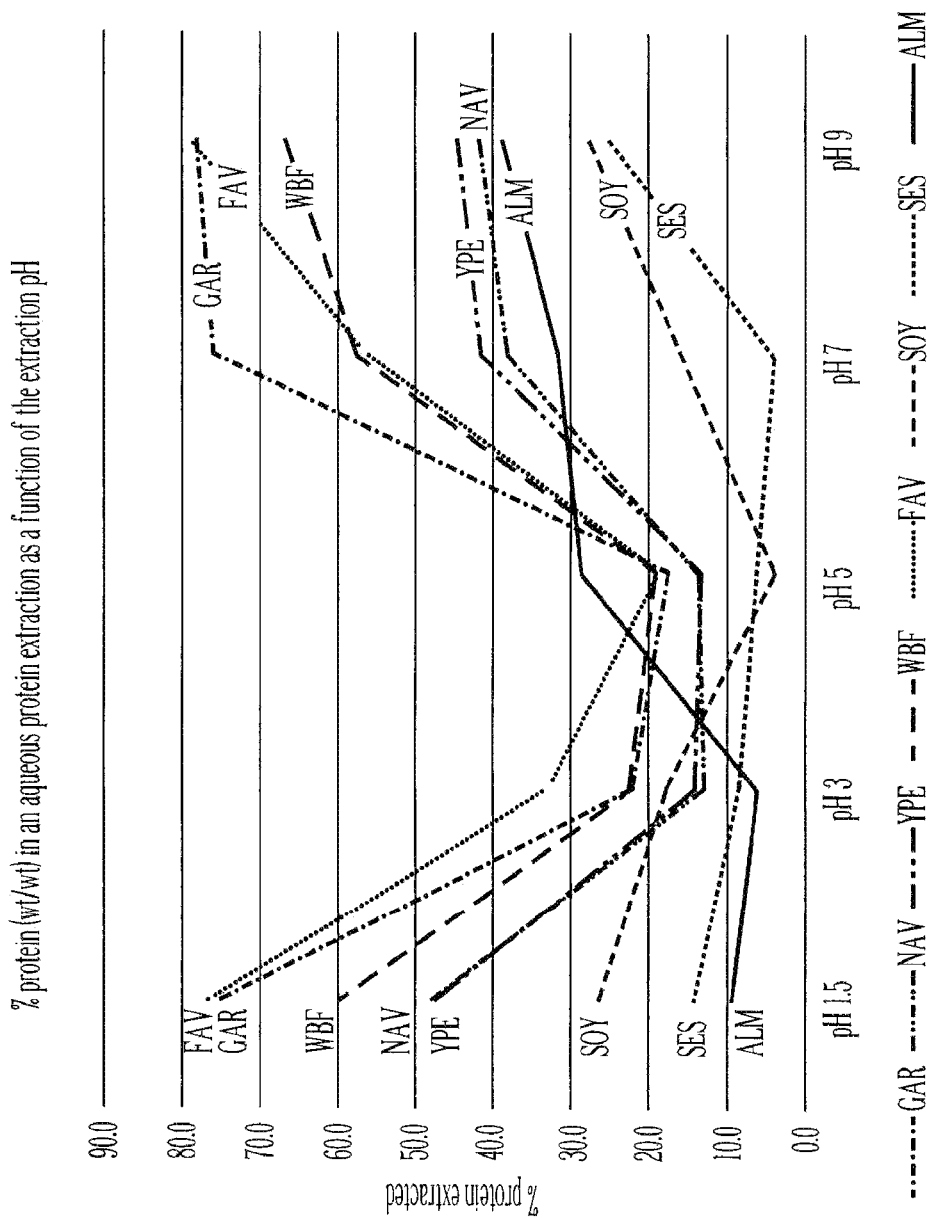

Fat mass % as a function of process step (mass/dry-weight)

Ash mass % as a function of process step (mass/dry-weight)

Total GC peak area for Flour, Commercial Protein and Refined Protein

PRODUCT ANALOGS OR COMPONENTS OF SUCH ANALOGS AND PROCESSES FOR MAKING SAME

CROSS REFERENCE TO RELATED APPLICATIONS

This application is the National Phase application of International Application No. PCT/US2017/012747, filed Jan. 9, 2017, which designates the United States and was published in English, which claims priority to U.S. Provisional Application No. 62/276,030, filed Jan. 7, 2016, and U.S. Provisional Application No. 62/326,403, filed Apr. 22, 2016. These applications, in their entirety, are incorporated herein by reference.

FIELD OF THE INVENTION

The present disclosure relates to food products that are derived substantially from or wholly from non-animal sources, but that have color, flavor, nutritional content, and/or other qualities that are similar to those of dairy products and/or other food products. Also provided are processes for production of such dairy-like food products and/or other analogous food products.

BACKGROUND OF THE INVENTION

Vegetarian and vegan diets provide many benefits to individual consumers and world food requirements. Such benefits include healthy nutrition (e.g., lower saturated fats, no cholesterol), absence of ethical or religious dietary conflicts, less negative environmental impacts (e.g., less greenhouse gases produced in production), and more efficient use of resources (e.g., less water used in production).

Dairy-like food products and other types of analogous food products derived from soybean, coconut, and almond are available to consumers. Demand for these vegetarian/vegan alternatives to dairy products is fueled by intolerances developed by consumers to certain dairy milk constituents. However, acceptance of the dairy substitutes and other analogous food substitutes has been relatively low. This may be due in small part to mounting intolerances experienced by consumers to constituents of these food products (e.g., allergies to soy protein). In larger part, the appearance, flavor and/or mouthfeel of the currently available dairy substitutes and other analogous food substitutes has not appealed to consumers. Moreover, many of the currently available dairy substitutes do not comprise equivalent protein and fat contents as dairy products, and are thus of lower nutritional value.

Production of dairy substitutes and other analogous food substitutes from other natural sources is therefore desirable. However, many natural sources comprise compounds that limit their application in food products. Peas and other leguminous plants, for example, contain compounds that produce distinct colors and/or flavors that are unpleasant and difficult to mask with coloring and/or flavoring agents. The compounds may also affect the structure or stability of proteins, and consequently affect the appearance, sensory and nutritional qualities, and shelf lives of food products derived from such other natural sources.

Therefore, there exists an unmet need for non-animal-derived food products that have the color, taste, nutritional content, and other qualities of dairy products and other analogous food substitutes, that do not challenge common nutritional sensitivities, and that provide consumption experiences consumers are accustomed to from dairy products and other analogous food substitutes. The present disclosure provides such and related food products and refined protein components or refined protein isolates (PI), as well as processes for their production. The present disclosure is directed to solving these and other problems disclosed herein. The present disclosure is also directed to overcome and/or ameliorate at least one of the disadvantages of the prior art as will become apparent from the discussion herein. The present disclosure is also directed to pointing out one or more advantages to using the products, methods and refined protein isolate and/or refined protein components disclosed herein.

SUMMARY OF THE INVENTION

As well as the embodiments discussed in the summary, other embodiments are disclosed in the specification, drawings, and claims. The summary is not meant to cover each and every embodiment; combination or variations are contemplated with the present disclosure.

Certain embodiments are directed to refined protein isolates or refined protein components that may be used for as a component of various food products.

Certain embodiments are directed processes for producing refined protein isolates or refined protein components that may be used for as a component of various food products.

Certain embodiments are directed to food products that comprise protein obtained substantially from or wholly from non-animal natural and/or modified non-animal natural sources, but that have colors, flavors, nutritional contents, and/or other qualities similar to those of dairy products.

Certain embodiments are directed to analogous food products that comprise protein obtained substantially from or wholly from non-animal natural and/or modified non-animal natural sources, but that have colors, flavors, nutritional contents, and/or other qualities similar to those of the food products that they are meant to substitute.

In some such embodiments, the dairy product analogs are dairy milk analogs that comprise at least about 1% by weight of a refined protein obtained from one or more non-animal natural or modified non-animal natural sources, and that have neutral colors that are defined by an L* value of at least about 70, an a* value of between about −1.5 and about +1.5, and a b* value of between about −12 and about +12. Certain embodiments are directed to methods for producing such dairy milk analogs comprising the steps of:
  a) obtaining at least one lipid component;
  b) obtaining at least one color-neutral refined protein component from a non-animal natural and/or modified non-animal natural source;
  c) blending the at least one lipid and the at least one color-neutral refined protein components and an aqueous component to generate a mixture; and
  d) emulsifying at least a portion of the mixture to provide a dairy milk analog.

In some embodiments, the dairy product analogs are dairy yoghurt analogs, and methods for producing such dairy yoghurt analogs may comprise the steps of:
  a) obtaining at least one carbohydrate component;
  b) obtaining at least one lipid component;
  c) obtaining at least one color-neutral refined protein component from a non-animal natural and/or modified non-animal natural source;

d) blending the at least one carbohydrate component, the at least one lipid component, and the at least one refined protein component with an aqueous component to generate a mixture;
e) heating the mixture;
f) emulsifying the mixture to generate an emulsified mixture;
g) cooling the emulsified mixture;
h) adding fermenting microorganisms to the emulsified mixture to generate a fermentation mixture; and
i) incubating the fermentation mixture at an elevated temperature until the fermentation mixture is set and acidified to provide the dairy yoghurt analog.

Certain embodiments are directed to color-neutral refined protein components obtained from non-animal natural and/or modified non-animal natural sources. Certain embodiments are directed to methods for obtaining such color-neutral refined protein components comprising the steps of:
a) obtaining a protein preparation from a non-animal natural and/or modified non-animal natural source;
b) washing the protein preparation at a wash pH;
c) extracting the protein preparation at an extraction pH to obtain an aqueous protein solution;
d) separating the aqueous protein solution from non-aqueous components;
e) adding salt;
f) precipitating the protein from the aqueous protein solution at a precipitation pH to obtain a protein precipitate;
g) separating the protein precipitate from non-precipitated components; and
h) washing the protein precipitate to obtain a color-neutral refined protein component.

Certain embodiments are directed to refined protein components obtained from non-animal natural and/or modified non-animal natural sources. Certain embodiments are directed to methods for obtaining such refined protein components comprising the steps of:
a) obtaining a protein preparation from a non-animal natural and/or modified non-animal natural source;
b) washing the protein preparation at a wash pH;
c) extracting the protein preparation at an extraction pH to obtain an aqueous protein solution;
d) separating the aqueous protein solution from non-aqueous components;
e) adding salt;
f) precipitating the protein from the aqueous protein solution at a precipitation pH to obtain a protein precipitate;
g) separating the protein precipitate from non-precipitated components; and
h) washing the protein precipitate to obtain a refined protein component.

BRIEF DESCRIPTION OF THE DRAWINGS

Embodiments of the present disclosure are described, by way of example only, with reference to the accompanying figures.

FIG. 2 shows the percentage protein extracted for 8 flour/protein isolate (PI) sources at increasing pH values, according to certain embodiments.

DETAILED DESCRIPTION OF THE INVENTION

Figure 1A:
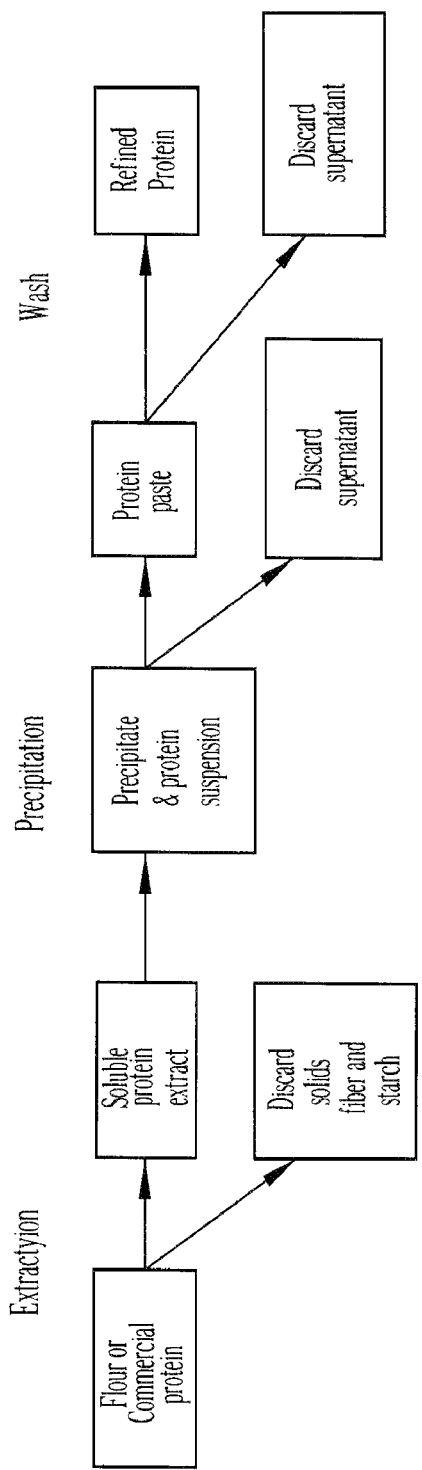
FIGS. 1A-B provide over views of the refined protein isolation process, according to certain embodiments.

Unless defined otherwise, all technical and scientific terms used herein have the same meaning as is commonly understood by one of ordinary skill in the art to which this disclosure pertains.

Definitions

The term "analogous dairy product" as used herein refers to a food product that is mimicked by a dairy product analog and for which the dairy product analog may serve as a substitute. Examples of analogous dairy products include, but are not limited to, milk (e.g., whole dairy milk, dairy milk comprising 2% by weight of fat [2% milk], dairy milk comprising 1% by weight of fat [1% milk], dairy milk not comprising fat [skim milk], dairy milk comprising supplemented calcium [calcium-fortified milk]), crème fraiche, clotted dairy milk, single cream, double cream, whipping cream, cultured dairy milk, Kefir, powdered dairy milk, condensed dairy milk, Khoa, evaporated dairy milk, Ricotta, infant formulas, baked milk, butter, buttermilk, Ghee, Smen, anhydrous milkfat, cheese, curds, Paneer, whey, cottage cheese, quark, cream cheese, Fromage frais, yoghurt, Ayran, Lassi, Leben, clabber, gelato, ice cream, ice milk, frozen custard, frozen yoghurt, Villi, Kajmak, Filmjoelk, Piima, Vla, Dulce de leche, Skyr, and Junket.

The term "analogous food product" as used herein refers to refers to a food product that is mimicked by a food product analog and for which the food product analog may serve as a substitute. Examples of analogous food products include, dairy products, supplement (powders, pastes for athletes, health), nutrition shakes/drinks, energy bars, meat substitutes, eggs substitutes (as ingredients in baking, formulations or as end consumer products like a scramble), spreads (savory or sweet), snack foods and/or salad dressings/condiments.

The term "color-neutral refined protein component" as used herein refers to a protein preparation that has a color that is defined by an L* (lightness) value of at least about 70, an a* (red/green) value of between about −20 and about 20, and a b* (yellow/blue) value of between about −30 and about 30, measured according to the method disclosed in Example 6 or Example 8. However, to be clear many of the embodiments disclosed herein may or may not be color-neutral as that term is used herein.

The term "dairy milk" as used herein refers to a white fluid secreted by the mammary glands of female mammals. Dairy milk consists of an emulsion of fat in an aqueous solution comprising proteins (e.g., casein, albumin), sugars, inorganic salts, and other ingredients. Suitable mammals from which dairy milk can be obtained include but are not limited to cow, sheep, goat, buffalo, donkey, horse, camel, yak, water buffalo, human, and other mammals. Dairy milk obtained from cow typically contains around 3.5% fat (whole cow milk). Fat levels can be reduced to standardized levels to obtain different grades of cow milk that comprise from 0% to about 75% by weight of the fat present in whole cow milk, including but not limited to 2% cow milk (cow milk comprising 2% by weight of fat), 1% cow milk (cow milk comprising 1% by weight of fat), and skim cow milk (cow milk comprising no fat).

The terms "dairy product analog", "dairy milk analog", and "dairy yoghurt analog" as used herein refer to food products that are produced to have one or more of the following: substantially similar (or similar) color, taste, nutritional content, and other quality as an analogous dairy product, dairy milk, or dairy yoghurt, respectively, and that can be used as a substitute for the analogous dairy product, dairy milk, or dairy yoghurt, respectively, but that are made from natural sources and/or modified natural sources. The terms encompass food products that may have the same, or substantially similar, advantageous qualities but may not the have the same, or substantially similar, disadvantageous qualities as the analogous dairy food products. Some non-limiting examples of disadvantageous qualities are presence of saturated fat, amount of fat, presence of cholesterol, and presence of lactose.

The terms "food product analog" as used herein refer to food products that are produced to have one or more of the following: substantially similar (or similar) color, taste, nutritional content, and other quality as an analogous food product, and that can be used as a substitute for the analogous food product but that are made from natural sources and/or modified natural sources. The terms encompass food products that may have the same, or substantially similar, advantageous qualities but may not have the same, or substantially similar, disadvantageous qualities as the analogous food products. Some non-limiting examples of disadvantageous qualities are presence of saturated fat, amount of fat, presence of cholesterol, and presence of lactose. Exemplary food product applications includes, but is not limited to, refined proteins as a supplement (powders, pastes for athletes, health), nutrition shakes/drinks, energy bars, meat substitutes, eggs substitutes (as ingredients in baking, formulations or as end consumer products like a scramble), spreads (savory or sweet), snack foods and/or salad dressings/condiments.

The term "modified natural source" as used herein refers to a natural source that is altered from its native state (e.g., mutated, genetically engineered).

The term "non-animal natural source" as used herein refers to a naturally occurring plant, algae, fungus, and/or microbe.

The term "nutritional profile" as used herein refers to the types and amounts of ingredients comprised in a food product and/or a component of a food product. For example, the nutritional profiles of dairy products may be generally defined by the content of their ingredients, which include but are not limited to total protein content, total lipid content, total carbohydrate content, total edible fiber content, calcium content, sodium content, types and amounts of vitamins present, and combinations thereof.

The term "meal" as used herein refers to the whole or coarsely ground grains of cereal grass.

The term "microbe" as used herein is an abbreviation for microorganism, and refers to a unicellular organism. As used herein, the term includes all bacteria, all archaea, unicellular protista, unicellular animals, unicellular plants, unicellular fungi, unicellular algae, all protozoa, and all chromista.

The term "protein preparation" as used herein refers to a preparation derived from a natural source and/or modified natural source that contains protein. The term encompasses protein isolate, protein concentrate, protein flour, meal and/or combinations thereof.

The term "protein concentrate" as used herein refers to the protein material that is obtained from a natural source and/or modified natural source upon removal of at least a portion of (or a substantial portion of) one or more of the following: carbohydrate, ash, and other minor constituents. It typically comprises at least about 30%, 40%, 50%, 60%, 70% or 80% by weight of protein.

The term "protein isolate" as used herein refers to the protein material that is obtained from a natural source and/or modified natural source upon removal of at least a portion of (or a substantial portion of) one or more of the following: insoluble polysaccharide, soluble carbohydrate, ash, and other minor constituents. It typically has at least about 40%, 50% 60%, 70%, or 80% by weight of protein.

The terms "a" and "an" and "the" and similar referents as used herein refer to both the singular and the plural, unless otherwise indicated herein or clearly contradicted by context.

The term "about" as used herein refers to greater or lesser than the value or range of values stated by 1/10 of the stated values, but is not intended to limit the value or range of values to only this broader definition. For instance, a value of "about 30%" means a value of between 27% and 33%. Each value or range of values preceded by the term "about" is also intended to encompass the embodiment of the stated absolute value or range of values.

As used herein, the term "comprising" means "including." Variations of the word "comprising", such as "comprise" and "comprises," have correspondingly varied meanings. Thus, for example, a method "comprising" steps 'A' and 'B' may consist exclusively of steps 'A' and 'B' or may include one or more additional steps (e.g., steps 'A', 'B', and 'C').

The subject headings used in the detailed description are included for the ease of reference of the reader and should not be used to limit the subject matter found throughout the disclosure or the claims. The subject headings should not be used in construing the scope of the claims or the claim limitations.

Dairy Product Analogs

Certain embodiments are directed to food products that comprise refined protein obtained substantially from or wholly from non-animal natural and/or modified non-animal natural sources, but that have colors, flavors, nutritional contents, and/or other qualities similar to those of dairy products.

In some embodiments, the dairy product analogs provided herein are analogs of dairy milk. In other embodiments, the dairy product analogs are analogs of food products commonly derived from dairy milk, including, but not limited to, cooking milk, sweetened condensed milk, flavored milk, yoghurt, cheese, smoothies, shakes, coffee whiteners, coffee creamers, infant formulas, weight loss beverages, nutritional supplemental beverages, clinical nutrition beverages, powdered beverages, and frozen confections (for example, ice cream, soft ice cream, frozen yoghurt, sundae, pudding, whipped topping) or combinations thereof. In some embodiments, the dairy product analogs are primarily, substantially, or entirely composed of ingredients derived from non-animal natural sources. In alternative embodiments, the dairy product analogs are composed of ingredients partially derived from animal sources but supplemented with ingredients derived from non-animal natural sources. The dairy product analogs provided herein may be prepared for human or animal consumption, including domesticated animals (for example, dogs, cats), farm animals (for example, cows, pigs, horses), and wild animals (for example, non-domesticated predatory animals). The dairy product analogs may be used for various purposes, including, but not limited to, feeding and delivery of active ingredients (for example, vitamins, minerals, nutrients, therapeutics).

The dairy product analogs provided herein have one or more of the advantages discussed in this disclosure. For example, 1. the dairy product analogs are not or not primarily derived from animals, and may therefore be produced in more sustainable manners;
2. the dairy product analogs can be produced from a variety of non-animal natural sources (e.g., legumes, cereal grains, flax), broadening their nutritional content and opening up possibilities for local sourcing of ingredients in areas that are not cultivatable by the crops that are currently used to make dairy product analogs
3. the dairy product analogs provide similar or superior nutritional qualities to analogous dairy products;
4. the dairy product analogs provide similar or superior levels of protein, carbohydrate, vitamins, minerals, and/or other health benefits (for example, a dairy product analog may comprise equal to or greater levels of protein, about 75% or more lower levels of saturated fat, about 25% or more lower levels of sugar, and/or equal or greater levels of calcium than dairy milk [e.g., whole cow milk, 2% cow milk, 1% cow milk, skim cow milk, or other dairy milk]; or a yogurt product analog may comprise about 50% or more lower levels of protein, about 75% or more lower levels of saturated fat, and/or more than 25% or less sugar, and equal or greater levels of calcium that dairy yoghurt [e.g., whole cow yoghurt, 2% cow yoghurt, 1% cow yoghurt, skim cow yoghurt, or other dairy yoghurt]); and/or
5. the dairy product analogs are produced to have substantially lower levels and/or be devoid of certain ingredients that are less conducive to the general health of consumers (e.g., total sugars, saturated fat, total fat, and/or cholesterol) or to the well-being of subgroups of consumers (e.g., lactose).

One feature of the dairy product analogs provided herein is that they may have similar, or substantially similar, colors as analogous dairy products. The color of a food product may be determined, for example, using a colorimeter or spectrophotometer that can measure light reflectance and the $L^*a^*b$ color space (see, for example, Jovanka et al., (2008) Color Changes of UHT Milk During Storage, Sensors 8(9): 5961-5974; Zare et al. (2013) Probiotic Milk Supplementation with Pea Flour: Microbial and Physical Properties, Food and Bioprocess Technology 6(5): 1321-1331; Sanz et al., (2008) Yogurt enrichment with functional asparagus fibre, Effect of fibre extraction method on rheological properties, colour, and sensory acceptance. European Food Research and Technology. Vol 227 (5) 1515-1521; Brewer and Rankin (1998) Color of Nonfat Fluid Milk as Affected by Fermentation. Journal of Food Science. 63(1):178-180). The dairy product analogs provided herein have colors that are defined by $L^*$ values of at least about 70, $a^*$ values of between about −1.5 and about +1.5, and $b^*$ values of between about −12 and about +12, measured according to the method disclosed in Example 6. Alternatively, the color of a food product can be evaluated by a panel of human sensory experts.

The dairy product analogs provided herein may also have similar flavors as analogous dairy products, and/or similar or superior flavors to existing alternative dairy products (e.g., soy milk, almond milk). The flavor of a food product can be evaluated, for example, by various methods, including but not limited to by blind tasting performed by human testers or human sensory experts.

The dairy product analogs provided herein may comprise less, similar, or larger amounts of protein than the analogous dairy products. In some embodiments, the dairy product analog comprises between about 0.01% and about 40%, between about 0.5% and about 30%, between about 1% and about 20%, between about 1% and about 10%, between about 1.5% and about 10%, between about 2% and about 8%, between about 1% and about 3%, between about 2% and about 5%, or between about 3% and about 7% by weight of protein obtained from non-animal natural and/or modified non-animal natural sources. In some embodiments, the dairy product analog comprises at least 0.01%, 0.5%, 1% 1.5%, 2%, 3%, 5%, 7%, 10%, 15%, 20%, 30% or 40% by weight of protein obtained from non-animal natural and/or modified non-animal natural sources. In some embodiments, the ratio of protein to lipid in the dairy product analog is about 1:5, 1:4, 1:3, 1:2, 1:1, 2:1, 3:1, 4:1, 5:1, or 10:1. Protein content of a food product may be determined by a variety of methods, including, but not limited to, AOAC International reference methods AOAC 990.03 and AOAC 992.15, and combustion analysis (ISO 14891:2008). In some embodiments, the dairy product analogs have similar, or substantially similar, amino acid profiles as analogous dairy products. In some embodiments, the amino acid profile in the types of amino acids and in the total amount of each amino acid of the dairy product analog is at least 50%, 60%, 70%, 80%, 90% or 95% by weight the same as the amino acid profile of the analogous dairy product. In some embodiments, the dairy product analog has an amino acid profile in the types of amino acids and in the total amount of each amino acid that is at least 50%, 60%, 70%, 80%, 90% or 95% by weight the same as the amino acid profile of the protein preparation derived from non-animal sources that was used in preparing the dairy product analog. In some embodiment, the dairy product analogs have similar amino acid profiles as, for example, legumes or mixtures of legumes, grains and oil seeds. In some embodiments, the dairy product analog has an amino acid profile in the types of amino acids and in the total amount of each amino acid that is at least 50%, 60%, 70%, 80%, 90% or 95% by weight the same as the amino acid profile of the legumes or mixtures of legumes that was used in preparing the dairy product analog.

The dairy product analogs provided herein may further comprise lipids. In some embodiments, the dairy product analogs comprise between 0% and about 10%, between about 0.5% and about 8%, between about 1% and about 7%, between about 21.5% and about 6%, between about 2% and about 5%, between about 2.5% and about 4%, between 0% and about 4%, or between about 2% and about 4% by weight of lipids obtained from non-animal natural, modified non-animal natural or from mixtures of such sources. Lipid content of a food product may be determined by a variety of methods, including, but not limited to, AOAC International reference method AOAC 954.02. Examples of suitable lipids include, but are not limited to, docosahexaenoic acid, eicosapentaenoic acid, conjugated fatty acids, eicosanoids, palmitic acid, glycolipids (e.g., cerebrosides, galactolipids, glycosphingolipids, lipopolysaccharides, gangliosides), membrane lipids (e.g., ceramides, sphingomyelin, bactoprenol), glycerides, second messenger signaling lipid (e.g., diglyceride), triglycerides, prenol lipids, prostaglandins, saccharolipids, oils (e.g., non-essential oils, essential oils, almond oil, aloe vera oil, apricot kernel oil, avocado oil, baobab oil, calendula oil, canola oil, corn oil, cottonseed oil, evening primrose oil, grape oil, grape seed oil, hazelnut oil, jojoba oil, linseed oil, macadamia oil, natural oils, neem oil, non-hydrogenated oils, olive oil, palm oil, partially hydrogenated oils, peanut oil, rapeseed oil, sesame oil, soybean oil, sunflower oil, synthetic oils, vegetable oil), omega-fatty acids (e.g., arachidonic acid, omega-3-fatty acids, omega-6-fatty acids, omega-7-fatty acids, omega-9-fatty acids), and phospholipids (e.g., cardiolipin, ceramide phosphocholines, ceramide phosphoethanolamines, glycerophospholipids, phasphatidicacid, phosphatidylcholine, phosphatidylethanolamine, phosphatidylinositol, phosphospingolipids, phsophatidylserine), or combinations thereof. In certain embodiments, examples of suitable lipids may be selected from one or more of the following: sunflower oil, canola oil, soybean oil, palm oil, cocoa butter.

In some embodiments, the dairy product analogs provided herein comprise similar, substantially similar, or reduced amounts of carbohydrate as analogous dairy products. Carbohydrate content of a food product may be determined by a variety of methods, including, but not limited to, high performance liquid chromatography. Examples of suitable carbohydrates include, but are not limited to, sucrose, glucose, fructose, mannose, steviosides, artificial sweeteners, or combinations thereof. In certain embodiments, examples of suitable carbohydrates may be selected from one or more of the following: sucrose, glucose, fructose. In some embodiments, the dairy product analog comprise between about 0.5% and about 15%, between about 1% and about 10%, or between about 3% and about 8% by weight of carbohydrate. In some embodiments, the dairy product analog comprise at least 0.5%, 1%, 3%, 5%, 8% 10% or 15% by weight of carbohydrate. In some embodiments, the dairy product analogs comprise about 30%, 40%, 50%, 60%, or 70% by weight less total carbohydrate than in an equivalent sized serving of plain yogurt or dairy milk, regardless of fat content. In some embodiments, the dairy product analogs do not comprise lactose. In some embodiments, the dairy product analog contains less than 5%, 3%, 1%, or 0.5% by weight of lactose. In some embodiments, the dairy product analogs comprise sucrose.

The protein, lipid, and carbohydrate comprised in the dairy product analogs provided herein may be derived from a non-animal natural source, a modified non-animal natural source, multiple non-animal natural sources, multiple modified non-animal natural sources, or combinations thereof. In some embodiments, at least some of the protein, lipid, and/or carbohydrate is not derived from a non-animal natural source or a modified non-animal natural source but is identical, substantially identical or similar to protein, lipid, and/or carbohydrate found in the non-animal natural source or modified non-animal natural source. For example, the protein may be synthetically or biosynthetically generated but comprise polypeptide molecules that have an identical, substantially identical or similar amino acid sequence as polypeptide molecules found in a non-animal natural source. In some embodiments, at least some of the protein, lipid, and/or carbohydrate is not derived from a non-animal natural source or a modified non-animal natural source. The protein, lipid, or carbohydrate may be comprised of molecules having identical structures, or of a mixture of molecules having at least 2 different structures. In some embodiments, at least 25%, 50%, 75%, 90%, 95%, 99%, or 100% by weight of the protein, lipid, and/or carbohydrate is derived from plant. For example, the protein of the plant could be derived from a legume. Examples of legumes include but are not limited to alfalfa, lentils, beans, clovers, peas, fava coceira, frijole bola roja, frijole negro, lespedeza, licorice, lupin, mesquite, carob, soybean, peanut, tamarind, wisteria, cassia, chickpea, garbanzo, fenugreek, green pea, yellow pea, snow pea, lima bean, fava bean, black bean, baby bean or combinations thereof. As a further example, the carbohydrate could be derived from a sugar cane, sugar beet, agave, corn, or stevia, or combinations thereof. As a further example, the lipid could be derived from an oilseed containing plant such as soybean, sunflower, oil palm, rapeseed, flaxseed, or other oil bearing plant such as corn.

In some embodiments, the dairy product analogs provided herein comprise similar amounts of calcium as analogous dairy products. In some embodiments, the dairy product analogs comprise similar amounts of calcium as calcium-fortified analogous dairy products. In some embodiments, the dairy product analog comprise between about 5 mg and about 3,000 mg, between about 50 mg and about 1,500 mg, between about 100 mg and about 1,300 mg, between about 200 mg and about 1,000 mg, or between about 300 mg and about 600 mg of calcium per cup (8 ounces, 224 g). In some embodiments, the dairy product analog comprise at least 5 mg, 50 mg, 100 mg, 200 mg, 500 mg, 1000 mg, 1500 mg or 2500 mg of calcium per 8 ounces or 224 g. Calcium content of a food product can be determined by a variety of methods, including but not limited to inductively coupled plasma (ICP) analysis.

Dairy products are sold in a variety of forms, homogenized, but also, for example, with reduced fat, different types of fats (e.g. unsaturated lipids), lacking lactose, lacking permeate, or with added vitamins and minerals. The dairy product analogs provided herein can be formulated to match, or substantially match, the nutritional profile of one or more of these different types of dairy products. In some embodiments, the dairy product analog may have healthier nutritional profiles than analogous dairy products. In some embodiments, the dairy product analog may have reduced levels of total fat, reduced levels of saturated fats, reduced levels of cholesterol, increased levels of vitamins or minerals, increased levels of protein, lower levels of sugar, or be comprised of other sugars or sweetening agents in place of lactose, or combinations thereof, compared to the equivalent quantity of whole dairy milk, whole dairy yoghurt, or other product made from whole dairy milk.

In some embodiments, the ingredients of the dairy product analogs provided herein are natural, or substantially natural, so that the dairy product analogs may appeal to consumers who have a preference for natural ingredients (i.e., ingredients that are not genetically engineered or that have a risk of being contaminated at any stage in the food chain with genetically modified material, such as with soy products or soy-based components, for example; ingredients that are using organic farming techniques). In some embodiments, the dairy product analogs do not contain gluten, so that they appeal to consumers who suffer from celiac disease or who chose to not consume gluten. In some embodiments, the dairy product analog contains less then 1%, 0.5%, 0.1% or 0% by weight of gluten. In some embodiments, the dairy product analogs do not contain nuts that can cause strong allergic reactions (e.g., peanuts). In some embodiments, the dairy product analog contains less than 1%, 0.5%, 0.1%, or 0% nuts. In some embodiments, the dairy product analog does not contain ingredients that consumers may consider to be unhealthy (e.g., cholesterol, trans-fats, lecithin, phosphate salts, food coloring agents, artificial sweeteners, or excessive amounts of sodium). In some embodiments, the dairy product analog is substantially free of or wholly free of ingredients that contain cholesterol, trans-fats, phosphate salts, food coloring agents, artificial sweeteners, excessive amounts of sodium, or combinations thereof. In some embodiments, the dairy product analogs have a shelf life of 2, 3, 4, or 6 months when processed for extended shelf life and kept under refrigerated conditions, or 3, 6, 9, or 12 months when processed aseptically and kept at room temperature.

Methods for Producing Dairy Product Analogs

Certain embodiments are directed to methods for producing the dairy product analogs.

In some embodiments, the methods are for producing dairy milk analogs, and may comprise one or more of the following steps, in or out of order:
  a) obtaining at least one lipid component;
  b) obtaining at least one color-neutral refined protein component from a non-animal natural and/or modified non-animal natural source;
  c) blending the at least one lipid component and the at least one color-neutral refined protein component with an aqueous component to generate a mixture; and
  d) emulsifying at least a portion of the mixture to provide a dairy milk analog;

whereby the quantities and proportions of the at least one lipid and at least one color-neutral refined protein components are selected so as to provide a desired nutritional profile.

In some embodiments, the methods are for producing dairy milk analogs, and may comprise one or more of the following steps, in or out of order:
  a) obtaining at least one lipid component;
  b) obtaining at least one refined protein component from a non-animal natural and/or modified non-animal natural source;
  c) blending the at least one lipid component and the at least one refined protein component with an aqueous component to generate a mixture; and
  d) emulsifying at least a portion of the mixture to provide a dairy milk analog;

whereby the quantities and proportions of the at least one lipid and at least one refined protein components are selected so as to provide a desired nutritional profile.

Methods for obtaining the at least one lipid component are known in the art. In some embodiments, the at least one lipid component is obtained from a non-animal natural and/or modified non-animal natural source. Methods for obtaining the at least one color-neutral refined protein component from a non-animal natural and/or modified non-animal natural source are provided herein. In some embodiments, the lipid component and/or protein component are obtained as slurries. In some embodiments, the lipid component and/or protein component are obtained in solid form. In some embodiments, the color-neutral refined protein component is combined with one or more other proteins prior to being mixed with the at least one lipid component.

The aqueous phase may be an aqueous liquid, including but not limited to pure water, tap water, bottled water, deionized water, spring water, or a mixture thereof.

The lipid, protein, and aqueous components may be mixed in various orders. In some embodiments, the three components are mixed simultaneously. In other embodiments, the lipid component is mixed with the protein component before the aqueous component is introduced into the mixture. In yet other embodiments, the protein component is mixed with the aqueous component before the lipid component is introduced into the mixture. In yet other embodiments, the lipid component is nixed with the aqueous component before the protein component is introduced into the mixture.

Combining the lipid, protein, and aqueous components may be accomplished using a variety of mixing devices, for example, mechanical agitators and/or pressure jets. The components may also be stirred or mixed by hand. Mixing may continue until the components are distributed substantially evenly throughout the mixture.

In some embodiments, a carbohydrate component is further added. A variety of ingredients may be used as the carbohydrate component, including but not limited to starch, simple sugars, flour, edible fiber, and combinations thereof. Examples of suitable starches include but are not limited to maltodextrin, inulin, fructo oligosaccharides, pectin, carboxymethyl cellulose, guar gum, corn starch, oat starch, potato starch, rice starch, wheat starch, or combinations thereof. Examples of suitable flour include but are not limited to amaranth flour, oat flour, quinoa flour, rice flour, rye flour, sorghum flour, soy flour, wheat flour, corn flour, or combinations thereof. Examples of suitable edible fiber include but are not limited to barley bran, carrot fiber, citrus fiber, corn bran, soluble dietary fiber, insoluble dietary fiber, oat bran, pea fiber, rice bran, head husks, soy fiber, soy polysaccharide, wheat bran, wood pulp cellulose, or combinations thereof. In some embodiments, the carbohydrate component does not comprise lactose or substantially does not comprise lactose. The carbohydrate component may be present in the aqueous component before mixing. Alternatively, the carbohydrate component is added to the lipid and/or protein components or to the lipid, protein, and aqueous mixture.

In some embodiments, one or more other ingredients are further added. In some such embodiments, the one or more other ingredients are added to the aqueous component before mixing. In other embodiments, the one or more other ingredients are added to the lipid and/or protein components or to the lipid, protein, and aqueous mixture. In some embodiments, the one or more other ingredients include calcium.

Emulsification may occur without additional mechanical energy, or require mechanical energy (for example, vortexing, homogenization, agitation, sonication, or other suitable mechanical activity). When emulsification is aided by lower amounts of mechanical energy (for example, agitation in a conventional mixer under moderate shear of between about 100 rpm and about 1,000 rpm), the average droplet size of the resulting emulsion is typically larger (for example, at least about 75% of the droplets have a diameter greater than about 25 um). When emulsification is aided by higher amounts of mechanical energy (e.g., homogenization in a high-pressure [for example, between about 35 bar and about 650 bar] 1- or 2-stage homogenizer [e.g., between about 1,000 rpm and about 10,000 rpm], or microfluidic homogenization [between about 500 and about 2,000 bar]), the average droplet size of the resulting emulsion is typically smaller (for example, at least about 75% of the droplets have a diameter of less than about 10 um). Nanoemulsions may be obtained by homogenizing in a microfluidizer or other suitable equipment. In certain applications, to obtain higher lipid emulsions, the lipid component may be added gradually during mixing. Heating may aid in emulsification in certain applications. In some embodiments, emulsification is performed at greater than room temperature, greater than 30° C., 40° C., 50° C., 60° C., 70° C., or 80° C., between about 90° C. and about 120° C., between about 30° C. and about 60° C., or between about 40° C. and about 50° C. Heating is generally followed by cooling. Emulsification may be monitored by removing a sample of the mixture and analyzing it by such methods as microscopy, light scattering, and/or refractometry.

The emulsions may have droplets of various sizes. In some embodiments, the emulsions are polydisperse emulsions (i.e., emulsions comprising droplets with a broad distribution of droplet sizes). In other embodiments, the emulsions are monodisperse (i.e., emulsions comprising droplets with a narrow distribution of droplet sizes). In some embodiments, the emulsions are microemulsions (i.e., thermodynamic stable systems of dispersed droplets in continuous phase). In other embodiments, the emulsions are nanoemulsions (i.e., metastable [or kinetically stable] dispersions of one liquid in different immiscible liquid having droplet sizes ranging from 1 to 100 nm). In some embodiments, the emulsions have an average droplet size of less than about 1,000 nm, less than about 750 nm, less than about 500 nm, less than about 250 nm, less than about 100 nm, or less than about 50 nm, between about 100 nm and about 800 nm, or between about 100 nm and about 300 nm. In some embodiments, droplet sizes are reduced to reduce the lipid contents of the emulsions and dairy milk analogs provided herein. The degree of emulsification achieved and hence the final textures of the emulsions may be controlled to a certain degree by varying certain parameters during emulsification. Examples of such parameters include, but are not limited to, the type and/or amount of lipid component, the type and/or amount of protein component, the type and/or amount of optional emulsifiers, the amount of mechanical energy used during emulsification, the centrifugation or filtration techniques, the pH of the aqueous component, the temperature during mixing, the amount of optional salt in the aqueous component or combinations thereof.

In some embodiments, the dairy milk analog is sterilized or pasteurized. Sterilization may occur by UV irradiation, heating (e.g. steam sterilization, flaming, or diy heating), or chemical sterilization (e.g., exposure to ozone). In some embodiments, sterilization kills more than 95% of microbes. For pasteurization, the dairy milk analogs are heated to a temperature (e.g., between about 280 and about 306° F.) and held at such temperature for a period of time (e.g., between about 1 and about 10 seconds). Appropriate pasteurization steps are known in the art of food manufacturing and may be undertaken at a variety of temperatures and/or for a variety of time durations. Pasteurization may be high-temperature, short-time (HTST), "extended shelf life" (ESL) treatment, high pressure pasteurization (HPP), ultra pasteurization (UP), ultra-high temperature (UHT) or combinations thereof. A controlled chilling system may be used to rapidly cool the dairy milk analogs. In some embodiments, the dairy milk analog undergoes vacuum cooling to remove volatiles and water vapor following pasteurization.

In certain embodiments, the source and/or quantities of the components are selected to provide the appropriate levels of ingredients, without additional supplementation being needed. For example, use of low fat natural sources from which the lipid component or protein component are isolated can facilitate production of a reduced-fat dairy milk analog. Such low lipid natural sources include, but are not limited to, partially defatted natural sources. Alternatively, components may be extracted from natural sources and the lipids removed from the extracts using conventional or non-conventional approaches, such as centrifugation or membrane separation. Similarly, careful selection of the natural sources and seasonal variations from which ingredients of the dairy milk analogs are extracted may provide appropriate levels of other ingredients, including, but not limited to, vitamins, minerals, edible fiber, antioxidants or combinations thereof. Levels of ingredients may be further adjusted by supplementation.

The dairy milk analogs may optionally be dried to obtain powders. Drying may be performed in a suitable way, including but not limited to spray drying, dry mixing, agglomerating, freeze drying, microwave drying, drying with ethanol, evaporation, refractory window dehydration or combinations thereof.

The dairy milk analogs provided herein may be used as a base for production of the other dairy product analogs with certain nutritional profiles. In some embodiments, such other dairy product analogs are yoghurt analogs. The methods for producing yoghurt analogs provided herein may comprise one or more of the following steps, in or out of order:

a) obtaining at least one carbohydrate component;
   b) obtaining at least one lipid component;
   c) obtaining at least one color-neutral refined protein component from a non-animal natural and/or modified non-animal natural source;
   d) blending the at least one carbohydrate, the at least one lipid, and the at least one refined protein component with an aqueous component to generate a mixture;

e) heating the mixture;

f) emulsifying at least a portion of the mixture to generate an emulsified mixture;

g) cooling the emulsified mixture;

h) adding fermenting microorganisms to the emulsified mixture to generate a fermentation mixture; and i) incubating the fermentation mixture at an elevated temperature until the fermentation mixture is set and acidified to provide the dairy yoghurt analog;

whereby the quantities and proportions of the at least one carbohydrate component, the at least one lipid component, and the at least one refined protein component are selected so as to provide a desired nutritional profile.

The dairy milk analogs provided herein may be used as a base for production of the other dairy product analogs with certain nutritional profiles. In some embodiments, such other dairy product analogs are yoghurt analogs. The methods for producing yoghurt analogs provided herein may comprise one or more of the following steps, in or out of order:

a) obtaining at least one carbohydrate component;

b) obtaining at least one lipid component;

c) obtaining at least one refined protein component from a non-animal natural and/or modified non-animal natural source;

d) blending the at least one carbohydrate, the at least one lipid, and the at least one refined protein component with an aqueous component to generate a mixture;

e) heating the mixture;

f) emulsifying at least a portion of the mixture to generate an emulsified mixture;

g) cooling the emulsified mixture;

h) adding fermenting microorganisms to the emulsified mixture to generate a fermentation mixture; and i) incubating the fermentation mixture at an elevated temperature until the fermentation mixture is set and acidified to provide the dairy yoghurt analog;

whereby the quantities and proportions of the at least one carbohydrate component, the at least one lipid component, and the at least one refined protein component are selected so as to provide a desired nutritional profile.

Examples of suitable fermenting microorganisms include, but are not limited to, *Lactobacillus bulgaricus* and *Streptococcus thermophilus*. The elevated temperature may be a temperature or temperature range that is suitable for the metabolic activity of the fermentating microorganisms, such as, for example, approximately 45° C.

In some embodiments, the dairy product analogs provided herein are combined with dairy products and/or other dairy product analogs. For example, the dairy milk analogs provided herein may be combined with dairy milk, seed milk (e.g., flax seed), nut milk (e.g., almond milk), or milks derived from cereals (e.g., rice milk).

Color-Neutral Refined Protein Components, Refined Protein Components and/or Refined Protein Isolates Certain embodiments are directed to color-neutral refined protein components obtained from non-animal natural and/or modified non-animal natural sources. Certain embodiments are directed to refined protein components or isolates obtained from non-animal natural and/or modified non-animal natural sources.

The exemplary embodiments disclosed herein may be used in a number of food application including but not limited dairy products, refined proteins as a supplement (powders, pastes for athletes, health), nutrition shakes/drinks, energy bars, meat substitutes, eggs substitutes (as ingredients in baking, formulations or as end consumer products like a scramble), spreads (savory or sweet), snack foods and/or salad dressings/condiments.

In some embodiments, the color-neutral refined protein component has a total protein content of at least about 10%, between about 10% and about 70%, between about 20% and about 60%, between about 30% and about 50%, between about 10% and about 30%, between about 10% and about 20%, or between about 12% and about 16% by weight.

In some embodiments, the refined protein component and/or refined protein isolate has a total protein content of at least about 10%, between about 10% and about 70%, between about 20% and about 60%, between about 30% and about 50%, between about 10% and about 30%, between about 10% and about 20%, or between about 12% and about 16% by weight It some embodiments, the color-neutral refined protein component has a total bound calcium content of between about 0.1% and about 2%, between about 0.3% and about 1.7%, between about 0.5% and about 1.5%, or between about 0.5% and about 1% by weight.

It some embodiments, the refined protein component and/or refined protein isolate has a total bound calcium content of between about 0.1% and about 2%, between about 0.3% and about 1.7%, between about 0.5% and about 1.5%, or between about 0.5% and about 1% by weight.

In some embodiments, the color-neutral refined protein component is a paste comprising between about 4% and about 25% by weight of protein, and between about 0.1 and about 1.5% by weight of calcium, and between about 50% and about 92% by weight of water. In some embodiments, the color-neutral refined protein component is a dry powder comprising between about 70% and about 90% by weight of protein, and between about 2% and about 7% by weight of calcium.

In some embodiments, the refined protein component and/or refined protein isolate is a paste comprising between about 4% and about 25% by weight of protein, and between about 0.1 and about 1.5% by weight of calcium, and between about 50% and about 92% by weight of water. In some embodiments, the color-neutral refined protein component is a dry powder comprising between about 70% and about 90% by weight of protein, and between about 2% and about 7% by weight of calcium.

One exemplary color-neutral refined protein component has a composition of at least about 80% of visible protein bands on a denaturing protein gel with a molecular weight of less than 200 kDa, at least about 80% of visible protein bands on a denaturing protein gel with a molecular weight of less than 150 kDa on a denaturing protein gel, at least about 80% of visible protein bands on a denaturing protein gel with a molecular weight of between about 50 kDa and about 100 kDa.

In some embodiments, the color-neutral refined protein component has a relative emulsion activity of between about 0.1 and about 2 relative to the emulsion activity of bovine serum albumin (BSA), whey, or rice protein controls, as determined by the method disclosed in Example 7.

In some embodiments, the refined protein component and/or refined protein isolate has a relative emulsion activity of between about 0.1 and about 2 relative to the emulsion activity of bovine serum albumin (BSA), whey, or rice protein controls, as determined by the method disclosed in Example 7.

In some embodiments, the color-neutral refined protein components comprise lower levels or fewer types of fatty acid oxidative breakdown products. Examples of fatty acid breakdown products include, but are not limited to, hexanal, nonanal, octanal, decanal, (E)-2-nonenal, (E,Z)-2,6-nonadienal, (E,E)-2,4-decadienal, and/or γ-nonalactone.

In some embodiments, the refined protein component and/or refined protein isolate comprise lower levels or fewer types of fatty acid oxidative breakdown products. Examples of fatty acid breakdown products include, but are not limited to, hexanal, nonanal, octanal, decanal, (E)-2-nonenal, (E,Z)-2,6-nonadienal, (E,E)-2,4-decadienal, and/or γ-nonalactone.

In some embodiments, the color-neutral refined protein components have an emulsification activity index at pH 7 of between about 25 m2/g and about 100 m2/g as determined by the method of Kinsella et al. (J. Agric. Food Chem., Vol. 26, No. 3, 1978).

In some embodiments, the refined protein component and/or refined protein isolate have an emulsification activity index at pH 7 of between about 25 m2/g and about 100 m2/g as determined by the method of Kinsella et al. (J. Agric. Food Chem., Vol. 26, No. 3, 1978).

The color-neutral refined protein components may be used in a convenient quantity to enable production of food products or to provide adequate protein fortification to food products. In liquid form, the color-neutral refined protein components may be used directly for the production of liquid food products. In powdered form, the color-neutral refined protein components may be blended with dried food products, optionally followed by reconstitution of the food products by dissolution in water; or added to other ingredients to produce a baked product for human consumption; or used as a protein supplement.

The refined protein component and/or refined protein isolate may be used in a convenient quantity to enable production of food products or to provide adequate protein fortification to food products. In liquid form, refined protein component and/or refined protein isolate may be used directly for the production of liquid food products. In powdered form, refined protein component and/or refined protein isolate may be blended with dried food products, optionally followed by reconstitution of the food products by dissolution in water; or added to other ingredients to produce a baked product for human consumption; or used as a protein supplement.

Certain embodiments are directed to a refined protein (isolate and/or component) that may have one or more of the following characteristics:

A refined protein comprising between 5% to 97%, 20% to 90%, 30% to 85%, or 40% to 80%, by weight of a protein obtained from one or more non-animal natural or modified non-animal natural sources. A refined protein comprising at least 5, 10, 20, 30, 40, 50 or 60% by weight of a protein obtained from one or more non-animal natural or modified non-animal natural sources.

A refined protein wherein the color is defined by an L* value of between 60 to 90, an a* value of between −6 to +6 and a b* value of between −20 to +20, an L* value of between 65 to 85, an a* value of between about −4 to about +4 and a b* value of between −18 to +18, an L* value of at least 65, an a* value of between at least −5 to +5 and a b* value of at least −16 to +16; or an L* value of at least 80, an a* value of between at least −3 and +3 and a b* value of at least −14 to +14.

In certain embodiments, the refined protein may be a paste, a wet suspension or a dry powder.

In certain embodiments, the refined protein may have a dry solids weight percentage of at least 5, 10, 15, 20, 25 or 30%.

In certain embodiments, the refined protein may have a calcium to protein ratio is between 0.5% w/w to 5% w/w, 1% w/w to 6% w/w, 3% w/w to 8% w/w, or 5% w/w to 10% w/w.

In certain embodiments, the refined protein may be color neutral or not color neutral.

In certain embodiments, the refined protein may have a pH of between 4.5 and 11, 6.5 and 10, 5.5 and 8, or 5.7 to 6.7. In certain embodiments, the refined protein may have a pH of at least 5. In certain embodiments, the refined protein may have a pH of less than 9.

In certain embodiments, the refined protein may have a moisture content of between 3% and 90% by weight. In certain embodiments, the refined protein may have has a moisture content of at least 4% by weight. In certain embodiments, the refined protein a moisture content of less than 80% by weight.

In certain embodiments, the refined protein may have a fat content of between 1% and 30% by weight. In certain embodiments, the refined protein may have a fat content of at least 2% by weight. In certain embodiments, the refined protein may have a fat content of less than 25% by weight.

In certain embodiments, the refined protein may have a carbohydrate content of between 0% and 50% by weight. In certain embodiments, the refined protein may have a carbohydrate content of at least 0% by weight. In certain embodiments, the refined protein may have a carbohydrate content of less than 25% by weight.

In certain embodiments, the refined protein has a starch content of between 0% and 10% by weight. In certain embodiments, the refined protein has a starch content of at least 3% by weight. In certain embodiments, the refined protein has a starch content of less than 9% by weight.

In certain embodiments, the refined protein has a phosphorus content of between 0% and 6% by weight. In certain embodiments, the refined protein has a phosphorus content of at least 0.1% by weight. In certain embodiments, the refined protein has a phosphorus content of less than 4% by weight.

In certain embodiments, the refined protein has sodium and/or potassium content of less than 0.5% by weight.

In certain embodiments, the refined protein has an ash content of between 0% and 20% by weight. In certain embodiments, the refined protein has an ash content of at least 1% by weight. In certain embodiments, the refined protein has an ash content of less than 10% by weight.

In certain embodiments, the refined protein has a reducing capacity of between 5% and 50%. In certain embodiments, the refined protein has a reducing capacity of at least 6%. In certain embodiments, the refined protein has a reducing capacity of less than 46%.

In certain embodiments, the refined protein has a total HPLC peak area for total extractable soluble sugars and organic acids of between 20,000 and 250,000. In certain embodiments, the refined protein has a total extractable soluble sugars and organic acids of at least 22,000. In certain embodiments, the refined protein has a total extractable soluble sugars and organic acids of less than 240,000

In certain embodiments, the refined protein has a total peak area measured by GC analysis of volatile compounds component of between 50,000 and 3,000,000. In certain embodiments, the refined protein has a volatile compounds component of less than 2,500,000

In certain embodiments, the refined protein has a isoflavones component of between 0% and 0.1% of dry mass. In certain embodiments, the refined protein has a isoflavones component of less than 0.075% of dry mass.

In certain embodiments, the refined protein has a tannins component of between 0% and 0.5% of dry mass. In certain embodiments, the refined protein has a tannins component of less than 0.3% of dry mass.

In certain embodiments, the refined protein has an instability index of between 0.2 and 0.6. In certain embodiments, the refined protein has an instability index of at least 0.22. In certain embodiments, the refined protein has an instability index of less than 0.57.

In certain embodiments, the refined protein has been produced in quantities of at least between 500-kg and 3000-kg, between 500-kg and 1000-kg, between 1000-kg and 2500-kg and between 1000-kg and 3500-kg.

Methods for Obtaining Refined Protein Components and/or Refined Protein Isolates Certain embodiments are directed to methods for obtaining color-neutral refined protein components from non-animal natural and/or modified non-animal natural sources. Certain embodiments are directed to methods for obtaining refined protein components and/or refined protein isolates from non-animal natural and/or modified non-animal natural sources.

Some of the advantages of the methods provided herein is that they may remove, or substantially remove, flavoring agents, aroma agents, coloring agents, other agents or combinations thereof from refined protein preparations, and thus make the refined protein preparations more suitable for use in food products. Removal of such agents may also increase the shelf life of food products comprising such color-neutral refined protein components, refined protein components and/or refined protein isolates.

The methods provided herein for obtaining color-neutral refined protein components from non-animal natural and/or modified non-animal natural sources may comprise one or more of the following steps, in or out of order:

a. obtaining a protein preparation from a non-animal natural and/or modified non-animal natural source;
b. washing the protein preparation at a wash pH;
c. extracting the protein preparation at an extraction pH to obtain an aqueous protein solution;
d. separating the aqueous protein solution from non-aqueous components;
e. adding salt;
f. precipitating the protein from the aqueous protein solution at a precipitation pH to obtain a protein precipitate;
g. separating the protein precipitate from non-precipitated components; and
h. washing the protein precipitate to obtain a color-neutral refined protein component.

The methods provided herein for obtaining the refined protein component and/or refined protein isolate from non-animal natural and/or modified non-animal natural sources may comprise one or more of the following steps, in or out of order:

a. obtaining a protein preparation from a non-animal natural and/or modified non-animal natural source;
b. washing the protein preparation at a wash pH;
c. extracting the protein preparation at an extraction pH to obtain an aqueous protein solution;
d. separating the aqueous protein solution from non-aqueous components;
e. adding salt;
f. precipitating the protein from the aqueous protein solution at a precipitation pH to obtain a protein precipitate;
g. separating the protein precipitate from non-precipitated components; and
h. washing the protein precipitate to obtain a refined protein component.

The refined protein preparation obtained from a natural source may have various forms, including, but not limited to, protein concentrate, protein isolate, protein flour, protein meal; native, denatured, or renatured protein; dried, spray dried, or not dried protein; enzymatically treated or untreated protein; and mixtures thereof. It may consist of particles of one or more sizes, and may be pure or mixed with other components (e.g., other plant source components). The refined protein preparation may be derived from non-animal natural and/or modified non-animal natural sources, or from multiple natural and/or modified natural sources. In some embodiments, the refined protein preparation is obtained from a plant. In some such embodiments, the plant is legume. In some such embodiments, the legume is pea. The pea may be whole pea or a component of pea, standard pea (i.e., non-genetically modified pea), commoditized pea, genetically modified pea, or combinations thereof. In some embodiments, the pea is *Pisum sativum*. In some embodiments, the legume is soy. The soy may be whole soy or a component of soy, standard soy (i.e., non-genetically modified soy), commoditized soy, genetically modified soy, or combinations thereof. In some embodiments, the legume is chickpea. The chickpea may be whole chickpea or a component of chickpea, standard chickpea (i.e., non-genetically modified chickpea), commoditized chickpea, genetically modified chickpea, or combinations thereof. In some embodiments, the refined protein preparation may be pre-treated for various purposes, such as, for example, extracting the protein preparation in a solvent to remove lipids, and heat treating the protein preparation to remove volatiles.

Washing the refined protein preparation may utilize various methods, including single wash, multiple washes, and/or counter-current washes.

The wash and extraction pH may be a pH that is suitable for washing and solubilizing proteins in a protein preparation. A suitable wash and extraction pH may be determined by testing various pH conditions, and identifying the pH condition at which the most optimal yield and quality (judged by, for example by one or more of the following: flavor, odor, color, nitrogen content, Ca content, heavy metal content, emulsification activity, MW distribution, and thermal properties of the protein component obtained) of the refined protein component is obtained. In some embodiments, the wash and extraction pH are alkaline pH. In some such embodiments, the alkaline pH is at about least 7.1, at least about 8, at least about 9, at least about 10, at least about 11, at least about 12, between about 7.1 and about 10, between about 8 and about 10, between about 9 and about 10, or between about 8 and about 9. In some such embodiments, the alkaline pH is about 8.5. In some embodiments, the wash and extraction pH are acidic pH. In some such embodiments, the acidic pH is less than 7, less than 6.95, less than 6.5, less than about 5, less than about 4, less than about 3, between about 2 and 6.95, between about 3 and about 6, or between about 3 and about 5. The extraction pH may be adjusted using a pH adjusting agent. In some embodiments, the pH adjusting agent is a food grade basic pH adjusting agent. In other embodiments, the pH adjusting agent is a food grade acidic pH adjusting agents. Examples of suitable acidic pH adjusting agents include, but are not limited to, acetic acid, hydrochloric acid, citric acid, succinic acid, and combinations thereof. Examples of suitable basic pH adjusting agents include, but are not limited to, potassium bicarbonate, sodium bicarbonate, sodium hydroxide, potassium hydroxide, calcium hydroxide, ethanolamine, calcium bicarbonate, calcium hydroxide, ferrous hydroxide, lime, calcium carbonate, trisodium phosphate, and combinations thereof. It is useful to obtain substantially as much extracted protein as is practicable so as to provide an overall high product yield. The yield of protein in the aqueous protein solution may vary widely, wherein typical yields range from about 1% to about 90%. The aqueous protein solution typically has a protein concentration of between about 1 g/L and about 300 g/L. The molecular weight distribution of the proteins comprised in the aqueous protein solution may vary widely.

Separating the aqueous protein solution from non-aqueous components may be accomplished by various methods, including but not limited to, centrifugation followed by decanting of the supernatant above the pellet, or centrifugation in a decanter centrifuge. The centrifugation may be followed by disc centrifugation and/or filtration (e.g., using activated carbon) to remove residual protein source material and/or other impurities. The separation step may be conducted at various temperatures within the range of about 1° C. to about 100° C. For example, the separation step may be conducted between about 10° C. and about 80° C., between about 15° C. and about 70° C., between about 20° C. and about 60° C., or between about 25° C. and about 45° C. The non-aqueous components may be re-extracted with fresh solute at the extraction pH, and the protein obtained upon clarification combined with the initial protein solution for further processing as described herein. The separated aqueous protein solution may be diluted or concentrated prior to further processing. Dilution is usually effected using water, although other diluents may be used. Concentration may be effected by membrane-based methods. In some embodiments, the diluted or concentrated aqueous protein solution comprises between about 1 g/L and about 300 g/L, between about 5 g/L and about 250 g/L, between about 10 g/L and about 200 g/L, between about 15 g/L and about 150 g/L, between about 20 g/L and about 100 g/L, or between about 30 g/L and about 70 g/L by weight of protein.

The protein in the aqueous protein solution may be optionally concentrated and/or separated from small, soluble molecules. Suitable methods for concentrating include, but are not limited to, diafiltration or hydrocyclone. Suitable methods for separation from small, soluble molecules include, but are not limited to, diafiltration.

Salt precipitation may be accomplished using various suitable salts and precipitation pHs. Suitable salts, salt concentrations, polysaccharides, polysaccharide concentrations, and precipitation pHs may be determined by testing various conditions, and identifying the salt and pH and polysaccharide condition at which are obtained the most colorless and/or flavorless protein precipitates at the most optimal yield and quality (judged by, for example, by one or more of the following: flavor, odor, color, nitrogen content, Ca content, heavy metal content, emulsification activity, MW distribution, and thermal properties of the protein component obtained). In some embodiments, salt precipitation occurs with calcium dichloride at a concentration of between about 5 mM and about 1,000 mM. Other examples of suitable salts include, but are not limited to, other alkaline earth metal or divalent salts (e.g., magnesium chloride, sodium chloride, calcium permanganate, and calcium nitrate). Typically, the precipitation pH is opposite the extraction pH (i.e., when the extraction pH is in the basic range, the precipitation pH is most suitable in the acidic range, and vice versa). In some embodiments, the precipitation pH is an acidic pH. In some such embodiments, the acidic pH is less than 7.1, less than about 6, less than about 5, less than about 4, less than about 3, less than about 2, between 6.9 and about 2, between about 6 and about 3, between about 6 and about 5, or between about 5 and about 4. In some such embodiments, the acidic pH is about 5.25. The precipitation pH may be adjusted using a pH adjusting agent. In some embodiments, the pH adjusting agent is a food grade acidic pH adjusting agent. In other embodiments, the pH adjusting agent is a food grade basic pH adjusting agent.

Separating the protein precipitate from non-precipitated components may occur by one or more of the methods disclosed herein.

Washing of the protein precipitate may occur by various methods. In some embodiments, the washing is carried out at the precipitation pH.

The protein precipitate may optionally be suspended. In some embodiments, the suspending is carried out at the extraction pH, for example, in the presence of a chelator to remove calcium ions. If the suspended protein preparation is not transparent it may be clarified by various convenient procedures such as filtration or centrifugation.

The pH of the suspended color-neutral refined protein component may be adjusted to a pH of between about 1 and about 14, between about 2 and about 12, between about 4 and about 10, or between about 5 and about 7, by the addition of a food grade basic pH adjusting agent, including, for example, sodium hydroxide, or food grade acidic pH adjusting agent, including, for example, hydrochloric acid or phosphoric acid.

The pH of the refined protein component and/or refined protein isolate may be adjusted to a pH of between about 1 and about 14, between about 2 and about 12, between about 4 and about 10, or between about 5 and about 7, by the addition of a food grade basic pH adjusting agent, including, for example, sodium hydroxide, or food grade acidic pH adjusting agent, including, for example, hydrochloric acid or phosphoric acid.

The color-neutral refined protein component may be dried. Drying may be performed in a suitable way, including, but not limited to, spray drying, dry mixing, agglomerating, freeze drying, microwave drying, drying with ethanol, evaporation, refractory window dehydration or combinations thereof.

The refined protein component and/or refined protein isolate may be dried. Drying may be performed in a suitable way, including, but not limited to, spray drying, dry mixing, agglomerating, freeze drying, microwave drying, drying with ethanol, evaporation, refractory window dehydration or combinations thereof.

Other optional steps in the methods provided herein are heating steps aimed at removing heat-labile contaminants and/or microbial contaminations, and additional filtering (e.g., carbon filtering) steps aimed at removing additional odor, flavor, and/or color compounds. In some embodiments, such additional filtering is carried out immediately after extracting the protein preparation or after separating the aqueous protein solution from the non-aqueous components.

In some embodiments, the methods provided herein provide a yield of protein of at least about 30%, at least about 40%, at least about 50%, at least about 60%, at least about 70%, at least about 80%, at least about 90%, between about 30% and about 90%%, between about 40% and about 90%%, between about 50% and about 90%, or between about 60% and about 90% by weight.

Non-Animal Natural and Modified Non-Animal Natural Sources

The protein, lipid, carbohydrate, or other ingredients of the dairy product analogs provided herein may be derived from one or more non-animal natural and modified non-animal natural sources.

The protein, lipid, carbohydrate, or other ingredients of the food product analogs provided herein may be derived from one or more non-animal natural and modified non-animal natural sources.

Suitable natural sources are naturally occurring plants, algae, fungi, or microbes.

Examples of suitable plants include, but are not limited to, caraway, coriander, cumin, fennel, parsley, dill, dandelion, helichrysum, marigold, mugwort, safflower, camomile, lettuce, wormwood, calendula, citronella, sages, thyme, chia seed, mustard, olive, coffee, capsicum, eggplant, paprika, cranberry, kiwi, vegetable plants (e.g., carrot, celery), tagetes, tansy, tarragon, sunflower, wintergreen, basil, hyssop, lavender, lemon verbena, marjoram, melissa, patchouli, pennyroyoal, peppermint, rosemary, sesame, spearmint, primroses, samara, pepper, pimento, potato, sweet potato, tomato, blueberry, nightshades, petunia, morning glory, lilac, jasmin, honeysuckle, snapdragon, psyllium, wormseed, buckwheat, amaranth, chard, quinoa, spinach, rhubarb, jojoba, cypselea, chlorella, marula, hazelnut, canola, kale, bok choy, rutabaga, frankincense, myrrh, elemi, hemp, pumpkin, squash, curcurbit, manioc, dalbergia, legume plants (e.g., alfalfa, lentils, beans, clovers, peas, lava coceira, frijole bola roja, frijole negro, lespedeza, licorice, lupin, mesquite, carob, soybean, peanut, tamarind, wisteria, cassia, chickpea, garbanzo, fenugreek, green pea, yellow pea, snow pea, yellow pea, lima bean, fava bean), geranium, flax, pomegranate, cotton, okra, neem, fig, mulberry, clove, eucalyptus, tea tree, niaouli, fruiting plants (e.g. apple, apricot, peach, plum, pear, nectarine), strawberry, blackberry, raspberry, cherry, prune, rose, tangerine, citrus (e.g., grapefruit, lemon, lime, orange, bitter orange, mandarin), mango, citrus bergamot, buchu, grape, broccoli, brussels, sprout, camelina, cauliflower, rape, rapeseed (canola), turnip, cabbage, cucumber, watermelon, honeydew melon, zucchini, birch, walnut, cassava, baobab, allspice, almond, breadfruit, sandalwood, macadamia, taro, tuberose, aloe vera, garlic, onion, shallot, vanilla, yucca, vetiver, galangal, barley, corn, curcuma aromatica, galangal, ginger, lemon grass, oat, palm, pineapple, rice, rye, sorghum, triticale, turmeric, yam, bamboo, barley, cajuput, canna, cardamom, maize, oat, wheat, cinnamon, sassafras, lindera benzoin, bay laurel, avocado, ylang-ylang, mace, nutmeg, moringa, horsetail, oregano, cilantro, chervil, chive, aggregate fruits, grain plants, herbal plants, leafy vegetables, non-grain legume plants, nut plants, succulent plants, land plants, water plants, delbergia, millets, drupes, schizocarps, flowering plants, non-flowering plants, cultured plants, wild plants, trees, shrubs, flowers, grasses, herbaceous plants, brushes, lianas, cacti, green algae, tropical plants, subtropical plants, temperate plants, derivatives and crosses thereof or combinations thereof. In certain embodiments, examples of suitable plants may be selected from one or more of the following: yellow peas, flaxseed, soy, sunflower, rapeseed, sugar cane, sugar beet, and corn.

Examples of suitable algae include, but are not limited to, viridiplantae, stramenopi les, rhodophyta, chlorophyta, PX, flordeophyceae, bangiophyceae, florideohpyceae, trebouxiophyceae, phaeophyceae, palmariales, gigartinales, bangiales, gigartinales, *Chlorella, Laminaria japonica, Laminaria saccharina, Laminaria digitata, Macrocystis pyrifera, Alaria marginata, Ascophyllum nodosum, Ecklonia* sp., *Palmaria palmata, Gloiopeltis furcata, Porphyra columbina, Gigartina skottsbergii, Gracilaria lichenoides, Chondrus crispus, Gigartina bursa-pastoris*, derivatives and crosses thereof or combinations thereof. In certain embodiments, examples of suitable algae may be selected from one or more of the following: *Schizochytrium* sp., *Chorella* sp., *Botryococcus hraunii*, and *Dunaliella tertiolecta*.

Examples of suitable fungi include but are not limited to *Candida etchellsii, Candida guilliermondii, Candida humilis, Candida utilis, Candida versatilis, Debaryomyces hansenii, Kluyveromyces lactis, Kluyveromyces marxianus, Kluyveromyces thermotolerans, Pichia pastoris, Rhodotorula* sp., *Saccharomyces bayanus, Saccharomyces beticus, Saccharomyces cerevisiae, Saccharomyces chevalieri, Saccharomyces diastaticus, Saccharomyces ellipsoideus, Saccharomyces exiguus, Saccharomyces florentinus, Saccharomyces pastorianus, Saccharomyces pombe, Saccharomyces sake, Saccharomyces uvarum, Sporidiobolus johnsonii, Sporidiobolus salmonicolor, Sporobolomyces roseus, Xanthophyllomyces dendrorhous, Yarrowia lipolytica, Zygosaccharomyces rouxii*, derivatives and crosses thereof or combinations thereof. In certain embodiments, examples of suitable fungi may be selected from one or more of the following: *Saccharomyces* sp., *Pichia pastoris, Hansunula polytnorpha, Aexula adeninivorans, Kluyveromyces lactis, Yarrowia lipolytica*, and *Schizosaccarotnyces pombe*.

Examples of suitable microbes include but are not limited to firmicutes, cyanobacteria (blue-green algae), bacilli, oscillatoriophcideae, bacillales, lactobacillales, oscillatoriales, bacillaceae, lactobacillaceae, arthrospira, *Bacillus coagulans, Lactobacillus acidophilus, Lactobacillus Reuteri, Spirulina, Arthrospira platensis, Arthrospira maxima*, derivatives and crosses thereof or combinations thereof. In certain embodiments, examples of suitable microbes may be selected from one or more of the following: *Escherichia coli, Lactobacillus* sp., and *Cornybacterium glutamicum*.

Non-animal natural sources may be obtained from a variety of sources including, but not limited to, nature (e.g., lakes, oceans, soils, rocks, gardens, forests, plants, animals), brewery stores, and commercial cell banks (e.g., ATCC, collaborative sources).

Modified non-animal natural sources may be obtained from a variety of sources including but not limited to brewery stores and commercial cell banks (e.g., ATCC, collaborative sources), or can be generated from natural sources by methods known in the art, including selection, mutation, or gene manipulation. Selection generally involves continuous multiplication and steady increase in dilution rates under selective pressure. Mutation generally involves selection after exposure to mutagenic agents. Gene manipulation generally involves genetic engineering (e.g., gene splicing, insertion of deletions or modifications by homologous recombination) of target genes. A modified natural source may produce a non-native protein, carbohydrate, lipid, or other compound, or produce a non-native amount of a native protein, carbohydrate, lipid, or other compound. In some embodiments, the modified natural source expresses higher or lower levels of a native protein or metabolic pathway compound. In other such embodiments, the modified natural source expresses one or more novel recombinant proteins, RNAs, or metabolic pathway components derived from another plant, algae, microbe, or fungus. In other embodiments, the modified natural source has an increased nutraceutical content compared to its native state. In yet other embodiments, the modified natural source has more favorable growth and production characteristics compared to its native state. In some such embodiments, the modified non-animal natural source has an increased specific growth rate compared to its native state. In other such embodiments, the modified non-animal natural source may utilize a different carbon source than its native state.

In some embodiments, the protein, lipid, carbohydrate, or other ingredients of the dairy product analogs and/or food product analogs provided herein are derived from byproducts of previously processed one or more non-animal natural or modified non-animal natural sources. Examples of such byproducts include, but are not limited to, deoiled meal (e.g., deoiled flaxseed meal, deoiled soybean meal, deoiled sunflower meal, deoiled canola meal, or combinations thereof).

Other Ingredients

In some embodiments, the dairy product analogs and/or food product analogs provided herein comprise other ingredients that improve one or more of the following: color, taste, and nutritional and other qualities. Examples of such other ingredients include, but are not limited to:

- antioxidants (e.g., rosemary, spearmint, ascorbic acid, sodium ascorbate, Maillard browning products [melanoidins], BHA, BHT, TBHQ, propyl gallate, tocopherols, vitamin A, vitamin E, carotenoids, flavonoids or combinations thereof; between about 0.01% and about 10%, between about about 0.05% and about 5%, or between about 0.1% and about 2% by weight);
- sweeteners (e.g., glucose, sucrose, fructose, dextrose, maltose, dextrin, maltodextrin, sucralose, levulose, tagatose, galactose, natural sweeteners [e.g., agave, cane juice, corn syrup, honey, maple syrup, stevia or other compounds extracted from stevia plant [e.g., rebiana-A, rebaudioside-A, reb-A]], sugarless sweeteners [e.g., sugar alcohols such as maltitol, xylitol, sorbitol, erythritol, mannitol, isomalt, lactitol, hydrogenated starch hydro lysates], artificial sweeteners [acesulfame K, aspartame, sucralose, saccharin, stevia, tagatose] or combinations thereof; natural sweetener content may be at least about 0.01%, between about 0.1% to about 20%, between about 0.1% and about 10%, or between about 1% to about 6% by weight; artificial sweetener content may be at least about 0.01%, between about 0.05% to about 5%, or between about 0.1% and about 1.0% by weight);
- vitamins (e.g., vitamin B12, vitamin D, vitamin C, vitamin A, vitamin E, vitamin B, vitamin K, thiamine, riboflavin, pyridoxine, carotenoids (e.g., beta-carotene, zeaxanthin, lutein, lycopene), niacin, folic acid, pantothenic acid, biotin, choline, inositol) or combinations thereof;
- emulsifiers (e.g., lecithin, carrageenan, cellulose gum, cellulose gel, starch, gum arabic, xanthan gum, mono- and diglycerides, propylene glycol monoesters, sodium stearoyl-2-lactylate, polsorbate 60, posylorbate 80, lecithin, hydroxylated lecithin, or combinations thereof; emulsifier content may be between about 0.01% and about 10%, between about 0.05% and about 5%, or between about 0.5% and about 2% by weight);
- stabilizing agents (e.g., starches, gums [e.g., xanthan gum, bean gum, gear gum, gum arabic, gum ghatti, gum karaya, gum tragacanth, gellan gum], hydrocolloids [e.g., guar, acacia, locust bean gum, xanthan, gellan, carrageenan, cellulose, carboxymethyl cellulose, microcrystalline cellulose, methylcellulose hydroxypropyl methyl cellulose, hydroxypropyl cellulose, pectin, low methoxyl pectin, gelatin, agar, furcellaran, dextran, or combinations thereof; between about 0.1% and about 5%, between about 0.5% and about 3%, between about 0.7% and about 1.5% by weight; enhance physical properties by imparting viscosity or mouthfeel properties, stabilize and/or suspend insoluble materials and prevent separation or settling of ingredients);
- preservatives (e.g., potassium sorbate, sorbic acid or combinations thereof);
- buffering agents that prevent undesired creaming or precipitation upon addition of the dairy milk analogs into hot, acidic environments (e.g. when added to a hot beverage such as coffee; e.g., monophosphates, diphosphates, sodium mono- and bicarbonates, potassium mono- and bicarbonates, potassium phosphate, dipotassium phosphate, potassium hydrophosphate, sodium bicarbonate, sodium citrate, sodium phosphate, disodium phosphate, sodium hydrophosphate, sodium tripolyphosphate or combinations thereof);
- probiotics;
- minerals (e.g., chloride, sodium, calcium, iron, chromium, copper, iodine, zinc, magnesium, manganese, molybdenum, phosphorus, potassium, selenium, aluminum, soluble mineral salts, slightly soluble mineral salts, insoluble mineral salts, chelated minerals, mineral complexes, non-reactive minerals such as carbonate minerals, reduced minerals, ammonium or combinations thereof);
- omega-3 fatty acids (e.g., docosahexanenoic acid [DHA]);
- antimicrobial agents;
- sterols;
- dietary fibers (e.g., soy cotyledon fiber [e.g., in an amount between about 0% and about 40%, between about 1% and about 20%, or between about 1.5% and about 5% by weight];
- amino acids (e.g., essential amino acids [e.g., arginine, cysteine, histidine, isoleucine, leucine, lysine, methionine, phenylalanine, 7threonine, tryptophan, tyrosine, valine], amino acid salts, amino acid chelates or combinations thereof);
- phospholipids;
- salts (e.g., sodium citrate, sodium chloride, potassium citrate, potassium phosphate, dipotassium phosphate or combinations thereo; for example to enhance flavor and/or buffering to enhance protein stability);
- pH-adjusting agents (e.g., organic pH adjusting agents, inorganic pH adjusting agents, food grade acids [e.g., acetic, lactic, hydrochloric, phosphoric, citric, tartaric, malic, glucono, deltalactone, gluconic acid], basic pH adjusting agent [e.g., disodium diphosphate, potassium hydroxide] or combinations thereof);
- binding agents (e.g., carrageenan, cellulose gum, cellulose gel, starch, maltodextrin, gum arabic, xanthan gum or combinations thereof; between about 0.01% and about 10%, between about 0.05% and about 5%, or between about 0.1% and about 2% by weight);
- prebiotics (e.g., fructooligosaccharides, galactooligosaccharides); and
- biotics (e.g., *Bifidobacterium* spp., *Clostridium* spp., *Bacteroides* spp. *Enterococcus faecalis, E. coli, Enterobacter cloacae, Klebsiella pneumoniae, Staphylococcus epidermidis, Staphylococcus haemolyticus*, Lactoferrin or combinations thereof).

The ingredients may be native to one or more non-animal natural sources; produced by one or more modified non-animal natural sources; produced by one or more non-animal natural sources or modified non-animal natural sources under controlled conditions, or produced synthetically.

Packaging, Labeling, Marketing, and Sale

The dairy product analogs and/or food product analogs provided herein may be packaged in containers. Examples of suitable containers include, but are not limited to, bags, cups, jars, tubs, bottles, bowls, boxes, cans, cartons, bags-in-boxes, tubes, capsules, vacuum packaging, pouches, Tetrapak, brick, gable top, liquid aseptic packaging, roll fed liquid aseptic packaging and single serve juice boxe, and the like and combinations thereof. The containers may be heat and/or light resistant. In some embodiments, the containers are pre-sterilized. The packaged dairy product analogs may be placed in refrigerated or frozen storage. In some embodiments, the flavor and texture of the dairy product analogs are substantially maintained after storing for at least 5 days. The packaging may carry one or more labels that communicate information to the consumer or that support the marketing of the food products. Example of information that may be communicated to the consumer include, but are not limited to, free of genetically modified organisms, free of gluten, Kosher, free of cholesterol, vegetarian, vegan, free of an allergen, free of soy, free of nuts or combinations thereof.

The dairy product analogs and/or food product analogs provided herein may be sold in various suitable venues. Such venues include, but are not limited to, grocery stores, convene stores, schools, vending machines, cafeterias, stadiums, food service providers, and direct to consumer outlets.

All references, including publications, patent applications, and patents, cited herein are hereby incorporated by reference to the same extent as if each reference were individually and specifically indicated to be incorporated by reference and/or were set forth in its entirety herein.

EXAMPLES

The following examples are included to demonstrate exemplary embodiments. It should be appreciated by those of skill in the art that the techniques disclosed in the examples that follow represent techniques discovered by the inventors to function well in the practice of the disclosed embodiments. However, those of skill in the art should, in light of the present disclosure, appreciate that many changes may be made in the specific embodiments that are disclosed and still obtain a like or similar result without departing from the spirit and scope of the disclosure, therefore the matter set forth or shown in the accompanying drawings is to be interpreted as illustrative and not in a limiting sense.

Example 1—Obtaining a Color-Neutral Refined Protein Component from Pea Protein Isolate Spray-dried Pea Protein Isolate (Now Sports Pea Protein powder, Bloomingdale, IL) was added to distilled water adjusted to pH 8.5 using 1N NaOH while stirring for 60 min to a final solids concentration of 100 g/L. The extract was separated by centrifuging at 5,000 to 15,000 g for 10 min. The supernatant was retained whereas the pellet was discarded. The supernatant was centrifuged again to clear it from solids. The pea protein was then precipitated by adding 500 mM $CaCl_2$ to a final concentration of 50 mM, and adjusting the pH to 5.25 using 1N HCl. The mixture was briefly mixed. When formed, the white precipitate was separated by centrifuging at 5,000 to 15,000 g for 10 min. The supernatant was discarded, and the precipitate was washed twice with water at pH 5.25 using 1N HCl (add acidified water to pellet for a final dilution of 25-50×(~1-2 mL solid pellet mixed in 50 mL acidified water; briefly mix up; centrifuge as above, repeat). Obtained protein yields were as follows: 7% by weight of extracted protein; 70% volume recovery of aqueous protein solution; 33-50% mass yield after salt precipitation; and 95% mass yield after acid wash. The color of the resulting protein paste was determined as described in Example 6; the protein paste had an L* value of 89.5, an a* value of 4.1, and a b* value of 9.6, and had a calcium to protein ratio of 6% w/w. The relative emulsion activity of the protein paste (Table 1) was determined as described in Example 7.

TABLE 1

Relative Emulsion Activity of Color-neutral Refined Pea Protein Component

|  | Average | Standard Deviation |
| --- | --- | --- |
| Sample A | 1.3 | 0.10 |
| Sample B | 0.7 | 0.16 |
| Sample C | 0.7 | 0.03 |

Example 2—Obtaining a Color-Neutral Refined Protein Component from Chickpea Flour Chickpea flour was made by grinding dry chickpeas to a 30-100 #mesh size using a hammer mill. The flour was added to distilled water adjusted to pH 8.5 using 1N NaOH while stirring for 60 min to a final solids concentration of 100 g/L. The extract was separated by centrifuging at 5,000 to 15,000 g for 10 min. The supernatant was retained whereas the pellet was discarded. The supernatant was filtered using tangential flow filtration with a membrane that had 100 kDa molecular weight cut-off. The retentate was retained while the filtrate was discarded. The chickpea protein was precipitated by adding 500 mM $CaCl_2$ to a final concentration of 50 mM, and adjusting the pH to 5.25 using 1N HCl. The mixture was briefly mixed. When formed, the white precipitate was separated by centrifuging at 5,000 to 15,000 g for 10 min. The supernatant was discarded, and the precipitate was washed twice with water at pH 5.25 using 1N HCl (add acidified water to pellet for a final dilution of 25-50×(~1-2 mL solid pellet mixed in 50 mL acidified water; briefly mix up; centrifuge as above, repeat). Obtained protein yields were as follows: 70% by weight of extracted protein; 70% volume recovery of aqueous protein solution; 33-50% mass yield after salt precipitation; and 95% mass yield after acid wash, and had a calcium:protein ratio of 5% w/w.

Example 3A—Obtaining a Color-Neutral Refined Protein Component from Pea Flour

Pea flour was made by grinding dry yellow peas (Giusto Specialty Foods, LLC) to a 100 #mesh size using a hammer mill. The flour was added to distilled water adjusted to pH 8.5 using 1N NaOH while stirring for 60 min to a final solids concentration of 100 g/L. The extract was separated by passing the slurry through a decanting centrifuge. The supernatant was retained whereas the pellet was discarded. The supernatant was filtered using tangential flow filtration with a membrane that had 100 kDa molecular weight cut-off. The retentate was retained while the filtrate was discarded. The protein was then precipitated by adding 500 mM $CaCl_2$) to a final concentration of 50 mM, and adjusting the pH to 5.25 using 1N HCl. The mixture was briefly mixed. When formed, the white precipitate was separated using a decanting centrifuge. The color of the resulting protein paste was determined as described in Example 6; the protein paste had an L value of 81.9, an a value of 4.4, and a b value of 12.5, and had a calcium:protein ratio of 7% w/w.

Example 3B—Obtaining a Refined Protein from Pea Flour

Pea flour was made by grinding dry yellow peas (Giusto Specialty Foods, LLC) to a 100 #mesh size using a hammer mill. 10 kg of flour was added to distilled water adjusted to pH 8.5 using 1N NaOH while stirring for 60 min to a final solids concentration of 100 g/L. The extract was separated by passing the slurry through a decanting centrifuge. The supernatant was retained whereas the pellet was discarded. The retentate was retained while the filtrate was discarded. The pea flour protein was then precipitated by adding $CaCl_2$) to a final concentration of 10 mM, and adjusting the pH to 4.5 using 6N HCl. The mixture was briefly mixed. When formed, the white precipitate was separated using a disk stack centrifuge. The supernatant was discarded, and the precipitate was washed with water titrated to pH 5.25 using 6N HCl. Obtained yields were as follows: 49% protein by weight extracted from the flour and 68% protein by weight precipitated from the aqueous extraction. This resulted in a final recovery of about 33% protein from the flour. The final mass of the refined protein isolate was 1.2 kg containing 53% protein mass % (mass/dry weight %). The color of an emulsion generated from the protein paste was determined as described in Example 8; it had an L* value of 76.2, an a* value of −1.73, and a b* value of 1.2.

Example 4—Producing a Dairy Milk Analog

A dairy milk analog was produced having the composition shown in Table 2.

TABLE 2

Composition of Dairy Milk Analog

| Ingredient | Supplier | % by weight |
| --- | --- | --- |
| Water, filtered | | 79.259 |
| Color-neutral refined protein component | see Example 1 | 15.76 |
| Evaporated cane juice | Florida Crystals (West Palm Beach, FL) | 2.37 |
| Sunflower oil (high heat) | Spectrum (Boulder, CO) | 1.61 |
| Flavoring agents (e.g., natural milk type flavor and natural butter type flavor) | Ed Long (Elk Grove Village, IL) | 0.44 |
| Lecithin (Giralec sunflower) | Austrade (Palm Beach Gardens, FL) | 0.11 |
| Gellan (Kelcogel HA-B) | CP Kelgo (Atlanta, GA) | 0.0413 |
| Cellulose gum (Cekol 10000) | CP Kelgo (Atlanta, GA) | 0.03 |
| Antifoaming agent (AFE-1510) | Xiameter, Dow Corning | 0.005 |
| Dipotassium phosphate | ICL (Tel Aviv, Israel) | 0.32 |
| Life's DHA | Martek (Parsippany, NJ) | 0.055 |
| Vitamin A Palmitate 250 | DSM (Heerlen, Netherlands) | 0.0024 |
| Vitamin D2 Fortitech | DSM (Heerlen, Netherlands) | 0.00012 |

Slight variations to this composition and different flavoring agents (e.g., natural sweetness enhancer flavor and natural chocolate type flavor, or natural *vanilla* flavor and *vanilla* extract) may be used to produce flavored dairy milk analogs (e.g., chocolate milk or *vanilla* milk, respectively).

Cellulose and gellan gum was combined with evaporated cane juice in a dry blend. Sunflower oil was combined with DHA and lecithin to obtain an oil blend. Antifoam was added to the water under high shear until dissolved, the color-neutral refined protein component was added, and the mixture was mixed for 3 minutes at <1300 rpm to obtain a liquid blend. Dipotassium phosphate was added to the liquid blend, and the blend was mixed for another minute. The dry blend, oil blend, mineral blend, and flavoring agents were all mixed into the liquid blend for 5 minutes at >1,400 rpm. The pH was recorded, and the blend was subjected to microthermics with in line homogenization (direct, 293F, 6.5 seconds, 2,500 psi). The resulting product was collected and cooled, before vitamins were added. The color of the resulting dairy milk analog was determined as described in Example 6; the dairy milk analog had an L* value of 75.9, an a* value of 0.2, and a b* value of 6.8, had a protein content of 8 g per 8 oz serving, and a sugar content of 6 g per 8 oz serving. The taste was assessed by a panel of human testers to be superior to commercial almond milk and soy milk samples.

Example 5—Production of a Dairy Yoghurt Analog

A dairy yoghurt analog base was produced having the composition shown in Table 3.

TABLE 3

Composition of Dairy Yoghurt Analog Base

| Ingredient | Supplier | % by weight |
| --- | --- | --- |
| Water, filtered | | 54.25 |
| Evaporated cane sugar | Florida Crystals (West Palm Beach, FL) | 6.5 |
| Color-neutral refined protein component | see Example 1 | 35 |
| Corn starch/pectin blend (Grindsted Yogurt 6760) | Danisco, DuPont | 3.2 |
| Sunflower oil | Spectrum (Boulder, CO) | 1 |
| Algal oil (S35-O300) | DSM (Heerlen, Netherlands) | 0.05 |

The corn starch/pectin blend was combined with the evaporated cane sugar. The color-neutral refined protein component was hydrated in 120° F. water under high shear for 5 minutes. The pH of the hydrated color-neutral refined protein component was adjusted to 7 with NaOH, before it was combined with the corn starch/pectin/sugar blend under high shear and allowed to hydrate for another 30 minutes. Sunflower oil was added to the mixture under shear, and the mixture was heated to 140° F. and constant stir and while covered with foil. The mixture was homogenized at 2,500 psi (500 psi 2nd stage, 2,000 psi 1st stage). Subsequently, heat was increased to 200-205° F. and held for 20 min while stirring was maintained using a heat-resistant spatula. Finally, the mixture was covered with foil and left to cool to under 105° F. To 3,785.41 g of this dairy yoghurt analog base was added 1 g of Yogurt starter Culture (Vivolac Soy 424), and the culture was incubated at 44° C. until a pH of 4.4-4.5 was reached. The resulting dairy yogurt analog was low in saturated fats compared to whole cow yoghurt and contained no cholesterol, but had similar protein content to unstrained whole cow yogurt.

Example 6—Method for Determining the Color of a Food Product

The color of a food product was determined using a Datacolor 45S portable spectrophotometer (Datacolor, Lawrenceville, NJ, USA) using illuminant D65 and a visual angle of 10 degrees. A reference tile was used for calibration, and the results were expressed using the CIELAB system (determining L*—lightness, a* (green/red), and b* (blue/yellow)). L*a*b values for a variety of dairy products were determined, and are listed in Table 4. This method or other acceptable methods for determining the color of food product analogs may also be used.

TABLE 4

L*a*b Values and Protein Contents of Commercially Available Dairy Products and Dairy Product Analogs

| Brand | Product | Product type | a | b | L | Protein Content (g/8 oz) |
|---|---|---|---|---|---|---|
| Blue Diamond | Original | Almond milk | −0.7 | 5.7 | 72.56 | 1 |
| Blue Diamond | Original | Almond milk | −0.66 | 5.8 | 73.04 | 1 |
| Blue Diamond | Original | Almond milk | −0.67 | 5.8 | 73.12 | 1 |
| Blue Diamond | Unsweetened | Almond milk | −0.7 | 5.3 | 74.4 | 1 |
| Blue Diamond | Unsweetened | Almond milk | −0.73 | 5.3 | 74.5 | 1 |
| Blue Diamond | Unsweetened | Almond milk | −0.7 | 5.3 | 75.12 | 1 |
| Cashew Dream | Original | Cashew milk | 0.11 | 7.3 | 67.34 | 0 |
| Cashew Dream | Original | Cashew milk | 0.07 | 7.4 | 67.55 | 0 |
| Cashew Dream | Original | Cashew milk | 0.08 | 7.4 | 67.93 | 0 |
| Coconut Dream | Original Enhanced | Coconut milk | −1.11 | 0.6 | 76.53 | 0 |
| Coconut Dream | Original Enhanced | Coconut milk | −1.08 | 0.7 | 76.73 | 0 |
| Coconut Dream | Original Enhanced | Coconut milk | −1.1 | 0.7 | 77.72 | 0 |
| Coconut Dream | Unsweetened | Coconut milk | −1.14 | −0.6 | 78.43 | 0 |
| Coconut Dream | Unsweetened | Coconut milk | −1.13 | −0.6 | 78.84 | 0 |
| Coconut Dream | Unsweetened | Coconut milk | −1.15 | −0.5 | 79.33 | 0 |
| Forager | Organic Original | Cashew milk | −0.05 | 7.1 | 72.18 | 1 |
| Forager | Organic Original | Cashew milk | 0 | 7.4 | 72.55 | 1 |
| Forager | Organic Original | Cashew milk | −0.02 | 7.6 | 73.09 | 1 |
| Living Apothecary | Classic | Almond milk | −0.82 | 7.7 | 77.26 | 1 |
| Living Apothecary | Classic | Almond milk | −0.77 | 7.9 | 77.73 | 1 |
| Living Apothecary | Classic | Almond milk | −0.78 | 7.9 | 78.28 | 1 |
| Pacific | Organic Original Unsweetened | Coconut milk | −1.4 | −1.2 | 70.7 | 0 |
| Pacific | Organic Original Unsweetened | Coconut milk | −1.39 | −1.1 | 70.78 | 0 |
| Pacific | Organic Original Unsweetened | Coconut milk | −1.41 | −1.2 | 71.36 | 0 |
| Pacific | Original | Hemp milk | 0.6 | 12.3 | 72.91 | 3 |
| Pacific | Original | Hemp milk | 0.69 | 12.5 | 73.08 | 3 |
| Pacific | Original | Hemp milk | 0.56 | 12.4 | 73.19 | 3 |
| Pacific | Organic Original Unsweetened | Soy milk | −0.95 | 11.3 | 76.91 | 9 |
| Pacific | Organic Original Unsweetened | Soy milk | −0.99 | 11.2 | 77.07 | 9 |
| Pacific | Organic Original Unsweetened | Soy milk | −0.98 | 11.3 | 77.66 | 9 |
| Rice Dream | Original | Rice milk | −2.47 | 0.6 | 69.12 | 1 |
| Rice Dream | Original | Rice milk | −2.5 | 0.6 | 69.22 | 1 |
| Rice Dream | Original | Rice milk | −2.5 | 0.6 | 69.57 | 1 |
| Silk | Original | Almond milk | −1.09 | 8.7 | 71.58 | 1 |
| Silk | Original | Almond milk | −1.08 | 8.7 | 71.58 | 1 |
| Silk | Original | Almond milk | −1.09 | 8.8 | 72.25 | 1 |
| Silk | Original | Soy Creamer | −0.09 | 8.1 | 80.96 | 0.7 |
| Silk | Original | Soy Creamer | −0.07 | 8.4 | 81.38 | 0.7 |
| Silk | Original | Soy Creamer | −0.08 | 8.5 | 82.53 | 0.7 |
| Silk | Original | Soy milk | −1.14 | 14.3 | 75.02 | 8 |
| Silk | Original | Soy milk | −1.14 | 14.4 | 75.11 | 8 |
| Silk | Original | Soy milk | −1.14 | 14.6 | 75.61 | 8 |
| Silk | Unsweetened | Soy milk | −1.49 | 14.4 | 75.15 | 7 |
| Silk | Unsweetened | Soy milk | −1.44 | 14.7 | 75.8 | 7 |
| Silk | Unsweetened | Soy milk | −1.43 | 14.8 | 75.8 | 7 |
| So Delicious | Unsweetened | Cashew milk | −0.8 | 3.3 | 77.42 | 0 |
| So Delicious | Unsweetened | Cashew milk | −0.76 | 3.5 | 77.53 | 0 |
| So Delicious | Unsweetened | Cashew milk | −0.78 | 3.5 | 77.63 | 0 |
| So Delicious | Original | Coconut milk | −1.56 | 1.0 | 73.51 | 0 |
| So Delicious | Original | Coconut milk | −1.49 | 1.3 | 73.94 | 0 |
| So Delicious | Original | Coconut milk | −1.5 | 1.1 | 75.24 | 0 |
| Suzie's | Unsweetened | Quinoa milk | −4.46 | 12.0 | 54.03 | 2 |
| Suzie's | Unsweetened | Quinoa milk | −4.46 | 11.9 | 54.45 | 2 |
| Suzie's | Unsweetened | Quinoa milk | −4.5 | 12.2 | 54.56 | 2 |

Example 7—Method for Determining the Relative Emulsion Activity of a Color-Neutral Refined Protein Component The color-neutral refined protein component was dissolved in 0.3M NaCl at 3.2% final protein concentration, and a 450 ul, aliquot of the solution was added to each of 3 microfuge tubes. A 0.3 M NaCl solution was used as the blank control, and a bovine serum albumin (BSA: A2153, Sigma Aldrich) solution in 0.3M NaCl at 3.2% final protein concentration was used as the BSA standard. To each microfuge tub, 50 uL of sunflower oil (Spectrum) was added, and emulsions were generated by vortexing on setting 10 for 15 minutes using a Genie Vortex and foam tube adapter. The tubes were then placed on a rack and the emulsions were left to settle for 10-15 min. A 20 uL aliquot of each emulsion (taken from the bottom of the tube below any visible foam) was added to 480 uL of a 0.1% SDS solution, and the mixture was mixed by pipetting up and down 3-times a volume of 300 uL. Each sample was serially diluted 1:2 and 1:4 in 0.1% SDS. Light absorption at 500 nm (A500) was measured for each sample using 200 uL aliquots in a 96-well clear polystyrene plate and a Biotek Synergy H1 plate reader (program shakes for 1 minute to remove residual bubbles). The corrected A500 was calculated according to the formula: Corrected A500=(A500 sample–A500 blank)×dilution factor. The relative emulsion activity was calculated by dividing the average Corrected A500 by the average Corrected A500 of the BSA standard.

Example 8—Methods for Isolation of the Refined Protein Component and/or Refined Protein Isolate from Various Flour and Protein Sources This example is directed to a process to generate refined protein isolates or refined protein component from a variety of plant protein sources. In this example, plant sources analyzed include both legumes and oilseeds. This examples illustrates and quantifies the removal of various compounds in the isolation process (for example, fat, carbohydrates, ions, and/or small molecules), and evaluates the isolated protein for characteristics such as color, taste, and functionality. The refined protein isolation or refined protein component process was effective at isolating clean refined protein in the nine plant sources tested, and removed a substantial portion of carbohydrates, ions (with the exception of Ca), and small molecules. The process results in a white protein, with a cleaner taste than comparable currently available commercial proteins. This example is non-limiting and the processing, functions and modifications both qualitatively and quantitatively may be applied to one or more of the other embodiments disclosed herein.

Plant Sources

Plant sources tested included Yellow pea (YPE), Garbanzo bean (GAR), Fava bean (FAV), White bean (WBF), Navy bean (NAV), Soybean (SOY), Sesame (SES), Almond (ALM), and Quinoa (QUI). The commercial sources of some of the proteins used are: Pea Protein Isolate S85F, (Roquette) source: Roquette; Purls Pea 870 (Purls), source: World Food Processing; Pea Protein Isolate 80 (Nutralliance), source: Nutralliance; and Soy protein isolate (Soy PI), source: Now Sports. The commercial sources of the bean flours and oil seed flours used are: Yellow pea flour (YPE), source: Ingredion 1102; Garbanzo bean flour (GAR), source: Bob's Red Mill; Fava bean flour (FAV), source: Bob's Red Mill; White bean flour (WBF), source: Bob's Red Mill; Navy bean flour (NAV), source: whole navy beans from Bob's Red Mill, ground to flour using a coffee grinder; Low fat soy flour (SOY), source Bob's Red Mill; Defatted sesame flour (SES), source: Sukrin; and Defatted almond flour (ALM), source: Sukrin.

Protein Isolation Process

Figure 1B:
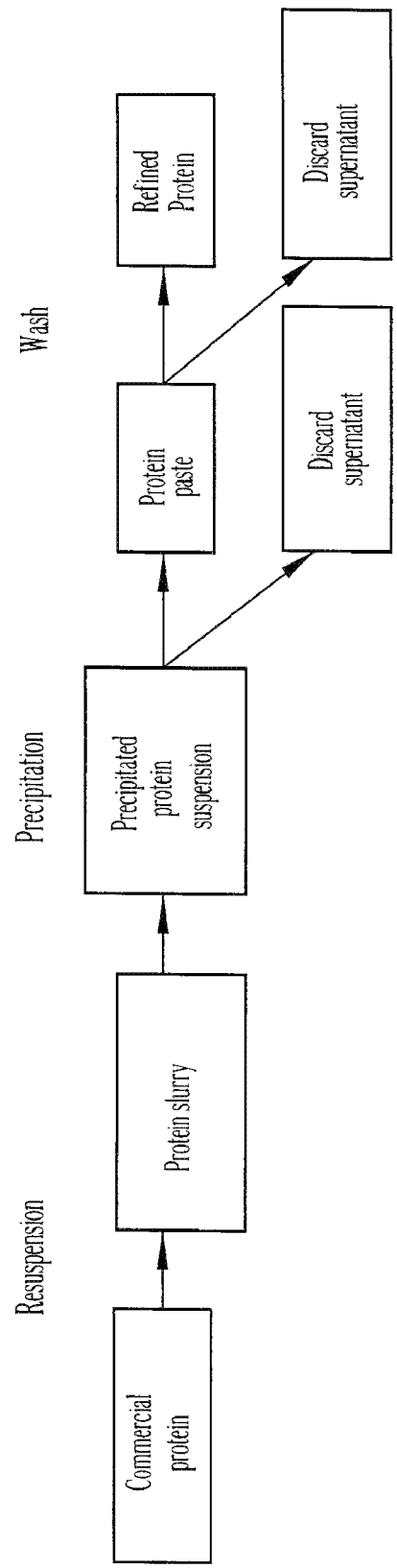

The refined protein isolation process begins with an aqueous extraction step in which the plant source is mixed with water at a determined optimal pH for extraction. The initial tests for determining an optimal pH for extraction to solubilize plant proteins are set forth in the present disclosure but other methods may be used for determining an optimal pH. It is to be understood that there may be one or more optimal pHs and/or one or more pH ranges that may be used in the embodiments disclosed herein. The aqueous phase is separated from the solids (starch/fiber) using centrifugation. The soluble proteins are then precipitated using a combination of heat (60 C), acid (pH drop to 5.5), and $CaCl_2$ addition (added to a ratio of 0.1 g $CaCl_2$ tog protein). The precipitated proteins are separated by centrifugation and the isolated protein is washed by mixing with tap water (30× dilution by weight) and centrifuged again. The material from this final step is referred to as a refined protein isolate and is analyzed as described below. An overview of the process with respect to flour type or protein isolate starting materials is set forth in FIG. 1A. FIG. 1A diagrams the steps used in the protein isolation process used to produce useful refined protein isolates and/or refined protein components for one or more of the embodiments of the follow disclosure. The samples were prepared in duplicate following the procedures set forth herein and certain process parameters (for example, pH, temp, and centrifuging speed) were kept constant or substantially constant; however, a range for these parameters has been demonstrated to be effective. In some embodiments the initial extraction step is bypassed as overviewed in FIG. 1B.

In this example, the exemplary bench procedure used to create the refined protein isolates from commercial protein isolate (overview in FIG. 1B) has the following steps:
1. 12% loading of PPI by weight (90 g of PPI raised to 750 g with tap water)
2. Mix on stir plate until fully mixed.
3. Raise the pH to 9 with 6N NaOH and mix for about 5 min
4. Add $CaCl_2$ 4M to achieve a concentration of 30 mM $CaCl_2$
5. Adjust the pH to 4.6 with 6N HCl
6. Spin down for about 5 min at 3500 rpm (2,200 g). Discard the supernatant.
7. Wash the pellet with about 15× water by weight.
8. Spin for about 5 min at 3500 rpm and discard supernatant. The pellet is the final product.

In this example, the bench procedure used to extract the refined protein isolates from flours consists of the following steps:
1. If the alternative source is a whole grain, grind it with the coffee grinder or the mill.
2. 10% loading of flour (by weight, 250 g of flour and add water up to 2500 g).
3. Mix on stir plate until fully mixed.
4. Adjust pH to 7 or 9 (use pH 7 for beans and pH 9 for oil seeds, see extraction pH optimization) using 6N NaOH.
5. Spin down at 5000 rpm for about 5 min to separate out. Collect supernatant (extract). Discard solids.
6. If particles are still visible, run this supernatant through another spin at 5000 rpm for about 5 min. Filter with metal mesh if necessary.
7. For sources with high fat content, a layer of fat may be separated at this step. Pour the extract carefully to avoid the fat layer.

It is to be understood that this example was for bench preparations and variation of one or more steps and/or parameters may be made in order to produce such useful refined protein isolates and/or refined protein components for larger or commercial quantities of the useful refined protein isolates and/or refined protein components. These procedures set forth in this example are exemplary and other appropriate procedures may be used both for bench and for commercial methods for obtaining the refined protein isolates and/or refined protein components of the present disclosure.

Thereafter, the samples in this example were subject to an examplary $CaCl_2$ Protein Precipitation process involving the following steps:
1. Heat the extract in a water bath at about 63° C., until extract temperature reaches 60° C.
2. Based on protein concentration, calculate the amount of $CaCl_2$ 4M to add to obtain a final ratio of 0.10 g $CaCl_2$/g protein.

3. Add corresponding volume of $CaCl_2$ 4M and adjust pH to 5.5 (using 6N HCL) to precipitate out the protein.
4. Spin at 5000 rpm (4650 g) about 5 min.
5. Pour off and discard supernatant and collect protein paste.

Thereafter, the samples in this example were subjected to an examplary wash process involving the following steps:
1. Re-suspend the protein paste in 30× volume of ater (by weight), mix for 15 seconds with stick homogenizer, adjust pH to 5.5.
2. Spin down at 4000 rpm (2970 g) for about 5 min.
3. Pour off supernatant and collect protein paste. This is the final refined protein isolate Optimization of Protein Extraction Conditions for Each Source In this example, the extraction pH was optimized for each source. In general, for beans, pH 7 is a good compromise between good protein extraction yield and low extraction of other compounds (based at least in part on extract color observation). For oil seeds, pH 9 has the greatest yield. The extraction pH used in the flour process at the bench was 7 for beans and 9 for oil seeds. FIG. 2 shows the percentage protein extracted from the 8 flour/protein isolate sources at increasing pH values.

Yields

Figure 3:
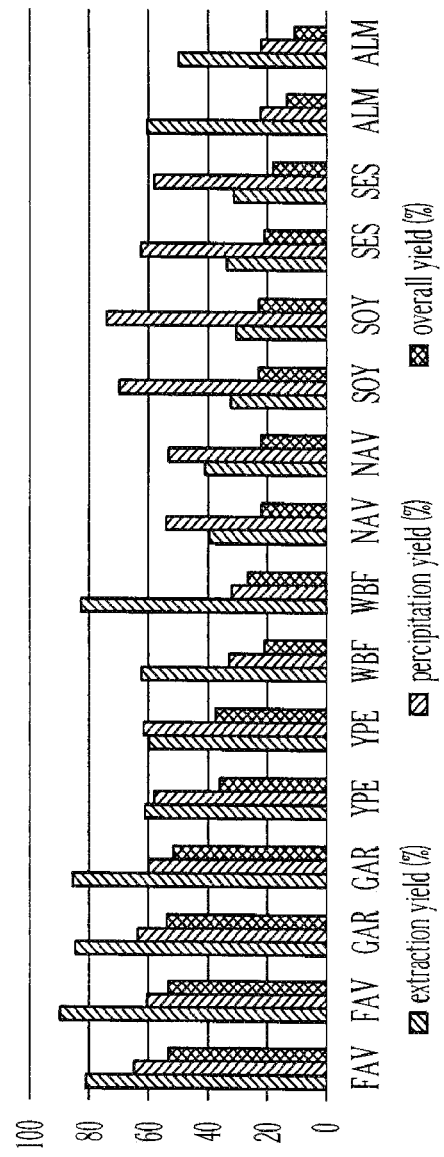
FIG. 3 shows the percent yield (wt/wt) at the extraction, precipitation and overall step for the eight sources tested, according to certain embodiments.

The process was run in duplicate on eight flour/protein isolate sources using the processes described herein. The process was effective on the sources tested. The percentage protein solubilized and extracted from the flour (extraction yield %) varied from 31-85% among the different sources, while the percentage of soluble protein precipitated from the extract (precipitation yield %) ranged from 21-71%. Overall yield from the flour to protein isolate (overall yield %) ranged from 12-53%. Yield values were similar between the two duplicates for each source. The final percent protein in the paste varied from 7-20% by weight depending on the plant source. FIG. 3 shows the % yield by weight (extraction, precipitation, overall) at each step for the eight sources tested in duplicate. Table 5 shows the test results for the protein isolation process using the eight different plant sources. Yield in the process at each step, protein extraction from flour (extraction yield), protein precipitated from the aqueous protein extraction (precipitation yield), and the total yield from the process (overall yield). The amount of protein in the final paste varies by plant source.

TABLE 5

| | Extraction yield (% by wt) | Precipitation yield (% by wt) | Overall yield (% by wt) | Protein in final paste (% by wt) |
|---|---|---|---|---|
| Yellow pea | 86 | 62 | 54 | 19 |
| Garbanzo bean | 85 | 62 | 52 | 17 |
| Fava bean | 61 | 60 | 36 | 16 |
| White bean | 73 | 32 | 24 | 6.8 |
| Navy bean | 40 | 53 | 22 | 7.1 |
| Soy | 31 | 72 | 22 | 19 |
| Sesame | 32 | 60 | 19 | 20 |

TABLE 5-continued

| | Extraction yield (% by wt) | Precipitation yield (% by wt) | Overall yield (% by wt) | Protein in final paste (% by wt) |
|---|---|---|---|---|
| Almond | 55 | 22 | 12 | 16 |
| Range | 31-85 | 22-72 | 12-53 | 7-20 |

Refined Protein Macro and Micronutrients

Figure 4:
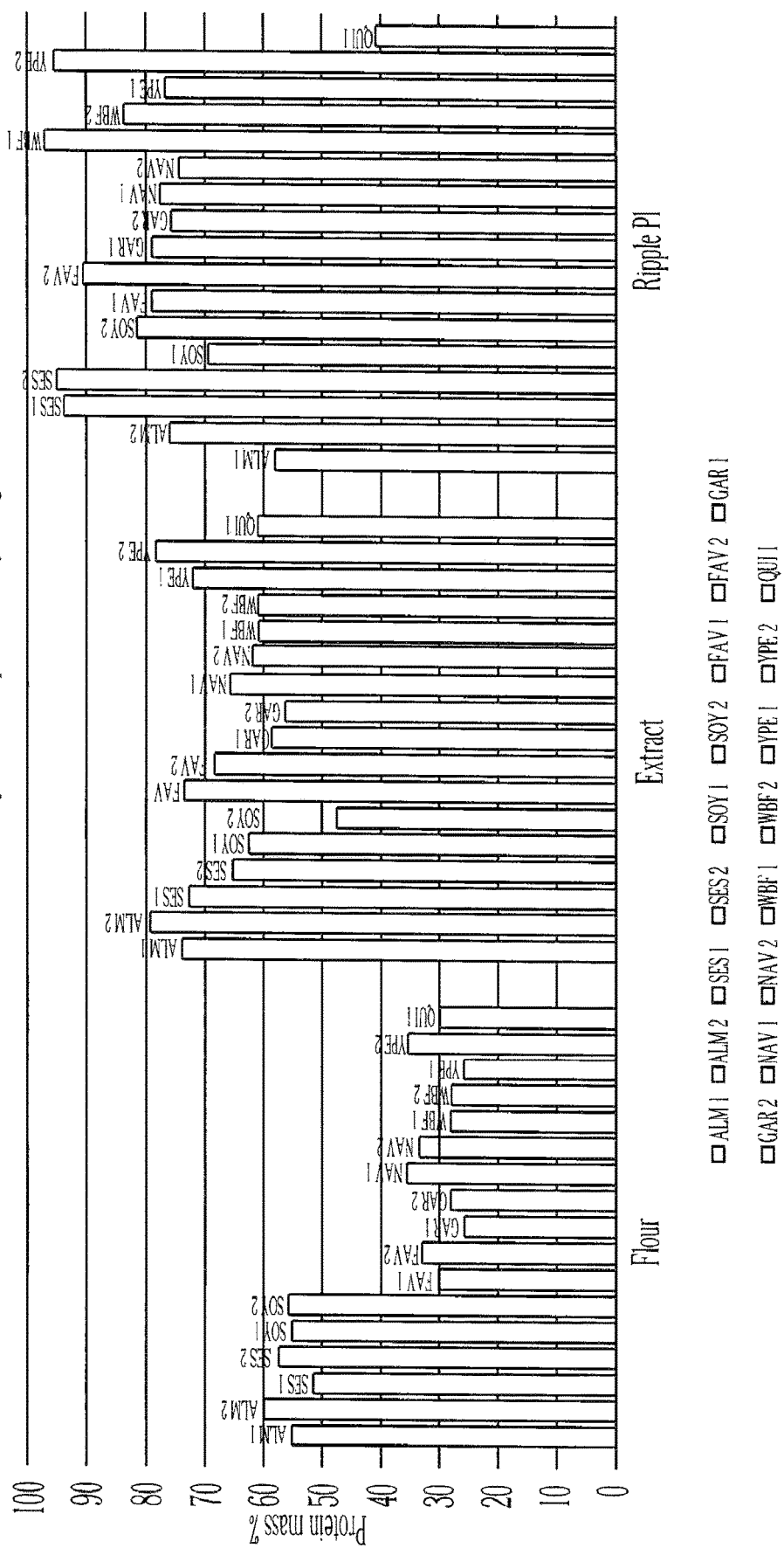
FIG. 4 shows the percent protein (protein weight/sample dry weight) generally increases from the starting commercial flour/protein isolate to final refined protein isolate for the feedstocks processed, according to certain embodiments.
Figure 5:
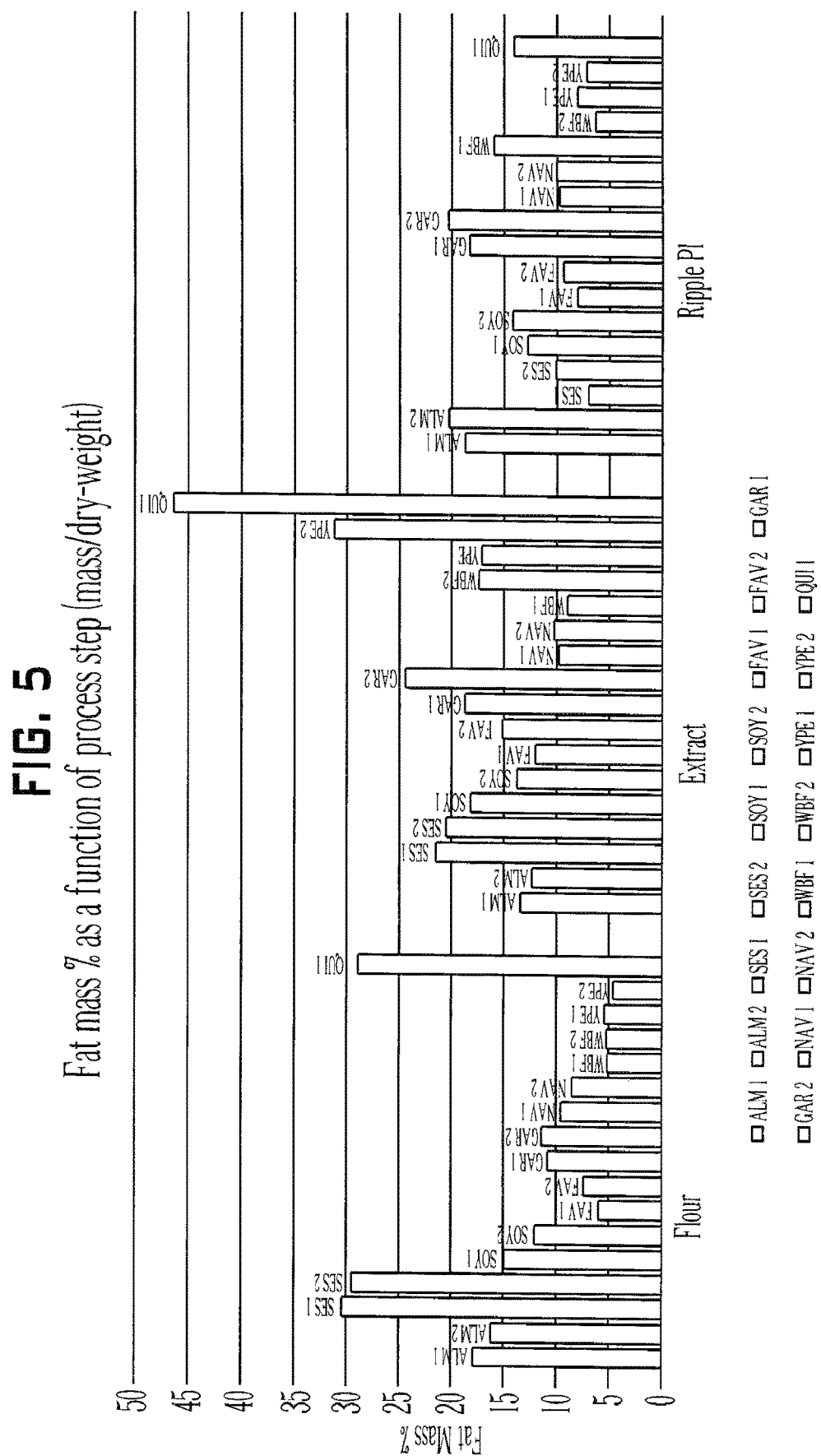
FIG. 5 shows the fat levels are in general slightly enriched in the process, according to certain embodiments.
Figure 6:
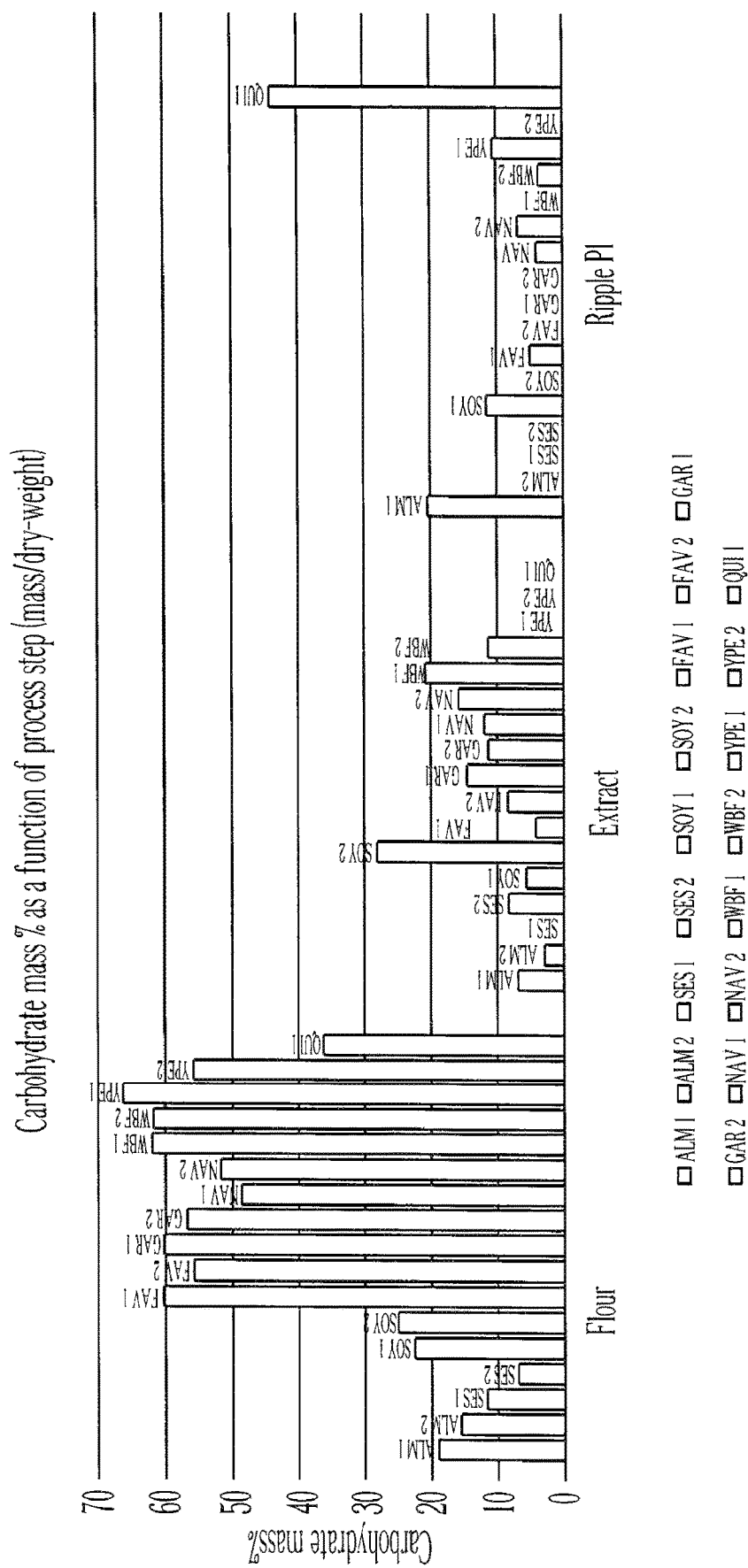
FIG. 6 shows the carbohydrate mass percentage as a function of the process step (mass/dry-weight), according to certain embodiments.

The following discussion shows results for protein, fat, carbohydrate and starch content as a function of the process step with respect to this exemplary. As discussed in the process description section, the starting raw materials were commercial flours/protein isolates made from various legumes, oil-seeds (defatted) or grains. The commercial flours/protein isolates then were processed through an aqueous extraction and the resulting supernatant was treated with $CaCl_2$ and acid to coagulate an insoluble fraction that was collected and analyzed. In general, the results show that in the final recovered, insoluble fraction (the exemplary refined protein isolates) protein content was substantially enriched, fats were slightly enriched and carbohydrates were reduced. FIG. 4 shows the % protein (protein weight/sample dry weight) generally increases from the starting commercial flour/protein isolate to final protein isolate for the feedstocks processed and tested. The values are comparable to the protein values of commercial PI (measured by combustion using a LECO nitrogen analyzer). FIG. 5 shows the fat levels are in general slightly enriched in the process but note that since the protein increases, the ratio fat to protein is reduced in the final Protein isolates (fat measured using AOAC 933.05). FIG. 6: shows the carbohydrate mass percentage as a function of the process step (mass/dry-weight). In some cases carbohydrates in the final product (final refined protein isolate) was not detectable. The oil seed defatted flours have lower carbohydrates as compared to the legume flours.

Figure 7:
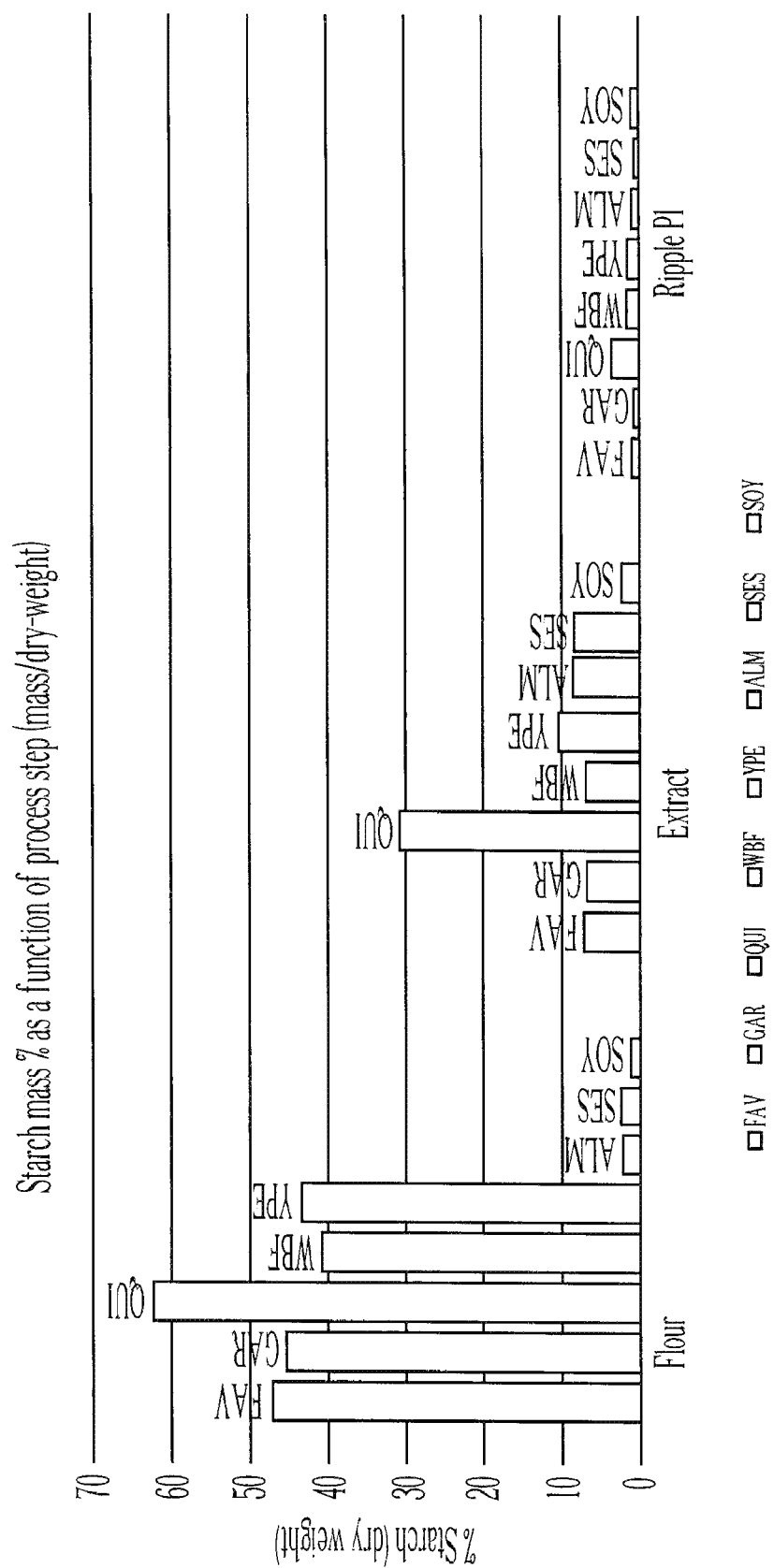
FIG. 7 shows the starch mass percentage as a function of the process step (mass/dry-weight), according to certain embodiments.

FIG. 7 shows the starch mass percentage as a function of the process step (mass/dry-weight). Starch reduction from flour sources (here using quinoa instead of navy bean) is between 43 and 99% from flour to the final protein isolate. Again, the oil seed flours have very low starch levels. With respect to the starch assay method used in this example, each sample was enzymatically digested (α-amylase (Sigma-Aldrich, AA306], amyloglucosidase (Sigma-Aldrich, A7095). An undigested sample is treated identically as a control. Post-incubation the samples are vortexed and the supernatant run on organic acids HPLC. The glucose in the undigested sample is subtracted from the glucose value in the digested sample. Net glucose concentration by weight is back-calculated to determine the original digested starch present in the sample. HPLC was performed on an Agilent 1200 HPLC instrument with a 1260 RID module. The analytical column is an Aminex 87-H column (Bio-rad, Hercules, CA] with a Micro-Guard Cation H Cartridge (Bio-Rad). Running buffer is 5 mM sulfuric acid at a 0.6 mL/min flow rate. Injection volume of sample supernatant is 10 uL. Refractive index signal is observed for 30 minutes. Peak areas are compared to an embedded five-point calibration up to 30 g/kg for the analytes.

Table 6 is a summary of mass % (mass/dry weight) data for protein, carbohydrate, fat, and starch for each replicate of each plant source tested:

| | Protein (mass %) | | | Fat (mass %) | | | Carbohydrates (mass %) | | | Starch (mass %) | | |
|---|---|---|---|---|---|---|---|---|---|---|---|---|
| | Flour | Extract | Refined PI | Flour | Extract | Refined PI | Flour | Extract | Refined PI | Flour | Extract | Refined PI |
| ALM 1 | 55 | 74 | 58 | 18 | 13 | 19 | 19 | 7 | 20 | 2.3 | 8.5 | 0.95 |
| ALM 2 | 60 | 79 | 76 | 16 | 12 | 20 | 16 | 3 | ND | | | |

-continued

| | Protein (mass %) | | | Fat (mass %) | | | Carbohydrates (mass %) | | | Starch (mass %) | | |
|---|---|---|---|---|---|---|---|---|---|---|---|---|
| | Flour | Extract | Refined PI | Flour | Extract | Refined PI | Flour | Extract | Refined PI | Flour | Extract | Refined PI |
| SES 1 | 52 | 73 | 94 | 30 | 21 | 7 | 12 | ND | ND | 2.5 | 8.3 | 0.54 |
| SES 2 | 57 | 65 | 95 | 29 | 20 | 10 | 7 | 8 | ND | | | |
| SOY 1 | 55 | 63 | 69 | 15 | 18 | 13 | 23 | 6 | 12 | 1.1 | 2.3 | 0.97 |
| SOY 2 | 56 | 47 | 82 | 12 | 14 | 14 | 25 | 28 | ND | | | |
| FAV 1 | 30 | 74 | 79 | 6 | 12 | 8 | 60 | 4 | 5 | 47 | 7.2 | 0.91 |
| FAV 2 | 33 | 68 | 91 | 7 | 15 | 9 | 56 | 8 | ND | | | |
| GAR 1 | 26 | 59 | 79 | 11 | 19 | 18 | 60 | 15 | ND | 45 | 6.8 | 0.67 |
| GAR 2 | 28 | 56 | 76 | 11 | 24 | 20 | 57 | 11 | ND | | | |
| NAV 1 | 36 | 66 | 78 | 10 | 10 | 10 | 49 | 12 | 4 | | | |
| NAV 2 | 33 | 62 | 74 | 8 | 10 | 10 | 52 | 16 | 7 | | | |
| WBF 1 | 28 | 61 | 97 | 5 | 9 | 16 | 62 | 21 | ND | 41 | 6.9 | 1.7 |
| WBF 2 | 28 | 61 | 84 | 5 | 17 | 6 | 62 | 11 | 4 | | | |
| YPE 1 | 26 | 72 | 77 | 5 | 17 | 8 | 66 | ND | 11 | 43 | 10 | 1.6 |
| YPE 2 | 35 | 78 | 96 | 5 | 31 | 7 | 56 | ND | ND | | | |
| QUI 1 | 30 | 61 | 41 | 29 | 46 | 14 | 36 | ND | 44 | 62 | 31 | 3.5 |

Ions (Ca, P, Na, K, Cl, Ash)

Figure 8:
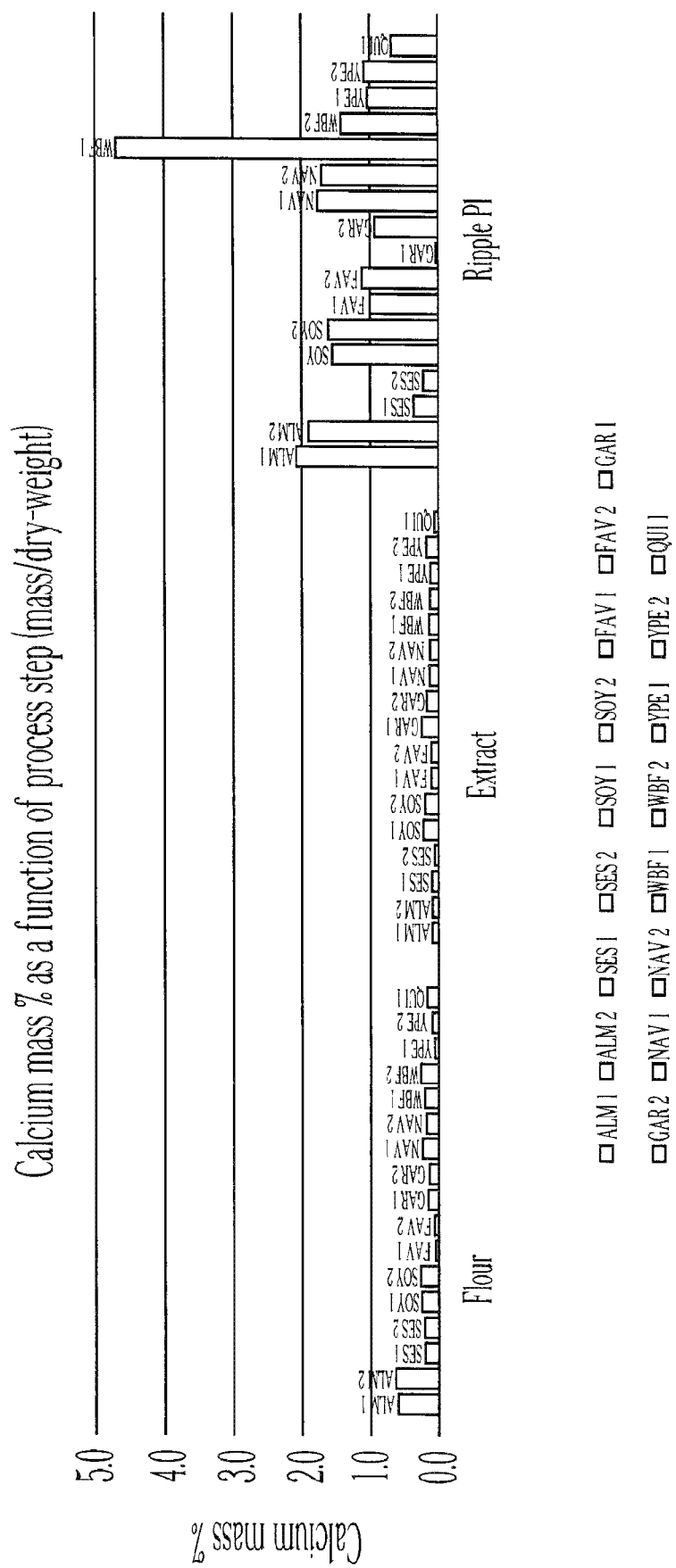
FIG. 8 shows the calcium mass % increases in the process due to Ca ions complexing with the refined protein, according to certain embodiments.
Figure 9:
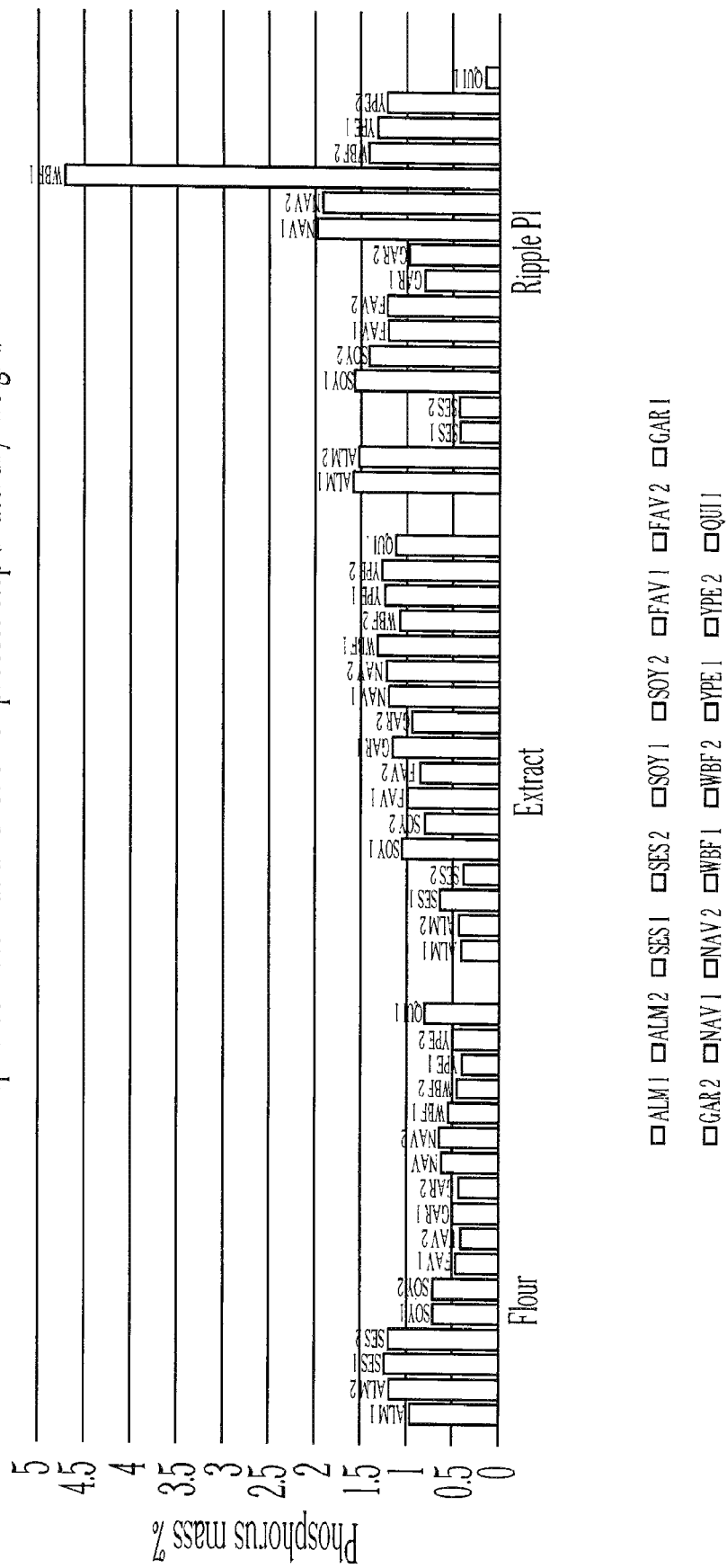
FIG. 9 shows the phosphorus content is slightly enriched in the refined protein, according to certain embodiments.
Figure 10:
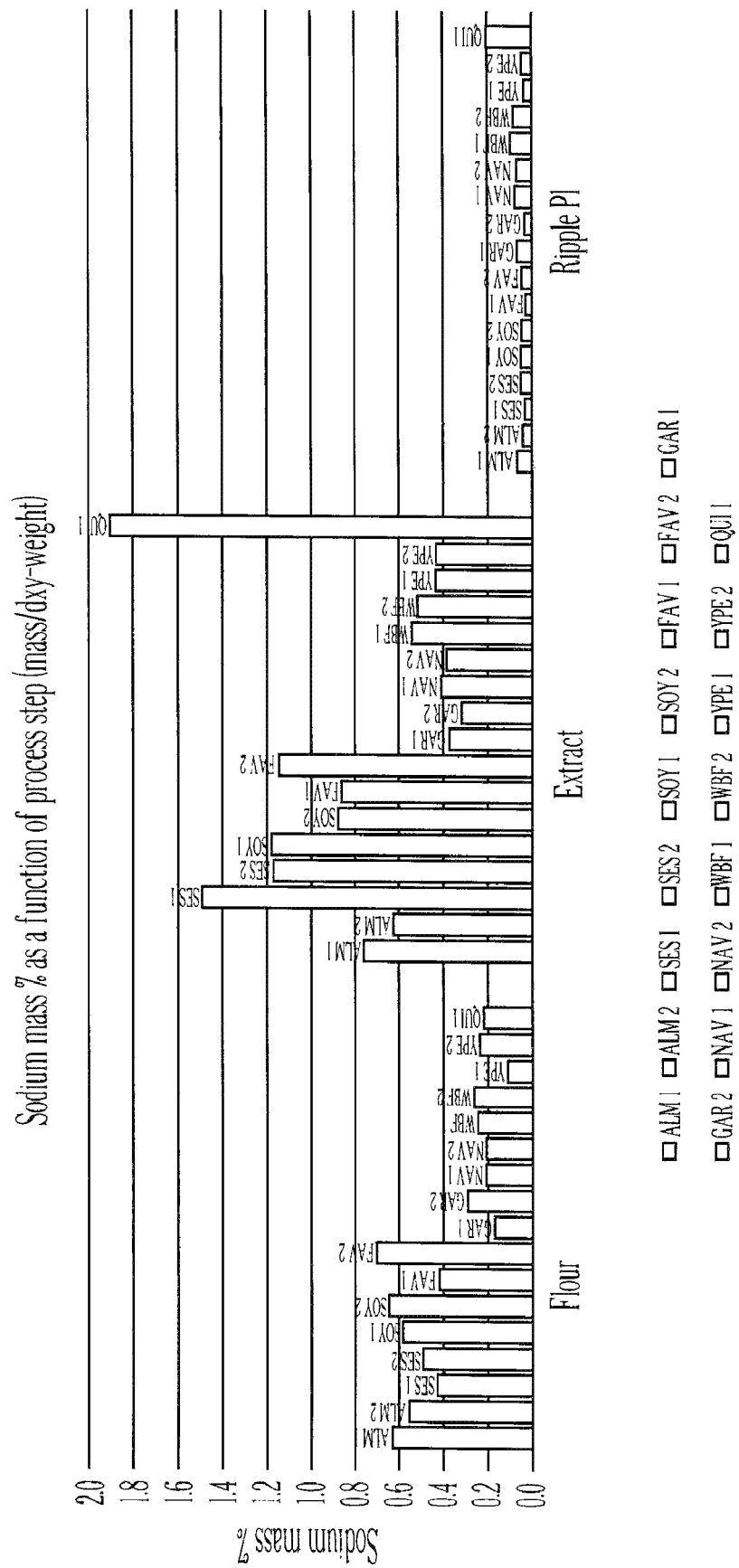
FIG. 10 shows that sodium is generally removed or substantially reduced during the process, according to certain embodiments.
Figure 11:
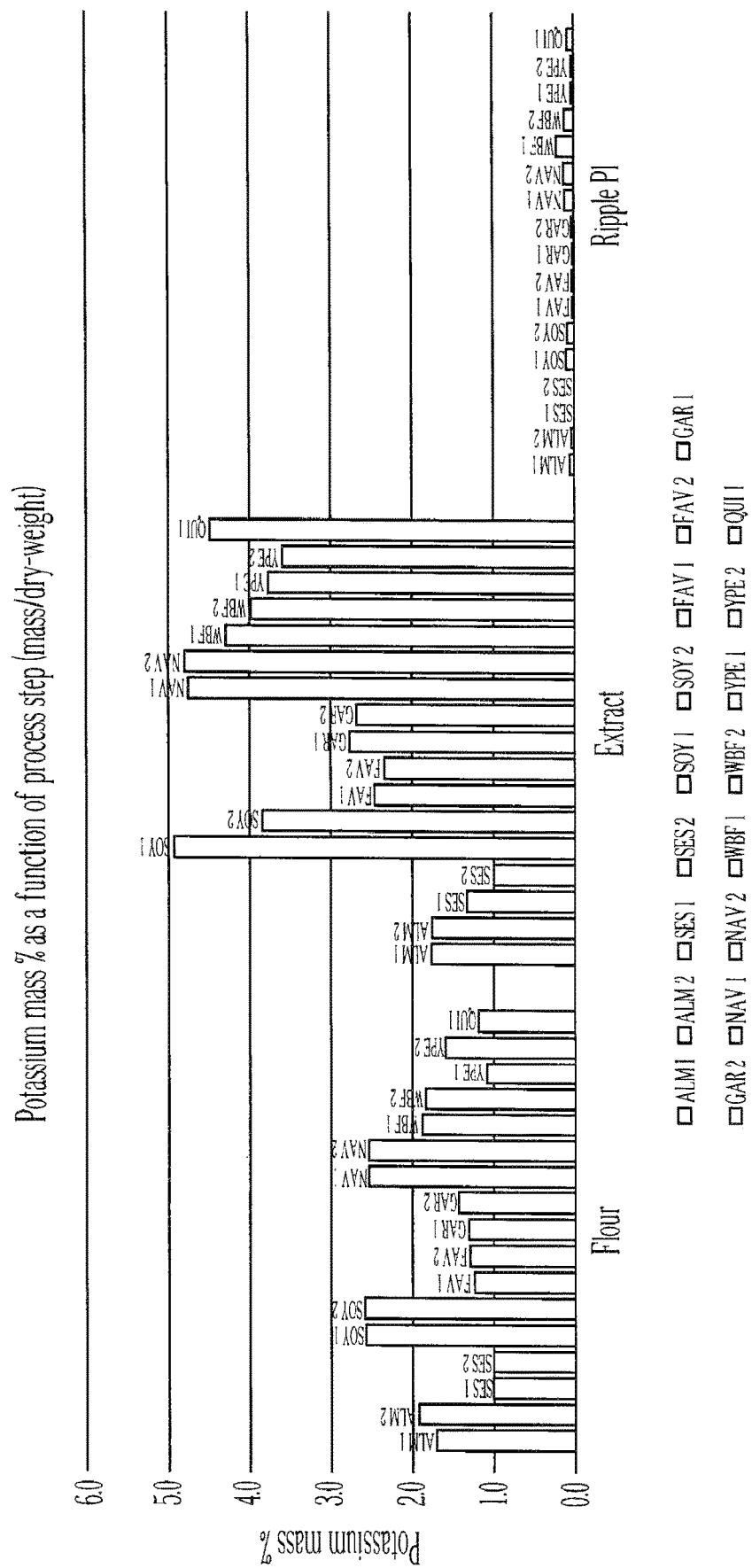
FIG. 11 shows that potassium is generally removed or substantially reduced during the process, according to certain embodiments.
Figure 12:
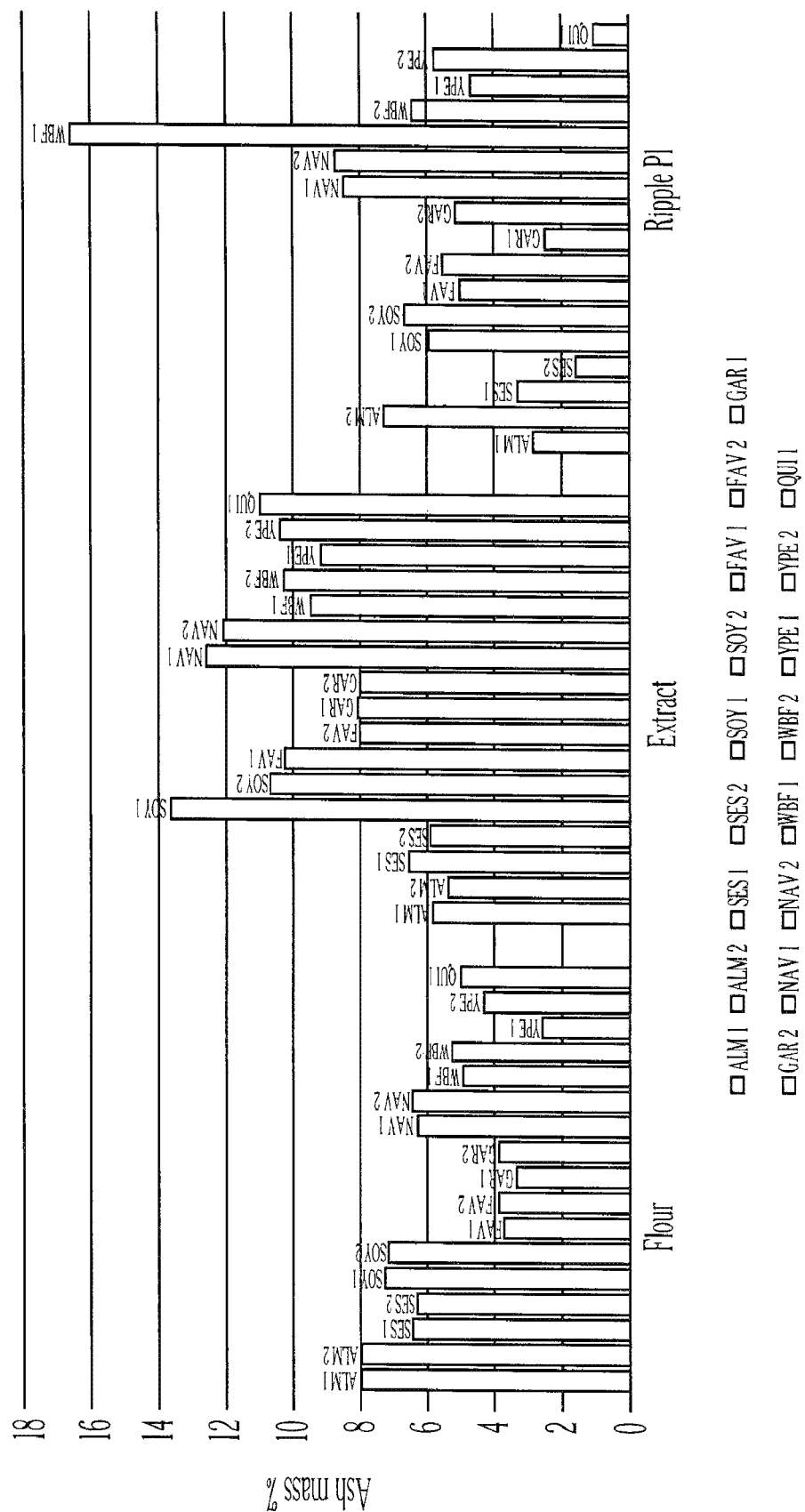
FIG. 12 shows ash content, according to certain embodiments.

Several ions that may impact taste or nutritional content were measured in the process. In general, the calcium content increased significantly during the process, which is by design. We use calcium salts to coagulate the protein and the Ca++ ion becomes complexed to the protein fraction and remains at the end of the process. FIG. 8 shows the calcium mass % (mass/dry weight) increases in the process due to Ca ions complexing with the protein (measured using AOAC 984.27). Phosphorus is slightly enriched. FIG. 9 shows the phosphorus content is slightly enriched in the final refined protein isolate (measured using AOAC 984.27). Sodium and potassium ions are substantially washed out of the final refined protein isolate by at least in part due to the purification process. FIG. 10 shows that sodium is generally removed or substantially reduced during the process (measured using AOAC 984.27). FIG. 11 shows that potassium is generally removed or substantially reduced during the process (measured using AOAC 984.27). Chloride was generally undetectable throughout the process (data not shown). Ash generally remains constant during the process (measured using AOAC 950.14A), as shown in FIG. 12. Table 7 below provides a summary of mass % (mass/dry weight) data for ions (Ca, P, Na, K) and ash for each replicate for each plant source tested.

TABLE 7

| | Calcium (mass %) | | | Phosphorus (mass %) | | | Sodium (mass %) | | | Potassium (mass %) | | | Ash (mass %) | | |
|---|---|---|---|---|---|---|---|---|---|---|---|---|---|---|---|
| | Flour | Extract | Refined PI | Flour | Extract | Refined PI | Flour | Extract | Refined PI | Flour | Extract | Refined PI | Flour | Extract | Refined PI |
| ALM 1 | 0.59 | 0.09 | 2.08 | 0.97 | 0.41 | 1.58 | 0.63 | 0.76 | 0.07 | 1.70 | 1.76 | 0.06 | 7.95 | 5.82 | 2.83 |
| ALM 2 | 0.63 | 0.09 | 1.90 | 1.19 | 0.43 | 1.53 | 0.56 | 0.63 | 0.04 | 1.92 | 1.76 | 0.04 | 8.35 | 5.37 | 7.28 |
| SES 1 | 0.20 | 0.10 | 0.36 | 1.24 | 0.64 | 0.43 | 0.43 | 1.49 | 0.03 | 1.01 | 1.33 | 0.02 | 6.42 | 6.55 | 3.30 |
| SES 2 | 0.20 | 0.06 | 0.21 | 1.20 | 0.39 | 0.44 | 0.49 | 1.17 | 0.05 | 1.00 | 1.00 | 0.01 | 6.29 | 5.90 | 1.59 |
| SOY 1 | 0.25 | 0.22 | 1.56 | 0.71 | 1.05 | 1.57 | 0.58 | 1.18 | 0.05 | 2.57 | 4.93 | 0.10 | 7.26 | 13.6 | 5.95 |
| SOY 2 | 0.26 | 0.20 | 1.61 | 0.71 | 0.81 | 1.49 | 0.65 | 0.88 | 0.05 | 2.58 | 3.84 | 0.09 | 7.16 | 10.7 | 6.67 |
| FAV 1 | 0.05 | 0.10 | 1.00 | 0.47 | 1.00 | 1.21 | 0.42 | 0.86 | 0.03 | 1.24 | 2.46 | 0.03 | 3.72 | 10.3 | 5.00 |
| FAV 2 | 0.07 | 0.11 | 1.11 | 0.41 | 0.86 | 1.22 | 0.70 | 1.14 | 0.05 | 1.29 | 2.34 | 0.03 | 3.86 | 8.00 | 5.52 |
| GAR 1 | 0.16 | 0.25 | 0.04 | 0.50 | 1.16 | 0.81 | 0.17 | 0.37 | 0.07 | 1.30 | 2.76 | 0.02 | 3.34 | 8.07 | 2.49 |
| GAR 2 | 0.14 | 0.17 | 0.93 | 0.44 | 0.94 | 0.98 | 0.29 | 0.32 | 0.03 | 1.42 | 2.67 | 0.03 | 3.85 | 7.97 | 5.13 |
| NAV 1 | 0.23 | 0.13 | 1.76 | 0.62 | 1.20 | 1.98 | 0.21 | 0.41 | 0.08 | 2.53 | 4.76 | 0.12 | 6.28 | 12.6 | 8.47 |
| NAV 2 | 0.18 | 0.13 | 1.70 | 0.64 | 1.23 | 1.93 | 0.21 | 0.38 | 0.07 | 2.53 | 4.80 | 0.12 | 6.43 | 12.1 | 8.72 |
| WBF 1 | 0.20 | 0.14 | 4.69 | 0.55 | 1.32 | 4.72 | 0.24 | 0.54 | 0.10 | 1.87 | 4.29 | 0.21 | 4.92 | 9.47 | 16.6 |
| WBF 2 | 0.26 | 0.13 | 1.42 | 0.46 | 1.07 | 1.42 | 0.26 | 0.52 | 0.08 | 1.84 | 3.98 | 0.11 | 5.25 | 10.3 | 6.42 |
| YPE 1 | 0.06 | 0.12 | 1.03 | 0.40 | 1.24 | 1.32 | 0.11 | 0.43 | 0.03 | 1.08 | 3.77 | 0.04 | 2.58 | 9.16 | 4.68 |
| YPE 2 | 0.10 | 0.18 | 1.08 | 0.50 | 1.27 | 1.21 | 0.23 | 0.43 | 0.05 | 1.59 | 3.59 | 0.03 | 4.30 | 10.4 | 5.75 |
| QUI 1 | 0.17 | 0.06 | 0.67 | 0.81 | 1.12 | 0.15 | 0.22 | 1.90 | 0.20 | 1.18 | 4.49 | 0.08 | 4.99 | 10.9 | 1.02 |

Table 8 shows the percent change from commercial flour/protein isolate mass (mass/dry weight) to refined protein isolate mass % (mass/dry weight) for protein, fat, carbohydrates and ions (Ca, P, Na, K) and are calculated based on values in Tables 6 and 7.

TABLE 8

| % Change | Protein | Fat | Carbohydrates | Calcium | Phosphorous | Sodium | Potassium |
|---|---|---|---|---|---|---|---|
| Almond Rep1 | 5 | 5 | 8 | 254 | 64 | −89 | −96 |
| Almond Rep2 | 27 | 25 | −100 | 202 | 29 | −93 | −98 |
| Sesame Rep1 | 82 | −77 | −100 | 81 | −66 | −93 | −98 |
| Sesame Rep2 | 66 | −66 | −100 | 5 | −63 | −90 | −99 |
| Soy Rep 1 | 26 | −14 | −48 | 526 | 121 | −92 | −96 |
| Soy Rep 2 | 46 | 18 | −100 | 512 | 109 | −93 | −97 |
| Fava Rep 1 | 163 | 33 | −92 | 1760 | 158 | −94 | −98 |
| Fava Rep 2 | 175 | 26 | −100 | 1615 | 196 | −94 | −98 |
| Garbanzo R1 | 207 | 70 | −100 | −78 | 62 | −61 | −98 |
| Garbanzo R2 | 170 | 79 | −100 | 568 | 124 | −89 | −98 |
| Navy bean R1 | 118 | 2 | −92 | 654 | 219 | −63 | −95 |
| Navy bean R2 | 123 | 18 | −87 | 843 | 199 | −66 | −95 |
| White bean R1 | 247 | 211 | −100 | 2256 | 763 | −61 | −89 |
| White bean R2 | 201 | 20 | −94 | 449 | 211 | −68 | −94 |
| Yellow pea R1 | 198 | 47 | −84 | 1695 | 226 | −69 | −97 |
| Yellow pea R2 | 171 | 56 | −100 | 1023 | 141 | −81 | −98 |
| Quinoa R1 | 36 | −51 | 22 | 298 | −82 | −6 | −93 |

Reducing Capacity

The reducing capacity is a proxy measurement for phenolic acids and other reducing compounds. Phenolic acids often create sour, bitter, and astringent flavors found in plant protein extracts; examples include flavonoids and tannins (see Huang et al, 1991; Roland et al., 2013). The overall decrease in the reducing capacity was from 31 to 61% from the extract to the final refined protein isolate. Table 9 below shows the reducing capacity, reported as gallic acid equivalents mg/L, was quantified using a modified Folin-Ciocalteu assay. The reducing capacity was reduced by 31-86% from the extract to the refined protein isolate.

The reducing capacity of each sample was measured using a microplate adaptation of the Folin-Ciocalteu method adapted from (Magalhães et al., 2010 "Rapid microplate high-throughput methodology for assessment of Folin-Ciocalteu reducing capacity" Talanta 83; 441-447.).

1. The extract and refined protein isolate samples were diluted with water to reach 0.3% by weight protein.
2. Sample preparation in the microplate consisted of mixing the following (in this order):
   a. 50 uL of sample/blank/standard
   b. 50 uL of Folin-Ciocalteu reagent 1:5 v/v (or 50 uL 0.4M HCl for matrix blank)
   c. 100 uL of 0.35NaOH
3. The samples were incubated for 3 min at room temperature.
4. Calibration samples were prepared using five gallic acid standards ranging from 5 mg/L to 150 mg/L (prepared from a 500 mg/L gallic acid stock daily prior to use).
5. The sample absorbance was measured at 760 nm in triplicate. The reducing capacity was expressed as gallic acid equivalents (GAE).
6. A spike of 50 mg/L of GA was added to some samples during assay development.

TABLE 9

| | Extract at 0.3% protein by weight (GAE mg/L) | Refined Protein Isolate at 0.3% protein by weight (GAE mg/L) | % Reduction from extract to Refined Protein Isolate |
|---|---|---|---|
| Fava | 57 | 28 | 50 |
| Garbanzo bean | 49 | 27 | 46 |
| Yellow pea | 53 | 29 | 44 |

TABLE 9-continued

| | Extract at 0.3% protein by weight (GAE mg/L) | Refined Protein Isolate at 0.3% protein by weight (GAE mg/L) | % Reduction from extract to Refined Protein Isolate |
|---|---|---|---|
| White bean | 47 | 30 | 37 |
| Navy bean | 49 | 24 | 51 |
| Soy | 66 | 45 | 31 |
| Almond | 50 | 19 | 61 |
| Sesame | 62 | 8.7 | 86 |
| Range | 46-62 | 9-45 | 31-86 |

Figure 13:
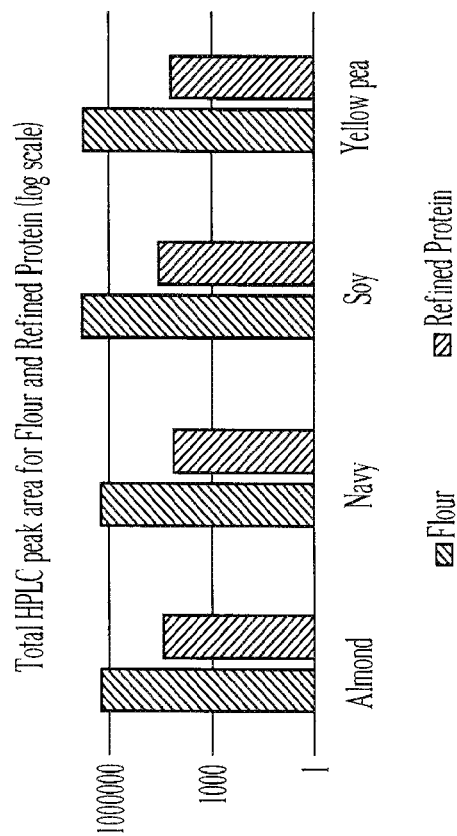
FIG. 13 shows the total peak area for the HPLC trace of the extract from the initial flour versus the refined protein, according to certain embodiments.
Figure 14A:
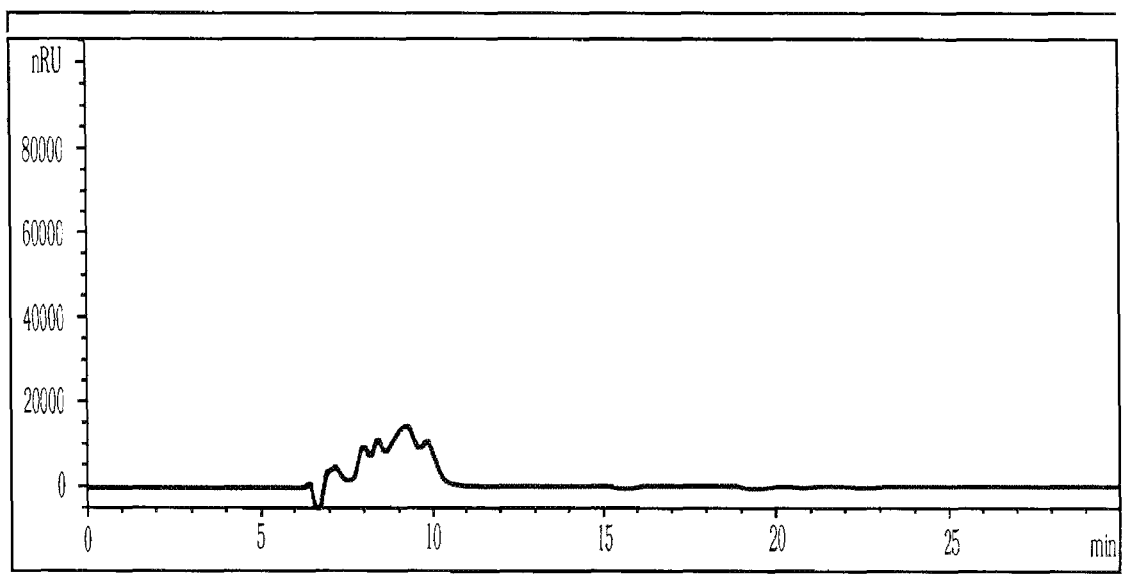
FIGS. 14A-14H show HPLC chromatograms that are related to FIG. 13.
Figure 14B:
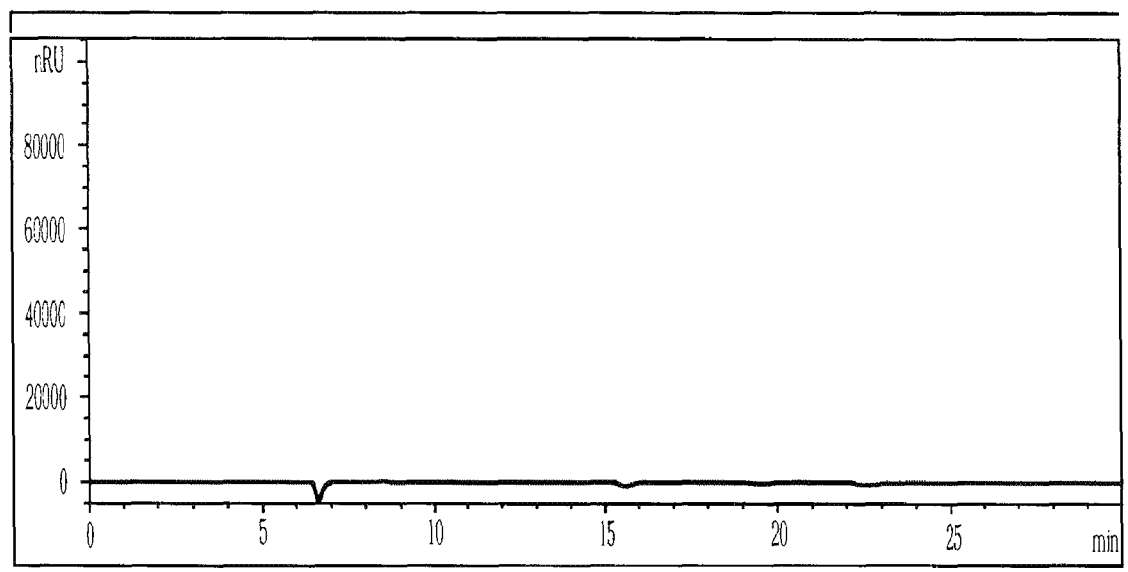
Figure 14C:
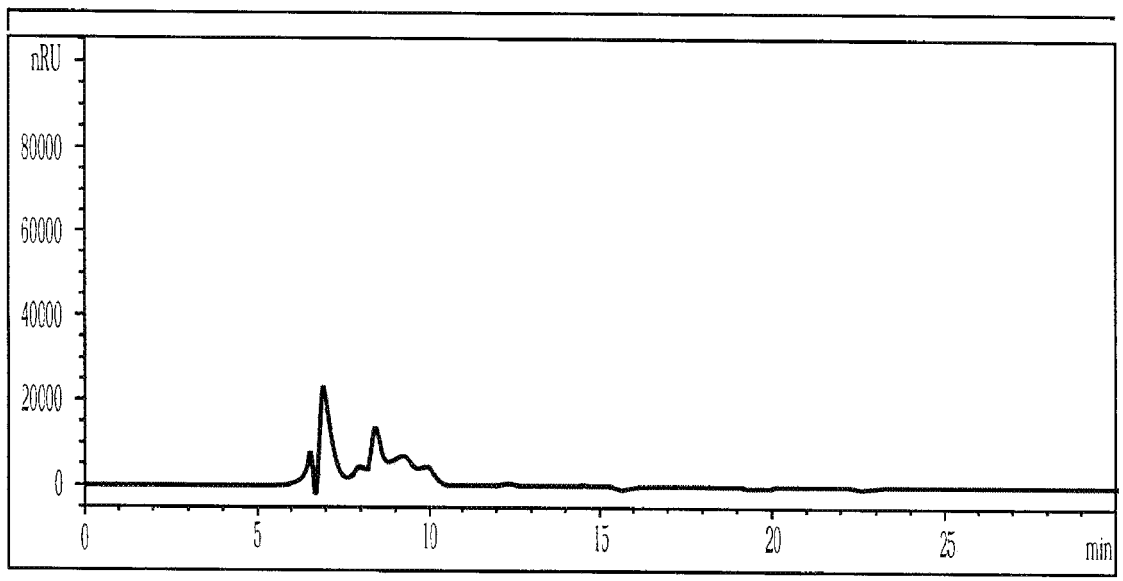
Figure 14D:
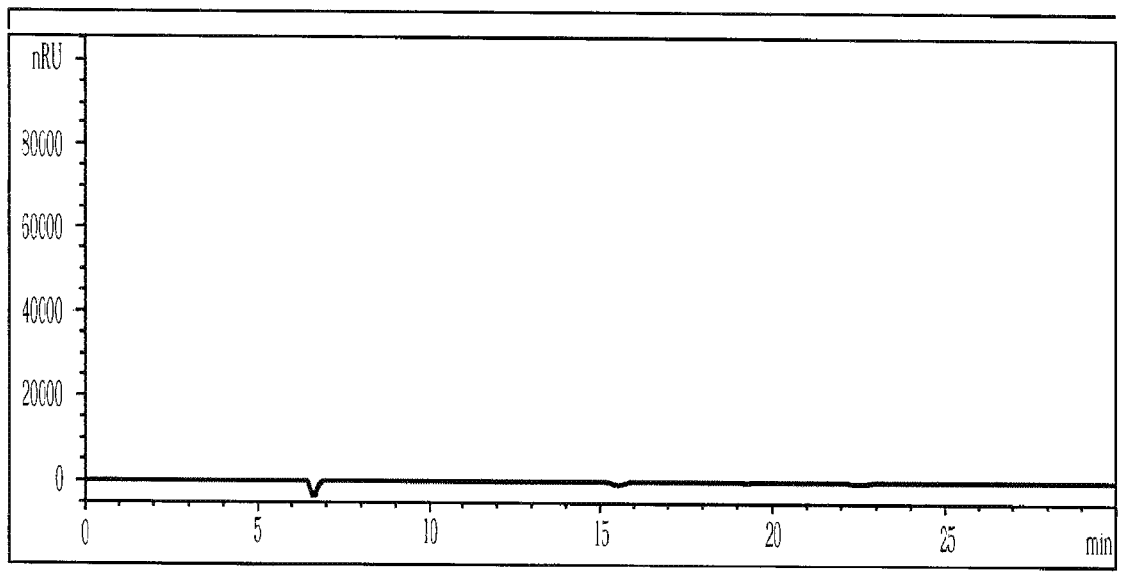
Figure 14E:
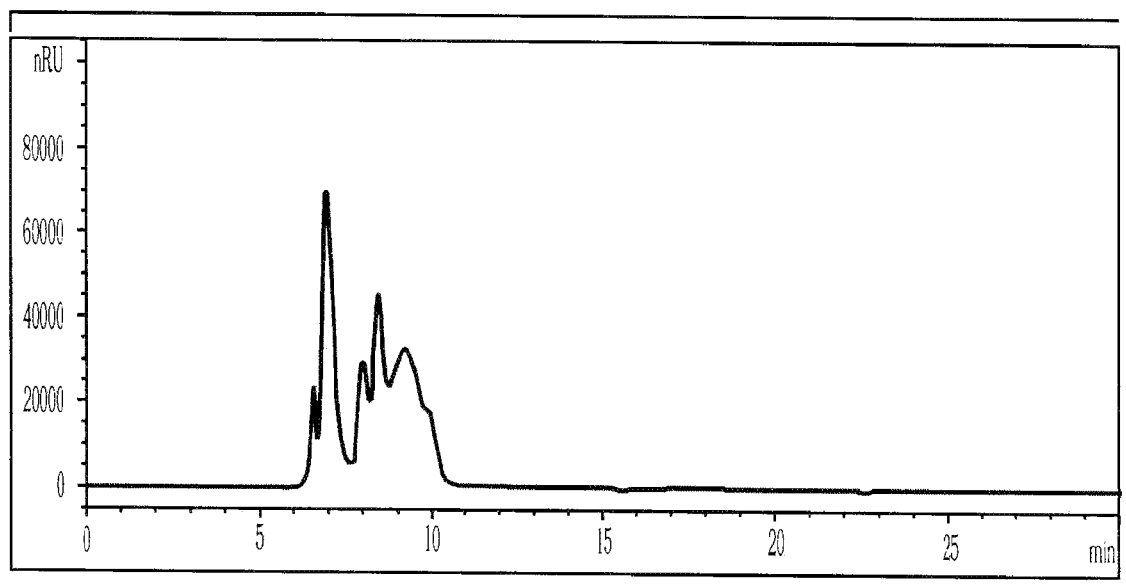
Figure 14F:
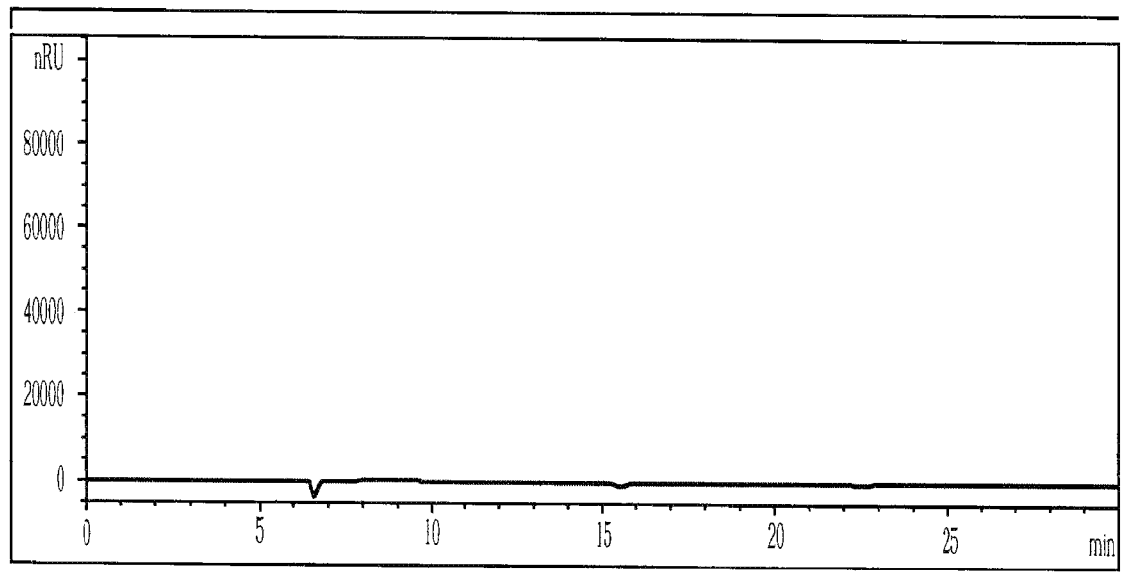
Figure 14G:
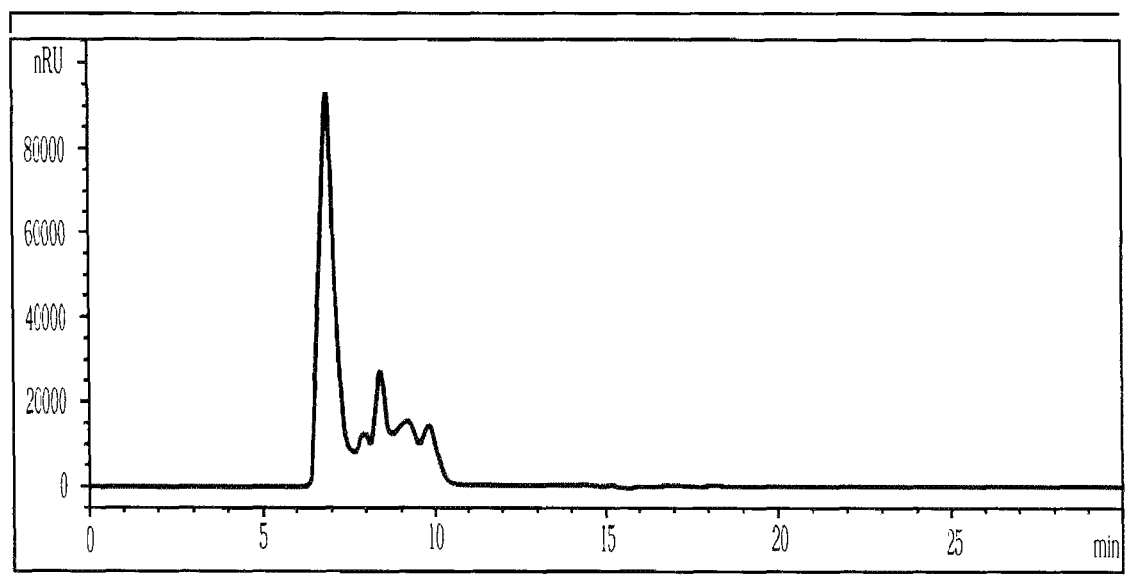
Figure 14H:
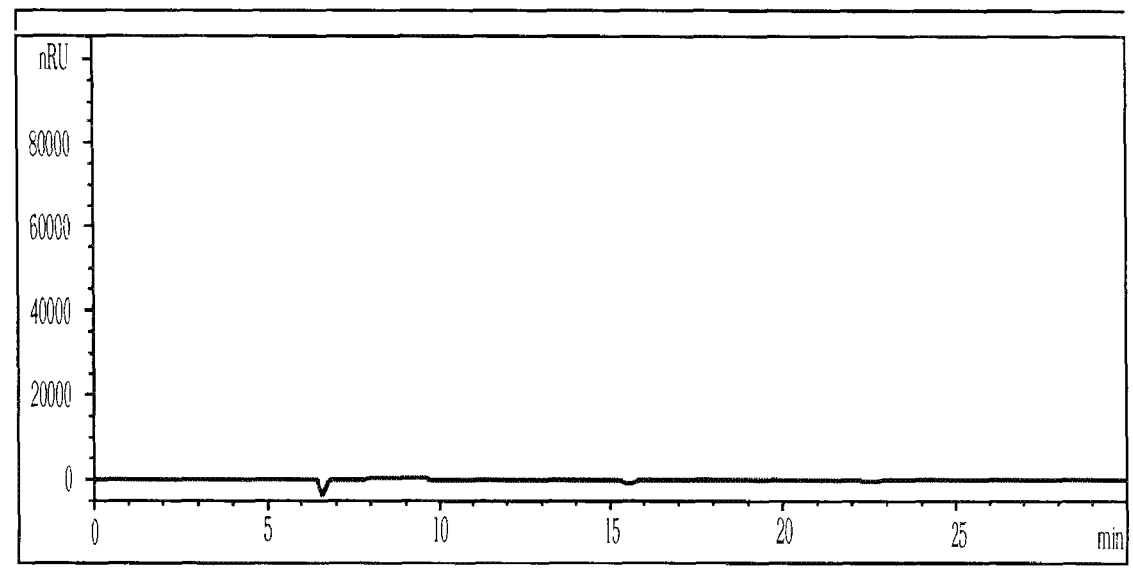

HPLC analysis was used to quantify the total extractable soluble sugars and organic acids in the initial commercial flour isolate and the refined protein isolate to demonstrate the level of purification in the refining process. The samples analyzed on HPLC were normalized to have the same amount of protein, spun and the supernatant was injected in a H-column (no acid digestion). Although we did not identify individual peaks in the HPLC trace, we compared the total peak area of the flour and refined protein isolate. These chromatograms show a reduction of the total peak area in the refined protein isolate—the total peak area is reduced by ~99% in each sample. FIG. 13 shows the total peak area for the HPLC trace of the extract from the initial flour versus the refined protein isolate; only ~1% of the initial small molecules remain in the extract following the isolation procedure. (Note the log scale). The actual chromatograms are shown in FIGS. 14A-G. FIG. 14A is the chromatogram for almond defatted flour diluted to 6.9% protein. FIG. 14B is the chromatogram for refined protein isolate from almond defatted flour, 6.9% protein. FIG. 14C is the chromatogram for navy bean flour ground in house and diluted to 3.6% protein. FIG. 14D is the chromatogram for refined protein isolate from the same navy bean flour, 3.6% protein. FIG. 14E is the chromatogram for Soy defatted flour diluted to 8.7% protein and FIG. 14F is the chromatogram for refined protein isolate from soy defatted flour, 8.7% protein. FIG. 14G is the chromatogram for yellow pea flour diluted to 7.4% protein and FIG. 14H is the chromatogram for refined protein isolate from yellow pea flour, 7.4% protein. Table 10 is a table of the HPLC peak areas depicted in FIG. 13. The % reduction in total peak area was nearly 100% in the samples tested

TABLE 10

| Total peak area | Flour | Refined Protein Isolate | % Reduction |
| --- | --- | --- | --- |
| Almond | 2,864,059 | 26,005 | 99.1 |
| Navy | 5,028,531 | 52,010 | 99.0 |
| Soy | 9,688,482 | 104,020 | 98.9 |
| Yellow pea | 19,355,660 | 208,040 | 98.9 |

GC Chromatograms

We used gas chromatography (GC) analysis to quantify the volatile compounds present in the flour and refined PI. Plants contain a variety of volatile compounds that may contribute at least in part to off-flavors and/or odors. Protein isolate samples were compared to their original flour source for five plant sources using gas chromatography. The samples were normalized to have the same amount of protein prior to analysis. The process in this example was able to reduce the total peak area from flour to final product by 88% to nearly 100%.

Figure 15:
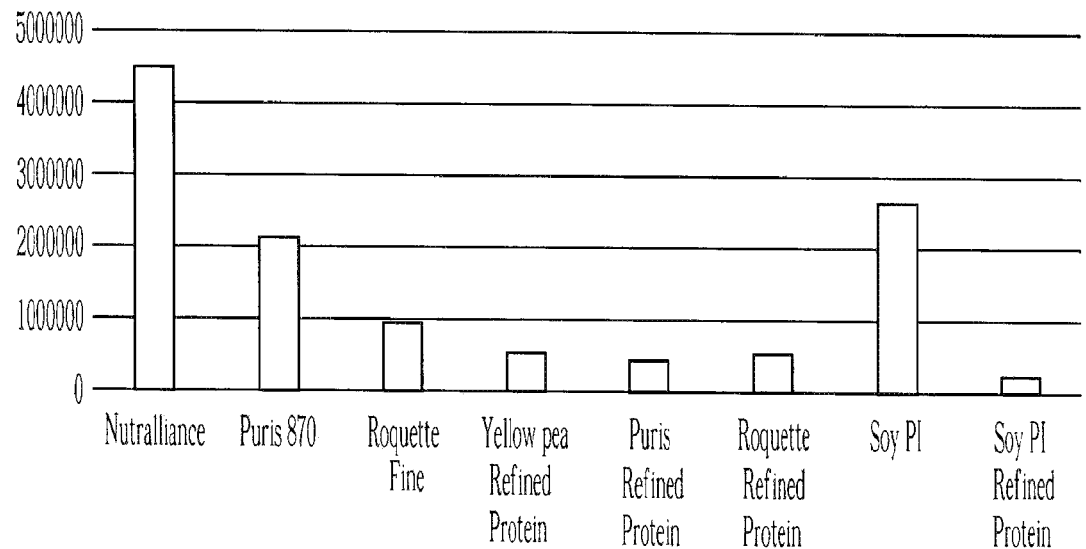
FIG. 15 shows the total peak area measured in the protein isolate and samples of refined protein isolate after the refining process, according to certain embodiments.
Figure 16A:
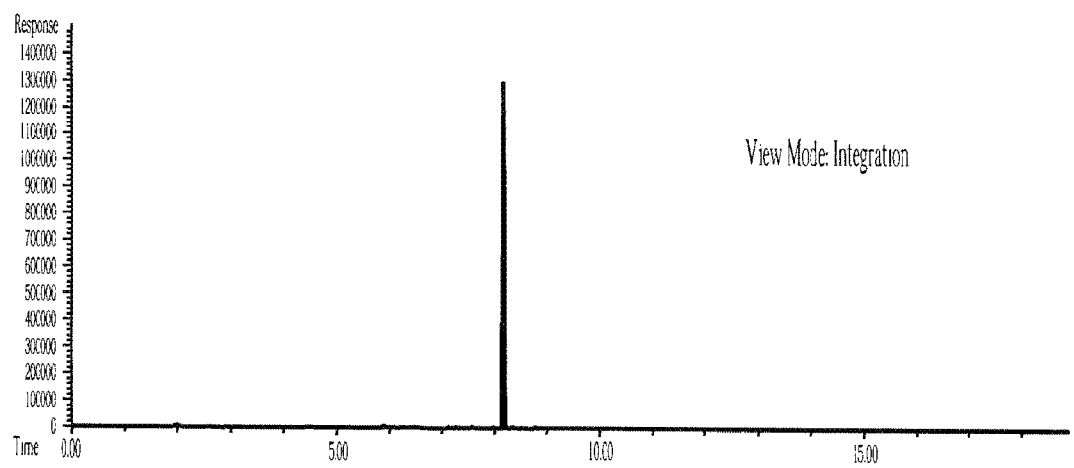
FIGS. 16A-16K show the GC chromatograms that are related to FIG. 15.
Figure 16B:
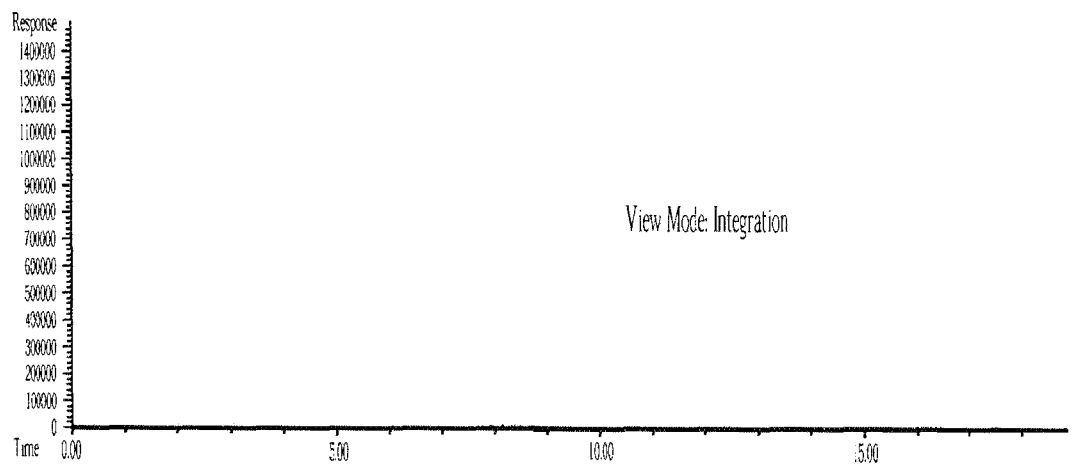
Figure 16C:
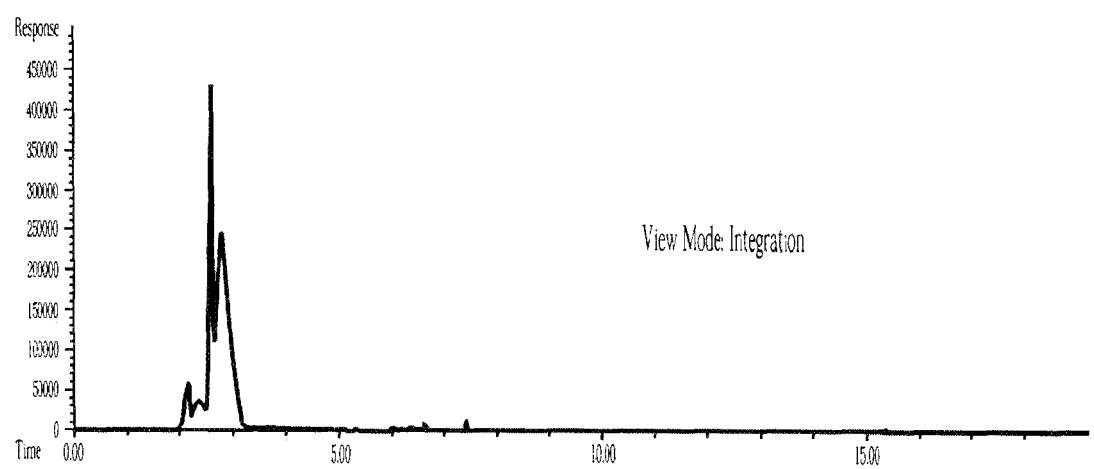
Figure 16D:
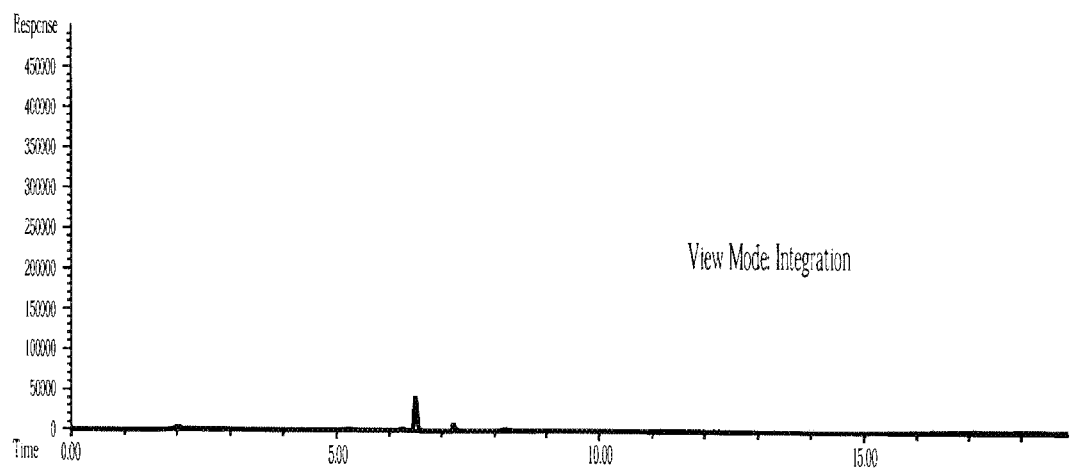
Figure 16E:
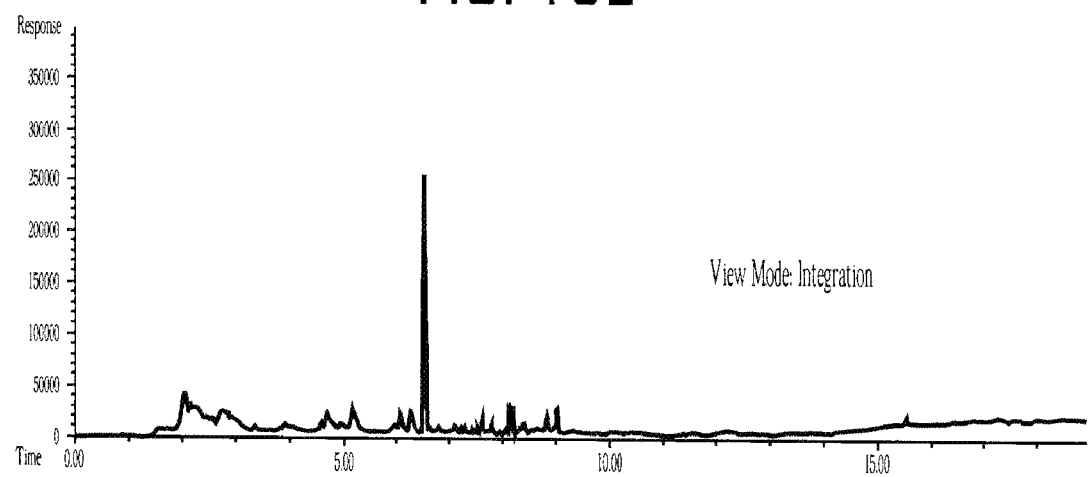
Figure 16F:
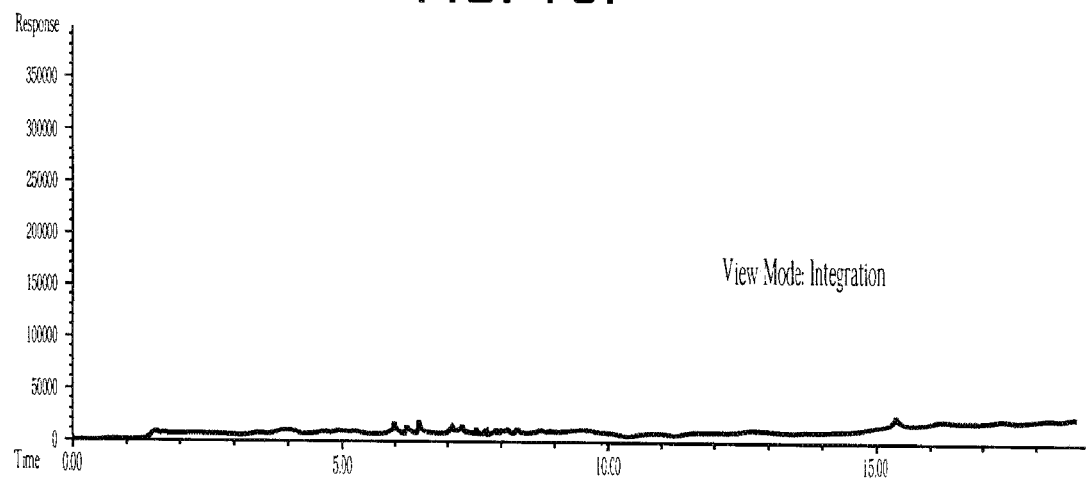
Figure 16G:
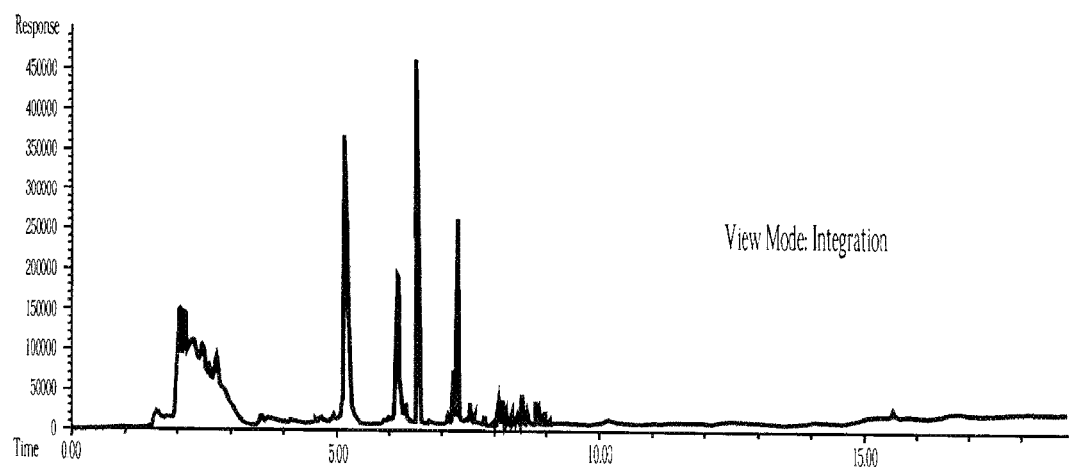
Figure 16H:
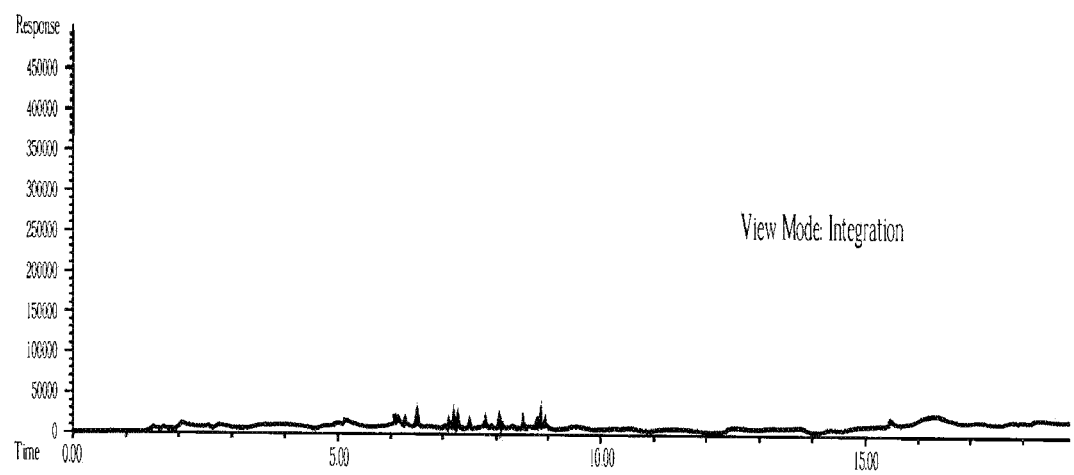
Figure 16I:
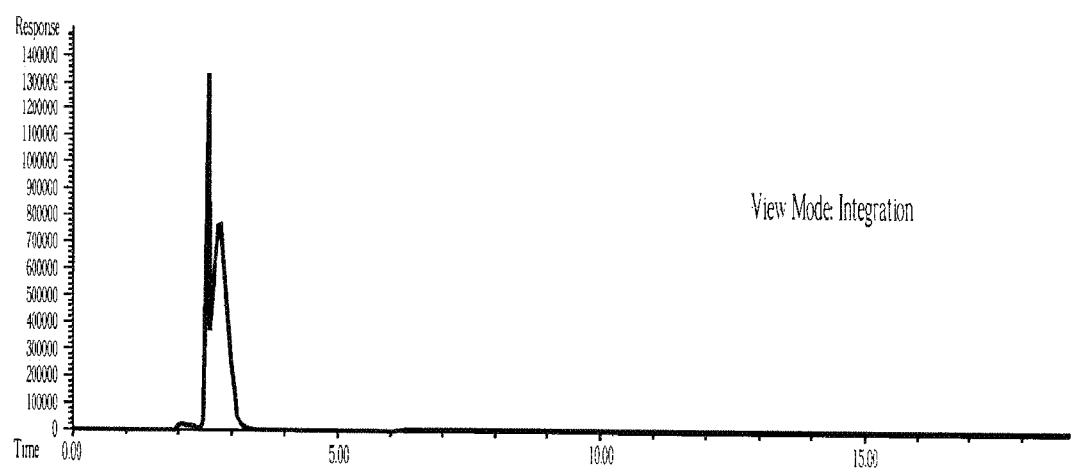
Figure 16J:
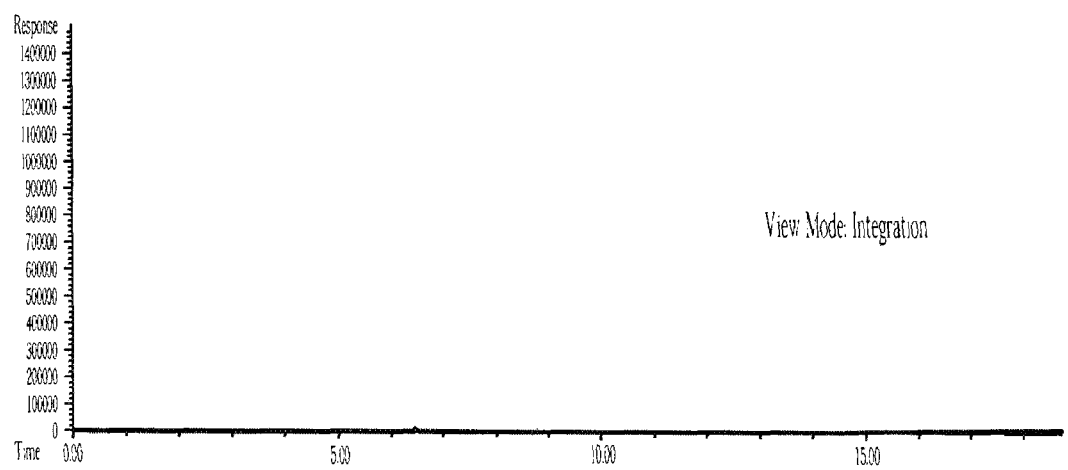
Figure 16K:
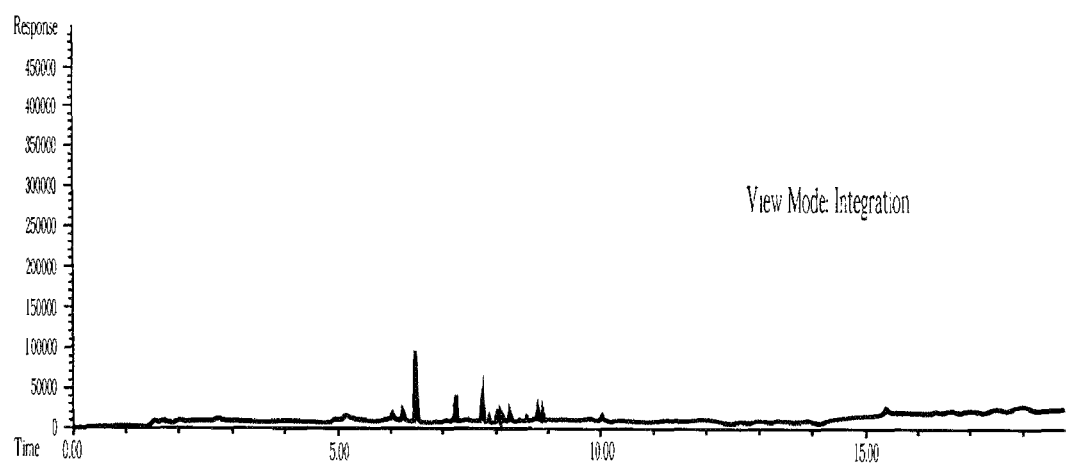

Also tested in this example was the effectiveness of the process on purifying commercial protein isolate. Several commercial isolates (Puris, Roquette) were tested before and after the refining purification process. FIG. 15 shows the total peak area measured in the commercial PI (black bars) is greater than the area in the samples of PI after the refining process (dotted bars). The refining process purified proteins resulted in the lowest peak areas in tested sources. Table 11 below shows the GC peak areas initial flour and refined PI samples. The % reduction ranged from 88 to nearly 100%. FIG. 16A shows the GC chromatogram for Almond deflated flour and FIG. 16B shows the GC chromatogram for refined PI from almond flour (the two samples were diluted to 10.7% protein). FIG. 16C shows the GC chromatogram for Garbanzo flour and FIG. 16D shows the GC chromatogram for refined PI from garbanzo flour (the two samples were diluted to 9.4% protein). FIG. 16E shows the GC chromatogram for soy defatted flour and FIG. 16F shows the GC chromatogram for refined PI from soy defatted flour (the two samples were diluted to 7.7% protein). FIG. 16G shows the GC chromatogram for White bean flour and FIG. 16H shows the GC chromatogram for refined PI from white bean flour (the two samples were diluted to 3.4% protein) FIG. 16I shows the GC chromatogram for Yellow pea flour; FIG. 16J shows the GC chromatogram for refined PI from yellow pea flour at the same scale; and FIG. 16K the GC chromatogram for refined PI from yellow pea flour and is the same GC chromatogram as shown in FIG. 16J but with an expended view of the lower portion of they axis such that certain peaks may be seen (the two samples were diluted to 8.6% protein).

TABLE 11

| Source | Flour (total peak area) | Refined PI (total peak area) | % of total area reduction from Flour to Refined PI |
| --- | --- | --- | --- |
| Defatted almond | 18,255,734 | 86,736 | 99.5 |
| Garbanzo bean | 68,212,786 | 2,336,181 | 96.6 |
| Soy | 1,931,423 | 232,517 | 88.0 |
| White bean | 8,228,243 | 377,364 | 95.4 |
| Yellow pea | 194,293,503 | 537,724 | 99.7 |

Figure 17A:
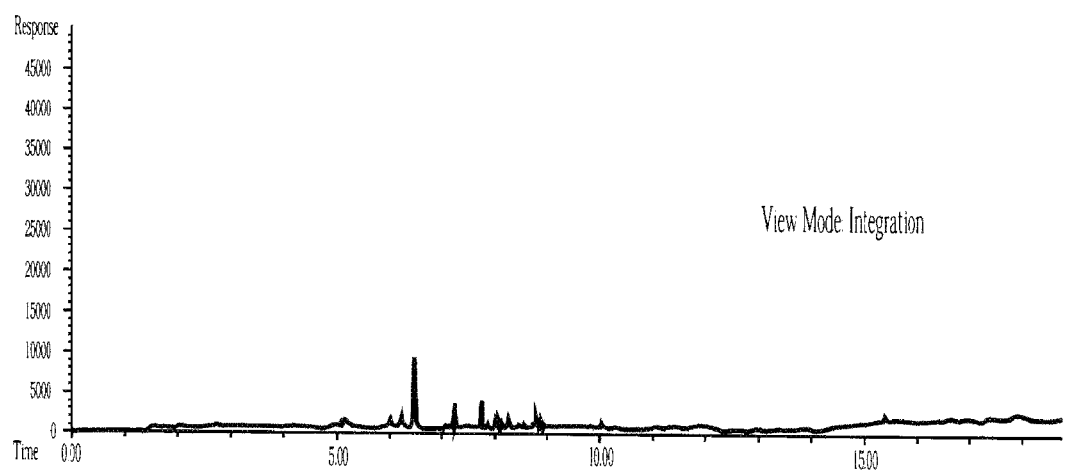
FIGS. 17A-17F show GC Chromatograms comparing commercial protein isolate samples to the same plant source after a processing run from flour to protein, according to certain embodiments.
Figure 17B:
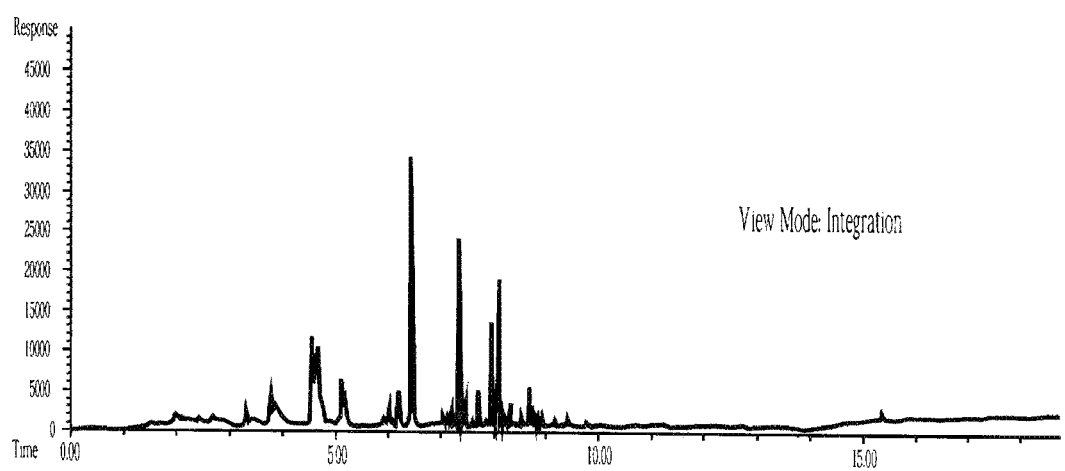
Figure 17C:
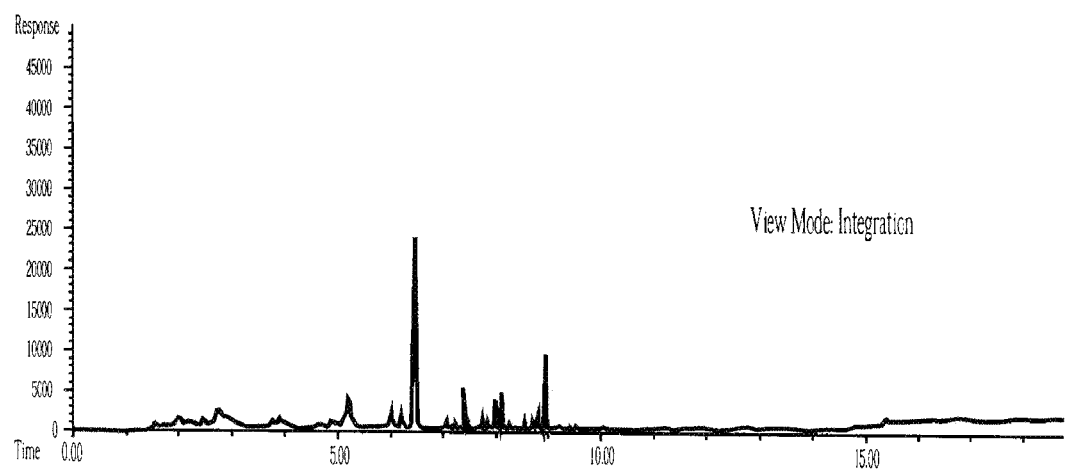
Figure 17D:
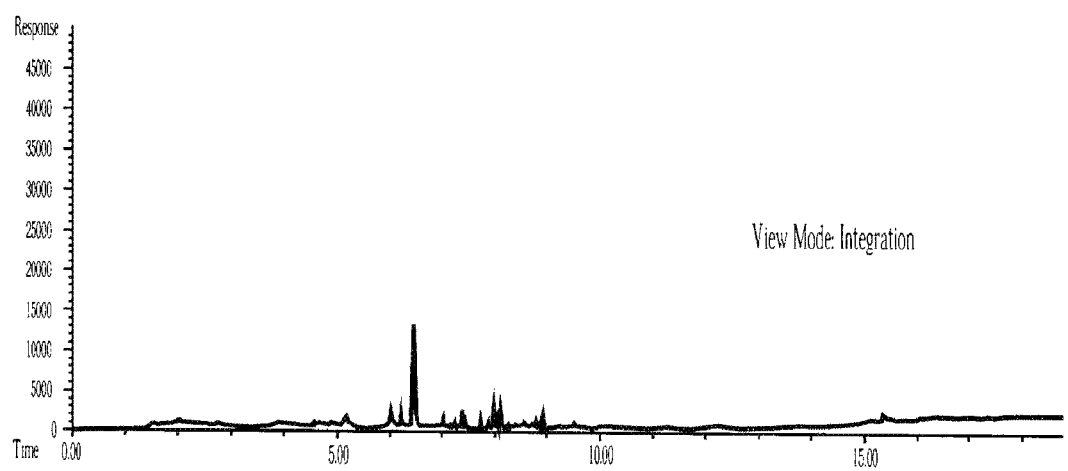
Figure 17E:
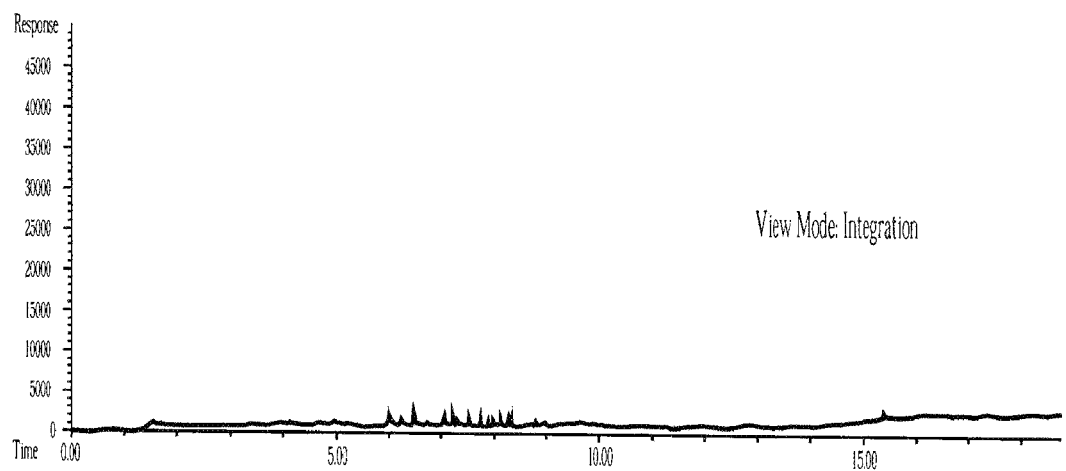
Figure 17F:
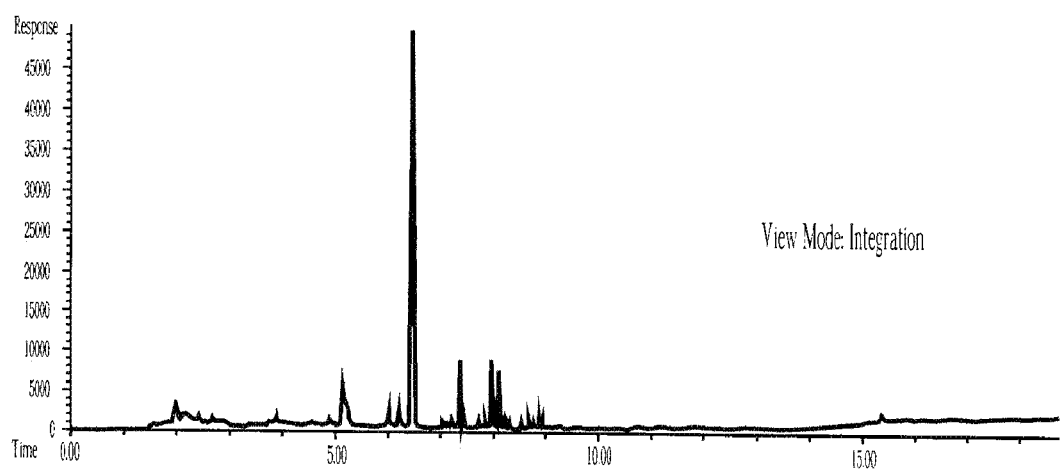

Garbanzo and yellow pea flour have a disproportionally large loading peak. The majority of the peaks do not appear in the PI. The total area reduction for each of the sources tested is greater than 88%. The refined protein isolates made form yellow pea and soy were compared to the commercial protein isolates. FIG. 17A-D shows GC Chromatograms comparing commercial protein isolate samples to the same plant source after the refining process run from flour to protein. FIG. 17A shows GC Chromatograms for refined protein isolate from yellow pea and this may be compared to three commercial protein isolates; Nutralliance PPI-80 (FIG. 17B), Puris Pea 870 (FIG. 17C) and Roquette (FIG. 17D). The four samples were diluted to 8.6% protein by weight. FIG. 17E-F shows GC Chromatograms comparing refined protein isolate from soy flour compared to Now Sport Soy Protein Isolate (the two samples were diluted to 7.5% protein by weight).

Soy Isoflavones and Tannins

Isoflavones and tannins are both compounds known to activate bitter taste receptors. Therefore, the present example evaluated the refined protein isolation process for its ability to remove tannins and specific bitter tasting isoflavones found in soy flour. The samples were normalized to protein for comparison, and it is clear that there is a strong reduction in the isoflavones detected in soy flour, daidzin, glycitin, and genistin (95%, 87%, and to below detection, respectively). Tannins, which generate an astringent, bitter flavor, were reduced by 84.7%. Other plant sources contain different amounts and types of isoflavones, therefore it is difficult to run this type of test on all eight sources. However, results with soy indicate that the refining isolation process is effective at reducing the levels of isoflavones and tannins in the final product. Table 12 shows concentrations of a known soy isoflavones in soy flour, aqueous extract, and refined protein isolate. The values are a % normalized to protein (result % (w/w)/protein % (w/w)×100). If the values are normalized to % dry mass, daidzin is 0.014% of dry mass, glycitin is below detection, genistin is 0.048% of dry mass. For tannins, the values normalized to % dry mass are 0.18% dry mass.

TABLE 12

| Test | Flour | Extract | PI (Refined) | % Reduction |
| --- | --- | --- | --- | --- |
| Daidzin | 0.377 | 0.731 | 0.018 | 95.2 |
| Glycitin | 0.048 | 0.088 | <0.006 | ND |
| Genistin | 0.473 | 0.744 | 0.061 | 87.1 |
| Tannins, as tannic acid | 1.507 | 3.139 | 0.231 | 84.7 |

Final Protein Characteristics
Color (L*, a*, b* Values)

One aspect of the refining protein isolation process is the removal of color compounds. Generating a purified white protein is desirable and as disclosed herein may be achieved by using one or more embodiments of the refining protein isolation process.

The color of the refined protein isolate obtained from commercial flour and other protein isolates in the market was measured using CIELAB color space in which L* represents lightness (0 is black and 100 is diffuse white), a* is the green/red scale (negative values represent green, positive values are red) and b* is the blue/yellow scale (negative values indicate blue, positive values are yellow). The samples were prepared as follows; 3% protein by weight, sunflower oil, sunflower lecithin, guar gum, gellan, and tap water. The mix is homogenized using a polytron mixer and allowed to settle prior to color analysis.

The L* values (related to the lightness of the sample) are higher in the refined protein isolate made from flours (ranging from 76 to 80) (see Table 13) than in commercial protein isolate (ranging from 66 to 74) (see Table 14). The b values (high b value, more yellow) are lower in PI made from flour.

TABLE 13

| PI from flour (Refined) | L* | a* | b* |
|---|---|---|---|
| Garbanzo bean | 76.9 | −1.21 | 13.6 |
| Navy bean | 77.7 | −1.13 | 5.91 |
| White bean | 75.6 | −1.13 | 4.51 |
| Fava | 77.8 | −1.70 | 11.7 |
| Defatted soy | 77.8 | −2.43 | 6.64 |
| Defatted sesame | 78.6 | −1.15 | 5.14 |
| Defatted almond | 80.7 | −0.90 | 5.50 |
| Yellow pea | 80.3 | −0.67 | 9.86 |
| Range | 76 to 80 | −2.5 to −0.7 | 4.5 to 12 |

TABLE 14

| Commercial PI | L* | a* | b* |
|---|---|---|---|
| Nutralliance PPI-80 (Yellow Pea Protein) | 65.9 | 0.27 | 13.5 |
| Puris Pea 870 (Yellow Pea Protein) | 74.2 | −1.13 | 12.1 |
| Roquette Fine (Yellow Pea Protein) | 70.4 | 0.23 | 11.2 |
| Roquette Extra Fine (Yellow Pea Protein) | 70.4 | 0.26 | 9.63 |
| Pisane F9 (Yellow Pea Protein) | 71.0 | −0.83 | 10.5 |
| Scoular YS 85% (Yellow Pea Protein) | 69.5 | 0.06 | 11.3 |
| Now sports Soy PI | 74.2 | −1.52 | 8.55 |
| Range | 66 to 74 | −1.5 to 0.3 | 8.5 to 13 |

TABLE 15

|  | Instability index (average, n = 6) | sd | PCV |
|---|---|---|---|
| Yellow pea | 0.443 | 0.02 | 4.7 |
| Garbanzo bean | 0.429 | 0.02 | 5.0 |
| Fava bean | 0.476 | 0.02 | 4.5 |
| White bean | 0.307 | 0.03 | 9.9 |
| Navy bean | 0.282 | 0.02 | 6.1 |
| Soy | 0.244 | 0.03 | 10 |
| Sesame | 0.301 | 0.01 | 3.9 |
| Almond | 0.511 | 0.03 | 6.4 |
| Whey (n = 3) | 0.285 | 0.06 | 20 |
| Rice (n = 4) | 0.466 | 0.05 | 11 |

Taste Panel

To compare the taste profile of the refined PI with a commercial protein isolate, emulsions were generated with each protein and submitted to a trained taste panel at Kansas State University for analysis. The source for the refined PI in this test was the commercial PPI run through the refining process. The commercial protein was rinsed to reach the same conductivity of the refined PI prior to use in order to remove the high level of sodium present in the majority of commercial pea protein isolates. Each solution consisted of protein (3.35% by weight), sunflower oil (1.48% by weight) and lecithin and gums to stabilize the emulsion. The emulsion ingredients are set forth in Table 16.

TABLE 16

| Item | Product name | Supplier | Amount (by weight %) |
|---|---|---|---|
| TIC Gum Guar | Guar, Pre-hydrated Organic 3500 F | TIC Gums | 0.08% |
| CP Kelco Gellan | Gellan, Kelcogel HA-B | CP Kelco | 0.03% |
| Lecithin | Lecithin, GIRALEC sunflower non-GMO | Lasenor | 0.09% |
| Oil, sunflower | Oil, Sunflower Expeller Oleic | Oilseeds International | 1.48% |
| Water | Water | Tap | |
| Protein paste or PPI | Refined protein or Roquette S85F | n/a or Roquette | 3.35% |

Emulsion Stability

In order to compare variation in protein functionality, the emulsion stability of protein isolated from 8 flour sources, as well as commercial whey and rice protein was measured (see table 15). A lower instability index indicates a more stable emulsion. The instability index changes for the different sources. Almond protein creates the most instable emulsion of those tested while emulsions created with soy and navy bean protein are more stable. Yellow pea, garbanzo and fava have similar stability. This indicates that the refining protein isolation process may be utilized to generate proteins with different functionalities and is useful for end product development.

In this example, the method used in measuring the emulsion stability of the 8 flour sources and whey and rice protein was measured following the protocol below as indicated below:
1. Mix 720 uL of 3.2% protein solution with 80 uL sunflower oil and vortex for 10 min at speed 9.
2. Let settle for 5 min. Take 200 uL of the emulsion and mix with 800 uL of SUS 0.1%.
3. Measure the instability index in the LUMifuge® (by LUM GmbH), spinning a 350 ul sample at 1500 rpm for 3 min at 20° C.

Figure 18A:
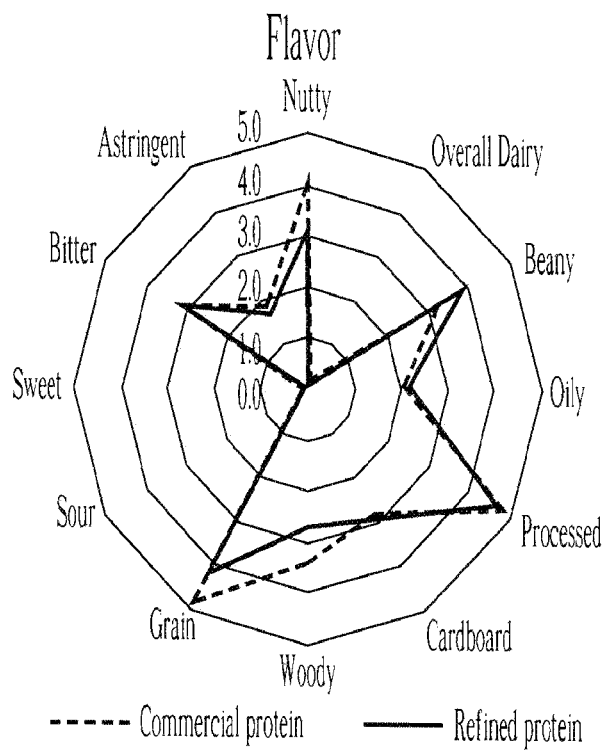
FIGS. 18A-18C show the differences in taste attributes between the emulsions generated with a refined protein or rinsed commercial pea protein (Roquette S85F), according to certain embodiments.
Figure 18B:
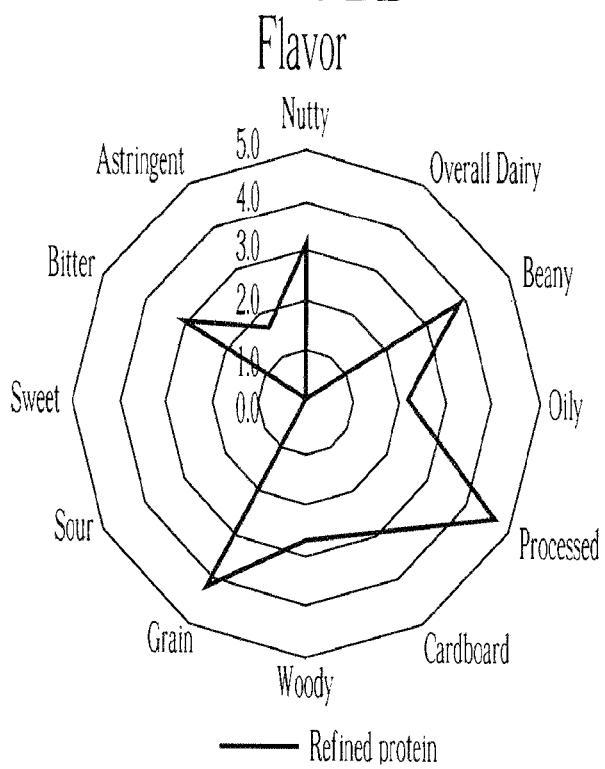
Figure 18C:
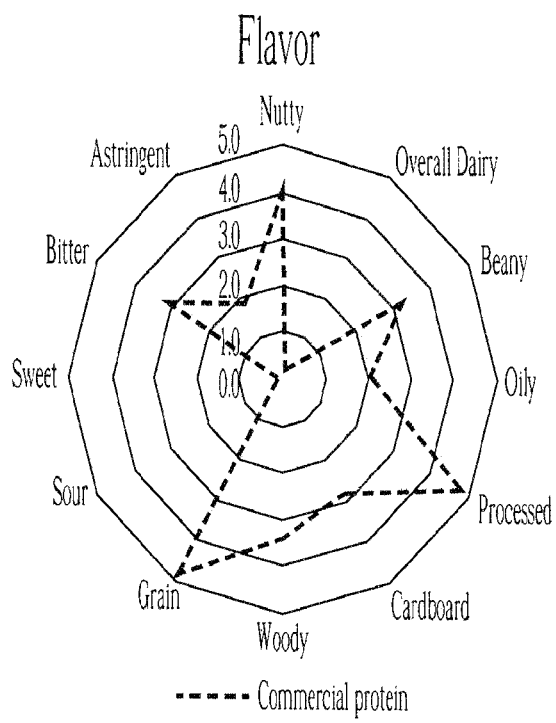
Figure 19:
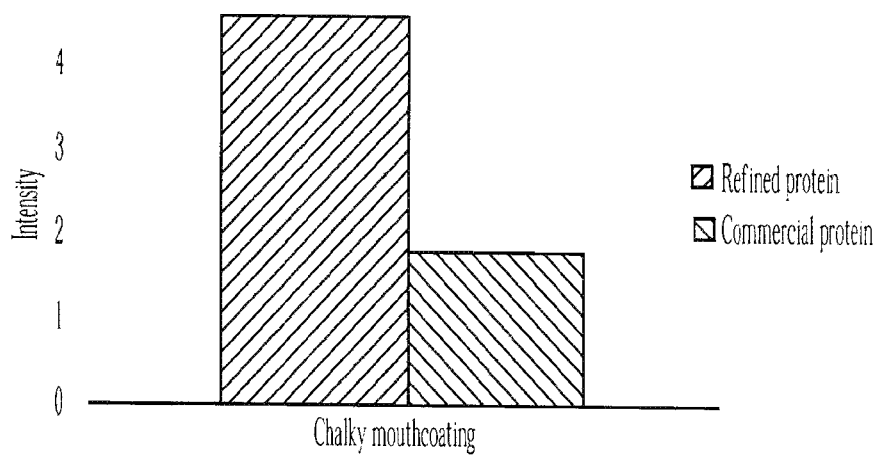
FIG. 19 shows aftertaste comparison between the emulsions generated with commercial protein and an emulsion containing refined protein prepared according to certain embodiments.
Figure 20:
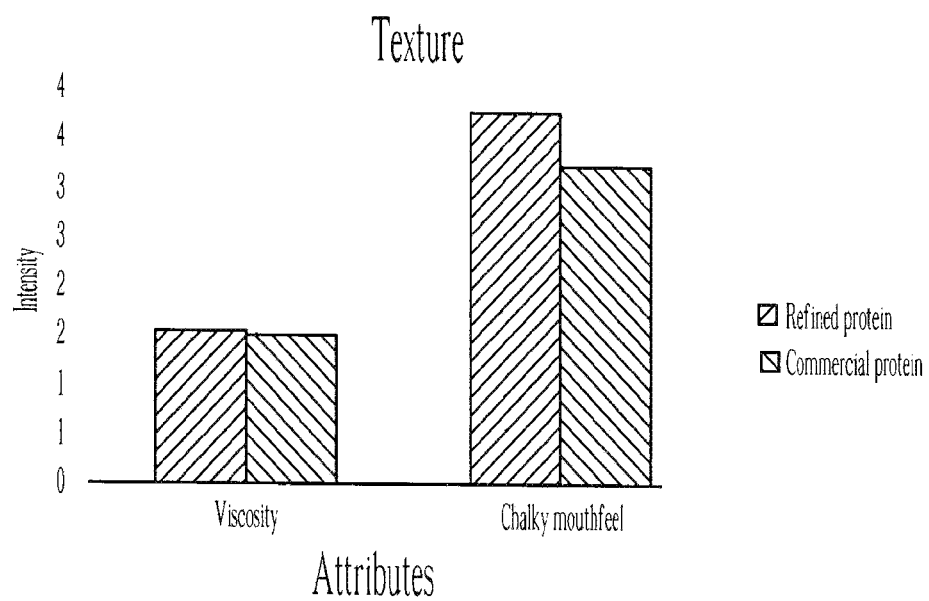
FIG. 20 shows texture comparison between the emulsions generated with commercial protein and a refined protein prepared according to certain embodiments.
Figure 21A:
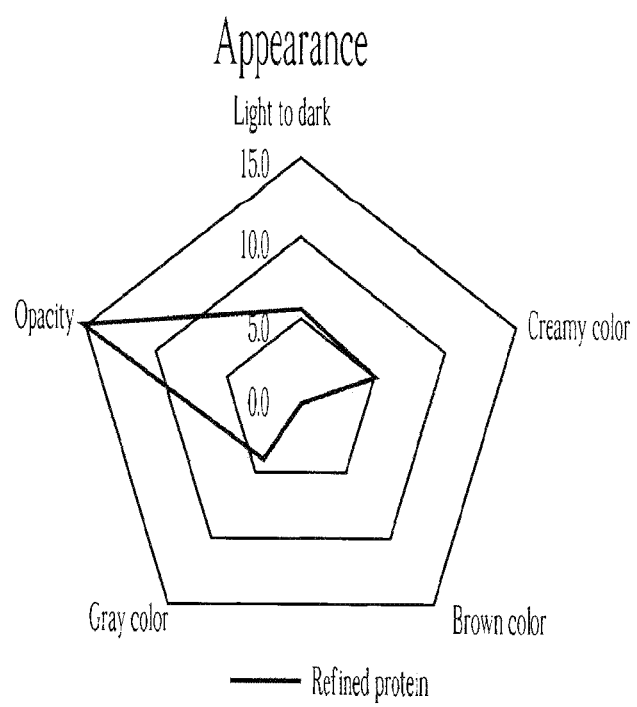
FIGS. 21A and 21B show an appearance comparison between the emulsions generated with commercial protein and a refined protein prepared according to certain embodiments.
Figure 21B:
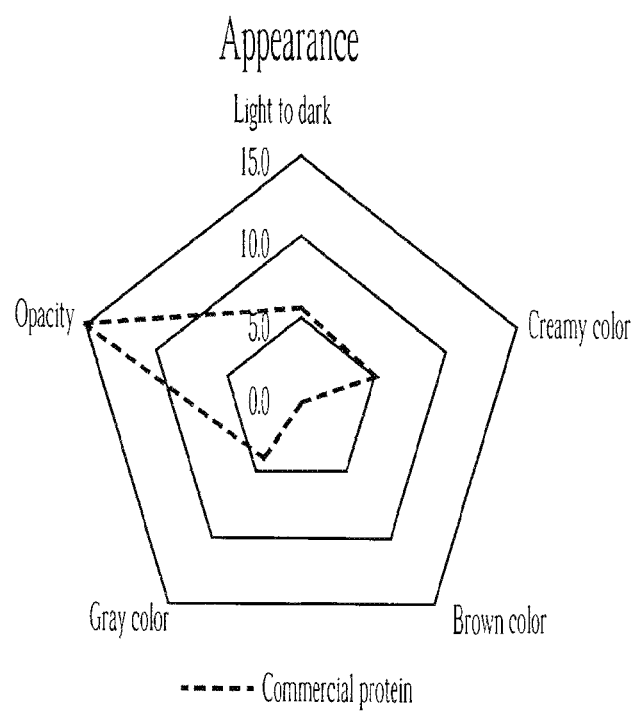

The taste panel evaluated the emulsions for 12 different flavor attributes, assigning the strongest flavor score of a 5.0 to the flavors grain and processed. The commercial PPI had stronger "nutty", "woody", and "grain" flavors (~1.0 point higher), while the refined PI had a slightly higher score for "beany". The source for the refined PI was the commercial PI it was compared against, therefore this test demonstrates that the refining isolation process removes multiple taste attributes and generates a cleaner tasting product. FIG. 18A shows the differences in taste attributes between the emulsions generated with refined PI or rinsed commercial PPI (Roquette S85F). FIG. 18B shows the individual plots of taste attributes in the emulsions generated with refined PI. FIG. 18C shows the individual plots of taste attributes in the emulsions generated with the rinsed commercial PPI (Roquette S85F). Table 16 shows the differences in taste attributes depicted in FIG. 18A. The greatest differences were in flavor attributes Nutty, Beany, Woody, and Grain. Further evaluations are provided in FIG. 19 (aftertaste comparison between commercial protein and refined protein), FIG. 20 (texture comparison between commercial protein and a refined protein) and FIGS. 21A and B (appearance comparison between commercial protein and a refined protein).

Example 9: Producing a Refined Protein at Commercial Scale

Twenty-five batches of refined protein were made for use as an ingredient in a dairy milk analogue. The manufacturing was performed at a commercial scale as follows:

1. 600-kg of pea protein isolate (Roquette S85F) was batched with water for a final solids loading of 12% (by wt %)
2. 3.2-kg of NaOH was mixed into the pea protein and water slurry
3. 46-kg of 34% (by wt) HCl was then mixed into the pea protein and water slurry
4. 17.8-kg of anhydrous $CaCl_2$) was then mixed into the pea protein and water slurry
5. The mixture was recirculated through 3 parallel decanter centrifuges, removing 22 gpm of liquid from the slurry that was replaced with 22 gpm pure water for 2.5 hours until bulk conductivity was reduced to 2500 uS/cm2.
6. The slurry was then dewatered using the decanter centrifuges until final dry solids was between 19-25%, and the protein was loaded into 275 gallon totes.

The final batch mass, L*a*b* color values, yield (wt % basis), dry solids (wt %), and protein content (wt %) of are shown in the table 17 below. The color of an emulsion generated from the protein paste was determined as described in Example 8.

TABLE 17

| Batch # | Batch mass (kg) | a* (color) | b* (color) | L* (color) | Yield (wt %) | Dry Solids (wt %) | Protein (wt %) |
|---|---|---|---|---|---|---|---|
| 1 | 2934 | 5.0 | 18.9 | 72.1 | 73% | 21% | 15% |
| 2 | 2899 | 5.4 | 20.0 | 71.6 | 75% | 20% | 15% |
| 3 | 2899 | 5.6 | 18.7 | 71.5 | 77% | 21% | 16% |
| 4 | 2989 | 5.4 | 19.7 | 71.6 | 80% | 21% | 16% |
| 5 | 3123 | 5.3 | 18.7 | 72.5 | 84% | 24% | 16% |
| 6 | 3012 | 5.6 | 20.3 | 72.1 | 82% | 22% | 16% |
| 7 | 2987 | 5.0 | 17.7 | 73.3 | 82% | 22% | 16% |
| 8 | 2877 | 5.3 | 19.5 | 71.6 | 79% | 24% | 16% |
| 9 | 3122 | 5.5 | 20.7 | 70.8 | 86% | 21% | 17% |
| 10 | 3009 | 5.7 | 19.4 | 71.0 | 84% | 22% | 17% |
| 11 | 3078 | 5.5 | 20.0 | 72.2 | 86% | 24% | 17% |
| 12 | 2877 | 5.6 | 19.6 | 72.5 | 81% | 24% | 17% |
| 13 | 2799 | 5.5 | 20.3 | 71.3 | 79% | 21% | 17% |
| 14 | 2867 | 5.4 | 19.7 | 70.8 | 82% | 23% | 17% |
| 15 | 3013 | 5.8 | 20.0 | 71.1 | 86% | 23% | 17% |
| 16 | 2807 | 5.4 | 20.1 | 70.8 | 81% | 22% | 17% |
| 17 | 2912 | 5.5 | 19.2 | 71.6 | 85% | 23% | 17% |
| 18 | 2999 | 5.4 | 19.7 | 71.7 | 88% | 22% | 18% |
| 19 | 2678 | 5.6 | 21.0 | 71.2 | 78% | 19% | 18% |
| 20 | 2789 | 5.3 | 19.5 | 71.6 | 82% | 23% | 18% |
| 21 | 2756 | 5.9 | 20.6 | 71.4 | 81% | 24% | 18% |
| 22 | 2867 | 5.4 | 19.5 | 71.5 | 85% | 22% | 18% |
| 23 | 2891 | 6.0 | 19.9 | 70.6 | 86% | 24% | 18% |
| 24 | 2913 | 5.6 | 20.6 | 70.9 | 87% | 23% | 18% |
| 25 | 2699 | 5.6 | 19.1 | 71.5 | 82% | 24% | 18% |
| Average | 2912 | 5 | 20 | 72 | 82% | 22% | 17% |

Example 10: Chocolate Spread Made from Refined Protein

A dessert spread was made using the refined protein with the following ingredients shown in Table 18 and the procedure provided below.

TABLE 18

| Ingredient | Supplier | Weight (g) | % (by wt) |
|---|---|---|---|
| Organic High Heat Sunflower Oil | Spectrum | 145.6 | 29.1% |
| Refined protein | N/A | 165.9 | 33.2% |
| Granulated sugar | C&H | 112.7 | 22.5% |
| Organic agave inulin | Ciranda | 49.1 | 9.8% |
| Rushmore cocoa powder | Blommer | 23.1 | 4.6% |
| Sunflower Lecithin, Non-GMO | Austrade | 2.5 | 0.5% |
| Sea salt, refined | Cargill | 1.1 | 0.2% |

Procedure:

1. Weigh out ingredients.
2. Add sugar to blender, blend on high for 30 seconds. Add dry solids to liquids, mix to combine with spatula.
3. Add 5× weight in ball bearings to panning equipment, heat for 5 minutes.
4. Add to panning equipment, run 11 hrs, scraping down as necessary.
5. Store at 4° C.

Example 11: Nutritional Shake Made with Refined Protein

A nutritional beverage was made using the refined protein with the following ingredients shown in Table 19 and the procedure provided below.

Procedure:

1. Make plant based milk using the protocol from Example 2 above.
2. Mix ingredients for the powder blend based on table 20 below
3. Add powder blend to the plant based milk and mix well.

TABLE 19

| Component | Supplier | Code | Weight (g) | Percent |
|---|---|---|---|---|
| Nutritional Shake | | | | |
| Plant Based Milk, | See Formula in example 2 Table 4 | | 354.88 | 88.53% |
| Powder Blend | See Formula in Table 20 | | 46.00 | 11.47% |
| | | | 400.88 | 100.00% |

TABLE 20

| Ingredient | Supplier | Code | Weight (g) | Percent | Shake Percent |
|---|---|---|---|---|---|
| Powder Blend | | | | | 8.525% |
| Refined Protein | Ripple Foods | Spray dried protein | 39.00 | 39.00% | 4.475% |
| Flaxseed Powder | Glanbia | | 12.43 | 12.43% | 1.426% |
| Hemp Protein | Hemp OilCanada | 50% Protein | 4.00 | 4.00% | 0.459% |
| Sacha Inchi Protein | Scoular | 65% Protein | 1.00 | 1.00% | 0.115% |
| *Acacia* Gum | TIC | Spray Dried | 5.00 | 5.00% | 0.574% |
| Cocoa Powder | Cargill/Gillco | 10/12 Alkalized | 15.00 | 15.00% | 1.721% |
| Maca | | | 3.00 | 3.00% | 0.344% |
| Spirulina | RFI | | 3.00 | 3.00% | 0.344% |
| Chlorella | | | 3.00 | 3.00% | 0.344% |
| Broccoli Powder | Van Drunen | Air Dried | 2.00 | 2.00% | 0.229% |
| Kale Powder | Van Drunen | Air Dried | 2.00 | 2.00% | 0.229% |
| Chocolate Flavor | | | 5.00 | 5.00% | 0.574% |
| *Vanilla* Flavor | | | 2.00 | 2.00% | 0.229% |
| Vitamin Blend, 12 Fruit & Veggie Blend | NutriFusion | NF 661 | 0.32 | 0.32% | 0.037% |
| *Papaya* Extract | | | 1.00 | 1.00% | 0.115% |
| Antioxidant Blend | Futureceuticals | | 0.30 | 0.30% | 0.034% |
| Beet Powder | Van Drunen | | 1.00 | 1.00% | 0.115% |
| Probiotic | Ganedan | BC30 | 0.20 | 0.20% | 0.023% |
| *Stevia* | PureCircle | Reb A 97% | 0.35 | 0.35% | 0.040% |
| Salt, Granular | Cargill | Hi-Grade | 0.40 | 0.40% | 0.046% |
| | | | 100.00 | 100.00% | 100.000% |

Example 12. Other Exemplary Non-Limiting Embodiments

Further advantages of the claimed subject matter will become apparent from the following examples describing certain embodiments of the claimed subject matter.

1. A dairy product analog comprising at least about 1% by weight of a protein obtained from one or more non-animal natural or modified non-animal natural sources, and having a neutral color that is defined by an L* value of at least about 70, an a* value of between about −1.5 and about +1.5, and a b* value of between about −12 and about +12.

2. The dairy product analog of Example 1, wherein the dairy product analog further comprises lipid obtained from one or more non-animal natural or modified non-animal natural sources.

3. The dairy product analog of Examples 1 or 2, wherein at least one of the one or more non-animal natural or modified non-animal natural sources is a plant.

4. The dairy product analog of Example 3, wherein the plant is a legume.

5. The dairy product analog of Example 4, wherein the legume is pea.

6. The dairy product analog of Example 1, wherein the dairy product analog comprises less than about 1% by weight of saturated fat.

7. The dairy product analog of Example 1, wherein the dairy product analog is substantially devoid of or devoid of one or more ingredients selected from the group consisting of a nut protein, cholesterol, and lactose.

8. The dairy product analog of Example 1, wherein the dairy product analog further comprises at least about 0.05% by weight of calcium.

9. A method for obtaining a yield of a color-neutral refined protein component from a non-animal natural and/or modified non-animal natural source comprising the steps of:

a) obtaining a protein preparation from the non-animal natural or modified non-animal natural source;
b) washing the protein preparation at a wash pH;
c) extracting the protein preparation at an extraction pH to obtain an aqueous protein solution;
d) separating the aqueous protein solution from non-aqueous components;
e) adding salt;
f) precipitating the protein from the aqueous protein solution at a precipitation pH to obtain a protein precipitate;
g) separating the protein precipitate from non-precipitated components; and
h) washing the protein precipitate to obtain the color-neutral refined protein component at the substantial yield.

10. The method of Example 9, wherein the non-animal natural or modified non-animal natural source is a plant.

11. The method of Example 10, wherein the plant is a legume.

12. The method of Example 11, wherein the legume is pea.

13. The method of Example 9, wherein the wash pH is between about 3 and about 5.

14. The method of Example 9, wherein the extraction pH is between about 8 and about 9.

15. The method of Example 9, wherein the salt added is calcium dichloride at a concentration of between about 50 mM and about 100 mM.

16. The method of Example 9, wherein the precipitation pH is between about 5 and about 6.

17. The method of Examples 9, wherein the method further comprises the step of adding between about 0.05% and about 12% by weight of polysaccharide to the aqueous protein solution.

18. The method of Example 9, wherein the yield is between about 50% and about 90%.

19. A color-neutral refined protein component, wherein the color-neutral refined protein component is obtained from a non-animal natural and/or modified non-animal natural source by a method of one or more of the Examples 9 to 18.

20. The color-neutral refined protein component of Example 19, wherein the color-neutral refined protein component is a paste comprising between about 4% and about 25% by weight of protein, between about 0.1% and about 1.5% by weight of calcium, and between about 50% and about 90% by weight of water.

21. The color-neutral refined protein component of Example 19, wherein the color-neutral refined protein component is a dry powder comprising between about 70% and about 90% by weight of protein, and between about 2% and about 7% by weight of calcium.

22. The color-neutral refined protein component of Example 19, wherein the color-neutral refined protein component has a relative emulsion activity of between about 0.1 and about 2 relative to the emulsion activity of bovine serum albumin.

23. The color-neutral refined protein component of Example 19, wherein the color-neutral refined protein component comprises at least about 80% of visualized protein bands on a denaturing protein gel with a molecular weight of less than 200 kDa.

24. A method for producing a dairy milk analog comprising the steps of:
   a) obtaining at least one lipid component;
   b) obtaining at least one color-neutral refined protein component from a non-animal natural and/or modified non-animal natural source according to a method of one or more of Examples 9 to 18;
   c) combining and blending a quantity of the at least one lipid component, a quantity of the at least one color-neutral refined protein component, and a quantity of an aqueous component to generate a mixture; and
   d) emulsifying the mixture to provide a dairy milk analog.

25. The method of Example 24, wherein the lipid component is obtained from a non-animal natural and/or modified non-animal natural source.

26. The method of Example 24 or 25, wherein at least one of the non-animal natural or modified non-animal natural sources is a plant.

27. The method of Example 26, wherein the plant is a legume.

28. The method of Example 27, wherein the legume is pea.

29. The method of Examples 24 or 25, wherein the quantities of the lipid, protein, and aqueous components are selected so as to provide a dairy milk analog that comprises between about 1% and about 10% by weight of protein obtained from a non-animal natural or modified non-animal natural source and between about 0% and about 4% by weight of lipid obtained from a non-animal natural or modified non-animal natural source.

30. The method of Example 24, wherein the method further comprises the step of adding a carbohydrate component to the aqueous component or mixture, wherein the carbohydrate component does not comprise lactose.

31. The method of Example 24, wherein the method further comprises the step of adding calcium to the aqueous component or mixture.

32. The method of Example 24, wherein the method further comprises the step of sterilizing or pasteurizing the dairy milk analog.

33. A method for producing a dairy yoghurt analog comprising the steps of:
   a) obtaining at least one carbohydrate component;
   b) obtaining at least one lipid component;
   c) obtaining at least one color-neutral refined protein component from a non-animal natural and/or modified non-animal natural source according to a method of one or more of Examples 9 to 18;
   d) blending the at least one carbohydrate component, the at least one lipid component, and the at least one protein component with an aqueous component to generate a mixture;
   e) heating the mixture;
   emulsifying the mixture to generate an emulsified mixture;
   g) cooling the emulsified mixture;
   h) adding fermenting microorganisms to the emulsified mixture to generate a fermentation mixture; and
   i) incubating the fermentation mixture at an elevated temperature until the fermentation mixture is set and acidified to provide the dairy yoghurt analog.

34. The method of Example 33, wherein the lipid component is obtained from a non-animal natural or modified non-animal natural source.

35. The method of Examples 33 or 34, wherein at least one of the non-animal natural or modified non-animal natural sources is a plant.

36. The method of Example 35, wherein the plant is a legume.

37. The method of Example 36, wherein the legume is pea.

38. The method of Example 33, wherein the quantities of the carbohydrate, lipid, protein, and aqueous components are selected so as to provide a dairy yoghurt analog that comprises between about 1% and about 10% by weight of protein obtained from a non-animal natural or modified non-animal natural source and between about 0% and about 4% by weight of lipid obtained from a non-animal natural or modified non-animal natural source.

39. The method of Example 33, wherein the carbohydrate component does not comprise lactose.

40. The method of Example 33, wherein the method further comprises the step of adding calcium to the aqueous component or mixture.

41. The method of Example 33, wherein the fermenting microorganisms are selected from the group consisting of *Lactobacillus bulgaricus* and *Streptococcus thermophilus*.

42. The method of Example 33, wherein the elevated temperature is 45° C.

43. The method of Example 33, wherein the method further comprises the step of sterilizing or pasteurizing the dairy yoghurt analog.

44. A method for obtaining a yield of refined protein component from a non-animal natural and/or modified non-animal natural source comprising the steps of:
   a) obtaining a protein preparation from the non-animal natural or modified non-animal natural source;
   b) washing the protein preparation at a wash pH;
   c) extracting the protein preparation at an extraction pH to obtain an aqueous protein solution;
   d) separating the aqueous protein solution from non-aqueous components;
   e) adding salt;
   f) precipitating the protein from the aqueous protein solution at a precipitation pH to obtain a protein precipitate;
   g) separating the protein precipitate from non-precipitated components; and h) washing the protein precipitate to obtain the refined protein component at the substantial yield.

45. The method of Example 44, wherein the non-animal natural or modified non-animal natural source is a plant.

46. The method of Example 44, wherein the plant is a legume.

47. The method of Example 44, wherein the legume is pea.

48. The method of Example 44, wherein the wash pH is between about 3 and about 5.

49. The method of Example 44, wherein the extraction pH is between about 8 and about 9.

50. The method of Example 44, wherein the salt added is calcium dichloride at a concentration of between about 50 mM and about 100 mM.

51. The method of Example 44, wherein the precipitation pH is between about 5 and about 6.

52. The method of Examples 44, wherein the method further comprises the step of adding between about 0.05% and about 12% by weight of polysaccharide to the aqueous protein solution.

53. The method of Example 44, wherein the yield is between about 50% and about 90%.

54. A refined protein component, wherein the refined protein component is obtained from a non-animal natural and/or modified non-animal natural source by a method of one or more of the Examples 44 to 53.

55. The refined protein component of Example 54, wherein the refined protein component is a paste comprising between about 4% and about 25% by weight of protein, between about 0.1% and about 1.5% by weight of calcium, and between about 50% and about 90% by weight of water.

56. The refined protein component of Example 54, wherein the refined protein component is a dry powder comprising between about 70% and about 90% by weight of protein, and between about 2% and about 7% by weight of calcium.

57. The refined protein component of Example 54, wherein the refined protein component has a relative emulsion activity of between about 0.1 and about 2 relative to the emulsion activity of bovine serum albumin.

58. The refined protein component of Example 54, wherein the refined protein component comprises at least about 80% of visualized protein bands on a denaturing protein gel with a molecular weight of less than 200 kDa.

59. The refined protein component of one or more of Examples 44 to 58, wherein the refined protein component is color-neutral.

60. The refined protein component of one or more of Examples 44 to 58, wherein the refined protein component is not color-neutral.

61. A refined protein comprising between 5% to 97% by weight of a protein obtained from one or more non-animal natural or modified non-animal natural sources.

62. The refined protein of Example 61, wherein the percent by weight of the protein is between 20% and 90%.

63. The refined protein of Example 61, wherein the percent by weight of the protein is between 30% and 85%.

64. The refined protein of Example 61, wherein the percent by weight of the protein is between 40% and 80%.

65. The refined protein of Example 61, wherein the color is defined by an $L^*$ value of between 60 to 90, an $a^*$ value of between −6 to +6 and a $b^*$ value of between −20 to +20.

66. The refined protein of Example 61, wherein the color is defined by an $L^*$ value of between 65 to 85, an $a^*$ value of between about −4 to about +4 and a $b^*$ value of between −18 to +18.

67. The refined protein of Example 61, wherein the color is defined by an $L^*$ value of at least 65, an $a^*$ value of between at least −5 to +5 and a $b^*$ value of at least −16 to +16.

68. The refined protein of Example 61, wherein the color is defined by an $L^*$ value of at least 80, an $a^*$ value of between at least −3 to +3 and a $b^*$ value of at least −14 to +14.

69. The refined protein of one or more of Examples 61 to 68, wherein the refined protein is a paste, wet suspension or dry powder.

70. The refined protein of one or more of Examples 61 to 68, wherein the refined protein has a dry solids weight percentage of at least 5%.

71. The refined protein of one or more of Examples 61 to 68, wherein the refined protein has a dry solids weight percentage of at least 10%.

72. The refined protein of one or more of Examples 61 to 68, wherein the refined protein has a dry solids weight percentage of at least 15%.

73. The refined protein of one or more of Examples 61 to 68, wherein the refined protein has a dry solids weight percentage of at least 20%.

74. The refined protein of one or more of Examples 61 to 68, wherein the refined protein has a dry solids weight percentage of at least 25%.

75. The refined protein of one or more of Examples 61 to 68, wherein the refined protein has a dry solids weight percentage of at least 30%.

76. The refined protein of one or more of Examples 61 to 75, wherein the refined protein further comprises calcium and the calcium to protein ratio is between 0.5% w/w to 5% w/w.

77. The refined protein of one or more of Examples 61 to 75, wherein the refined protein further comprises calcium and the calcium to protein ratio is between 1% w/w to 6% w/w.

78. The refined protein of one or more of Examples 61 to 75, wherein the refined protein further comprises calcium and the calcium to protein ratio is between 3% w/w to 8% w/w.

79. The refined protein of one or more of Examples 61 to 75, wherein the refined protein further comprises calcium and the calcium to protein ratio is between 5% w/w to 10% w/w.

80. The refined protein of one or more of Examples 61 to 79, wherein the refined protein color neutral.

81. The refined protein of one or more of Examples 61 to 79, wherein the refined protein is not color neutral.

82. The refined protein of one or more of Examples 61 to 81, wherein the refined protein has a pH of between 4.5 and 11.

83. The refined protein of one or more of Examples 61 to 81, wherein the refined protein has a pH of between 6.5 and 10.

84. The refined protein of one or more of Examples 61 to 81, wherein the refined protein has a pH of between 5.5 and 8.

85. The refined protein of one or more of Examples 61 to 81, wherein the refined protein has a pH of between 5.7 and 6.7.

86. The refined protein of one or more of Examples 61 to 81, wherein the refined protein has a pH of at least 5.

87. The refined protein of one or more of Examples 61 to 81, wherein the refined protein has a pH of less than 9.

88. The refined protein of one or more of Examples 61 to 87, wherein the refined protein has a moisture content of between 3% and 90% by weight.

89. The refined protein of one or more of Examples 61 to 87, wherein the refined protein has a moisture content of at least 4% by weight.

90. The refined protein of one or more of Examples 61 to 87, wherein the refined protein has a moisture content of less than 80% by weight.

91. The refined protein of one or more of Examples 61 to 90, wherein the refined protein has a fat content of between 1% and 30% by weight.

92. The refined protein of one or more of Examples 61 to 90, wherein the refined protein has a fat content of at least 2% by weight 93. The refined protein of one or more of Examples 61 to 90, wherein the refined protein has a fat content of less than 25% by weight.

94. The refined protein of one or more of Examples 61 to 93, wherein the refined protein has a carbohydrate content of between 0% and 50% by weight.

95. The refined protein of one or more of Examples 61 to 93, wherein the refined protein has a carbohydrate content of at least 0% by weight 96. The refined protein of one or more of Examples 61 to 93, wherein the refined protein has a carbohydrate content of less than 25% by weight.

97. The refined protein of one or more of Examples 61 to 96, wherein the refined protein has a starch content of between 0% and 10% by weight.

98. The refined protein of one or more of Examples 61 to 96, wherein the refined protein has a starch content of at least 3% by weight 99. The refined protein of one or more of Examples 61 to 96, wherein the refined protein has a starch content of less than 10% by weight.

100. The refined protein of one or more of Examples 61 to 99, wherein the refined protein has a phosphorus content of between 0% and 6% by weight.

101. The refined protein of one or more of Examples 61 to 99, wherein the refined protein has a phosphorus content of at least 0.1% by weight.

102. The refined protein of one or more of Examples 61 to 99, wherein the refined protein has a phosphorus content of less than 4% by weight.

103. The refined protein of one or more of Examples 61 to 102, wherein the refined protein has a sodium and/or potassium content of less than 0.5% by weight.

104. The refined protein of one or more of Examples 61 to 103, wherein the refined protein has a ash content of between 0% and 20% by weight.

105. The refined protein of one or more of Examples 61 to 103, wherein the refined protein has a ash content of at least 1% by weight.

106. The refined protein of one or more of Examples 61 to 103, wherein the refined protein has a ash content of less than 10% by weight.

107. The refined protein of one or more of Examples 61 to 106, wherein the refined protein has a reducing capacity of between 5% and 50%.

108. The refined protein of one or more of Examples 61 to 106, wherein the refined protein has a reducing capacity of at least 6%.

109. The refined protein of one or more of Examples 61 to 106, wherein the refined protein has a reducing capacity of less than 46%.

110. The refined protein of one or more of Examples 61 to 109, wherein the refined protein has a total HPLC peak area for total extractable soluble sugars and organic acids of between 20,000 and 250,000.

111. The refined protein of one or more of Examples 61 to 109, wherein the refined protein has a total extractable soluble sugars and organic acids of at least 22,000.

112. The refined protein of one or more of Examples 61 to 109, wherein the refined protein has a total extractable soluble sugars and organic acids of less than 240,000

113. The refined protein of one or more of Examples 61 to 112, wherein the refined protein has a total peak area measured by GC analysis of volatile compounds component of between 50,000 3,000,000.

114. The refined protein of one or more of Examples 61 to 112, wherein the refined protein has a volatile compounds component of less than 2,500,000.

115. The refined protein of one or more of Examples 61 to 114, wherein the refined protein has a isoflavones component of between 0% dry mass and 0.1% of dry mass.

116. The refined protein of one or more of Examples 61 to 114, wherein the refined protein has a isoflavones component of less than 0.075% of dry mass.

117. The refined protein of one or more of Examples 61 to 116, wherein the refined protein has a tannins component of between 0% dry mass and 0.5% of dry mass.

118. The refined protein of one or more of Examples 61 to 116, wherein the refined protein has a tannins component of less than 0.3% of dry mass.

119. The refined protein of one or more of Examples 61 to 118, wherein the refined protein has an instability index of between 0.200 and 0.600.

120. The refined protein of one or more of Examples 61 to 118 wherein the refined protein has an instability index of at least 0.220.

121. The refined protein of one or more of Examples 61 to 118, wherein the refined protein has an instability index of less than 0.570.

122. The refined protein of one or more of Examples 61 to 121, wherein the refined protein has been produced in quantities of at least between 500-kg and 3000-kg, between 500-kg and 1000-kg, between 1000-kg and 2500-kg and between 1000-kg and 3500-kg.

Additionally, the disclosure has been described with reference to particular embodiments. However, it may be readily apparent to those skilled in the art that it is possible to embody the disclosure in specific forms other than those of the embodiments described above. The embodiments are merely illustrative and should not be considered restrictive. The scope of the disclosure is given by the appended claims, rather than the preceding description, and all variations and equivalents that fall within the range of the claims are intended to be embraced therein.

What is claimed is:

1. A method for obtaining a refined protein component from a non-animal natural and/or modified non-animal natural source comprising the steps of:
   a) obtaining a protein preparation from the non-animal natural or modified non-animal natural source;
   b) washing the protein preparation at a wash pH;
   c) aqueously extracting the protein preparation at an extraction pH to obtain an aqueous protein solution;
   d) separating the aqueous protein solution from non-aqueous components;
   e) heating the aqueous protein solution to a temperature of about 60° C.;

f) adding a calcium salt suitable for coagulating protein and adjusting the aqueous protein solution to a precipitation pH between about 6 and about 3 to precipitate protein and obtain a protein precipitate;

g) separating the protein precipitate from non-precipitated components; and h) washing the protein precipitate to obtain the refined protein component;

wherein step (f) is the only protein precipitation step in the method.

2. The method of claim 1, wherein the non-animal natural or modified non-animal natural source is a plant.

3. The method of claim 2, wherein the plant is a legume.

4. The method of claim 3, wherein the legume is pea.

5. The method of claim 1, wherein the wash pH in step (b) is between about 3 and about 5.

6. The method of claim 1, wherein the extraction pH is between about 8 and about 9.

7. The method of claim 1, wherein the calcium salt added is calcium dichloride at a concentration of between about 50 mM and about 100 mM.

8. The method of claim 1, wherein the method further comprises the step of adding between about 0.05% and about 12% by weight of polysaccharide to the aqueous protein solution.

9. The method of claim 1, wherein the refined protein component has an L* value of between 76 to 80, an a* value of between −2.5 to −0.7, and a b* value of between 4.5 to 12.

10. The method of claim 1, wherein the steps of (i) heating the aqueous protein solution to a temperature of about 60° C. and (ii) adding a calcium salt suitable for coagulating protein and adjusting the aqueous protein solution to a precipitation pH between about 6 and about 3 to precipitate protein and to obtain a protein precipitate occur together.

11. The method of claim 1 wherein the total peak area of a volatile compounds component in said refined protein component is less than 2,500,000 as measured by GC analysis.

* * * * *